United States Patent
Takashino et al.

(10) Patent No.: US 9,033,983 B2
(45) Date of Patent: May 19, 2015

(54) TREATMENT SYSTEM, TREATMENT INSTRUMENT, AND METHOD FOR TREATING LIVING TISSUE BY USE OF ENERGY

(75) Inventors: Tomoyuki Takashino, Hino (JP); Koji Iida, Sagamihara (JP); Toru Nagase, Tachikawa (JP)

(73) Assignee: OLYMPUS MEDICAL SYSTEMS CORP. (JP)

( * ) Notice: Subject to any disclaimer, the term of this patent is extended or adjusted under 35 U.S.C. 154(b) by 1073 days.

(21) Appl. No.: 12/906,234

(22) Filed: Oct. 18, 2010

(65) Prior Publication Data
US 2011/0028971 A1  Feb. 3, 2011

Related U.S. Application Data

(63) Continuation of application No. PCT/JP2008/057701, filed on Apr. 21, 2008.

(51) Int. Cl.
*A61B 18/12* (2006.01)
*A61B 18/14* (2006.01)
(Continued)

(52) U.S. Cl.
CPC ......... *A61B 18/1445* (2013.01); *A61B 18/1482* (2013.01); *A61B 2017/00212* (2013.01); *A61B 2018/00023* (2013.01); *A61B 2018/00345* (2013.01); *A61B 2018/00404* (2013.01); *A61B 2018/00619* (2013.01);
(Continued)

(58) Field of Classification Search
CPC ........... A61B 18/1445; A61B 18/1482; A61B 2018/00404; A61B 2018/00619; A61B 2018/1412; A61B 2018/1455
USPC ................................. 606/27, 34, 41, 51, 52
See application file for complete search history.

(56) References Cited

U.S. PATENT DOCUMENTS

| | | | | |
|---|---|---|---|---|
| 5,217,460 A | * | 6/1993 | Knoepfler | 606/52 |
| 5,443,463 A | | 8/1995 | Stern et al. | 606/51 |
| 5,496,312 A | * | 3/1996 | Klicek | 606/34 |

(Continued)

FOREIGN PATENT DOCUMENTS

| | | |
|---|---|---|
| JP | 4-208149 | 7/1992 |
| JP | 10-504485 | 5/1998 |

(Continued)

OTHER PUBLICATIONS

International Preliminary Examination Report on Patentability issued Dec. 29, 2010 in corresponding International Application No. PCT/JP2008/057701.

(Continued)

*Primary Examiner* — Michael Peffley
*Assistant Examiner* — Daniel Fowler
(74) *Attorney, Agent, or Firm* — Ostrolenk Faber LLP

(57) ABSTRACT

A treatment system includes a seal member, a maintaining member and a control section, and is configured to exert energy to a living tissue to treat the living tissue. The seal member is configured to join a sealed region which seals desirable regions of at least two living tissues when the energy is exerted to the sealed region. The maintaining member is configured to maintain the living tissues in the vicinity of the sealed region being brought into contact with each other when the energy is exerted to the living tissues. The control section is configured to offset energy output timings of the seal member and the maintaining member.

5 Claims, 32 Drawing Sheets

(51) Int. Cl.
*A61B 17/00* (2006.01)
*A61B 18/00* (2006.01)

(52) U.S. Cl.
CPC .............. *A61B 2018/00726* (2013.01); *A61B 2018/1412* (2013.01); *A61B 2018/1455* (2013.01)

(56) References Cited

U.S. PATENT DOCUMENTS

| | | | |
|---|---|---|---|
| 6,024,741 A | | 2/2000 | Williamson, IV et al. |
| 6,024,744 A | * | 2/2000 | Kese et al. ................ 606/51 |
| 6,050,996 A | * | 4/2000 | Schmaltz et al. ........... 606/51 |
| 6,071,281 A | * | 6/2000 | Burnside et al. ............ 606/41 |
| 6,152,923 A | * | 11/2000 | Ryan ........................ 606/51 |
| 6,514,252 B2 | * | 2/2003 | Nezhat et al. ............. 606/48 |
| 6,676,660 B2 | * | 1/2004 | Wampler et al. ............ 606/51 |
| 6,679,882 B1 | * | 1/2004 | Kornerup ................... 606/51 |
| 6,953,461 B2 | * | 10/2005 | McClurken et al. .......... 606/51 |
| 7,041,095 B2 | * | 5/2006 | Wang et al. ................ 606/32 |
| 7,232,440 B2 | * | 6/2007 | Dumbauld et al. .......... 606/51 |
| 7,270,664 B2 | * | 9/2007 | Johnson et al. ............. 606/51 |
| 7,942,874 B2 | * | 5/2011 | Eder et al. ................ 606/50 |
| 2006/0052778 A1 | * | 3/2006 | Chapman et al. ........... 606/51 |
| 2006/0064086 A1 | | 3/2006 | Odom |

FOREIGN PATENT DOCUMENTS

| | | |
|---|---|---|
| JP | 2003-235865 | 8/2003 |
| JP | 2003-245285 | 9/2003 |
| JP | 2007-75468 | 3/2007 |
| WO | WO 2004/032777 | 4/2004 |

OTHER PUBLICATIONS

Office Action issued by the Chinese Patent Office on Jan. 29, 2012 in connection with corresponding Chinese Patent Application No. 200880128734.0.

Translation of Office Action issued by the Chinese Patent Office on Jan. 29, 2012 in connection with corresponding Chinese Patent Application No. 200880128734.0.

Search Report issued by European Patent Office in connection with corresponding application No. EP 08 75 1891 on Nov. 9, 2011.

International Search Report and Written Opinion mailed Jun. 24, 2008 in corresponding PCT International Application No. PCT/JP2008/057701.

* cited by examiner

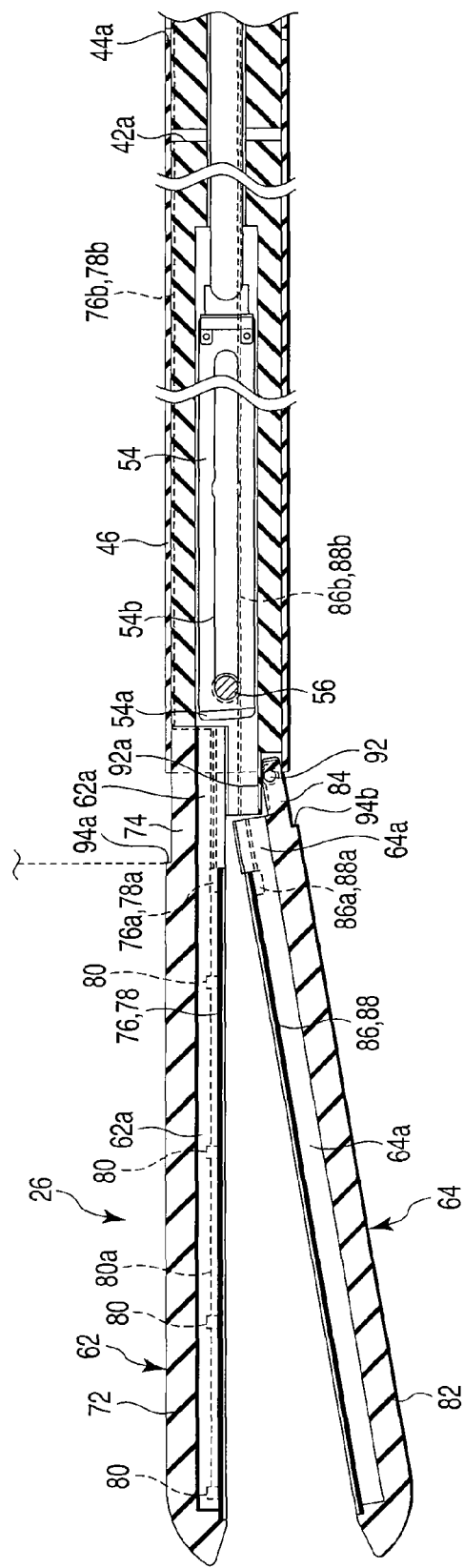
F I G. 2B

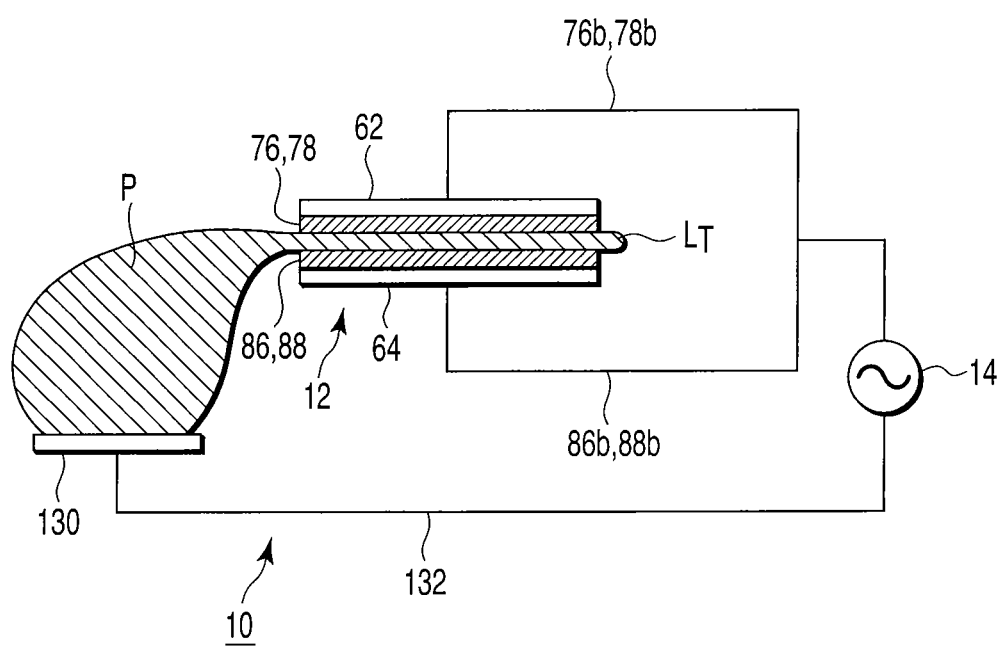
F I G. 3E

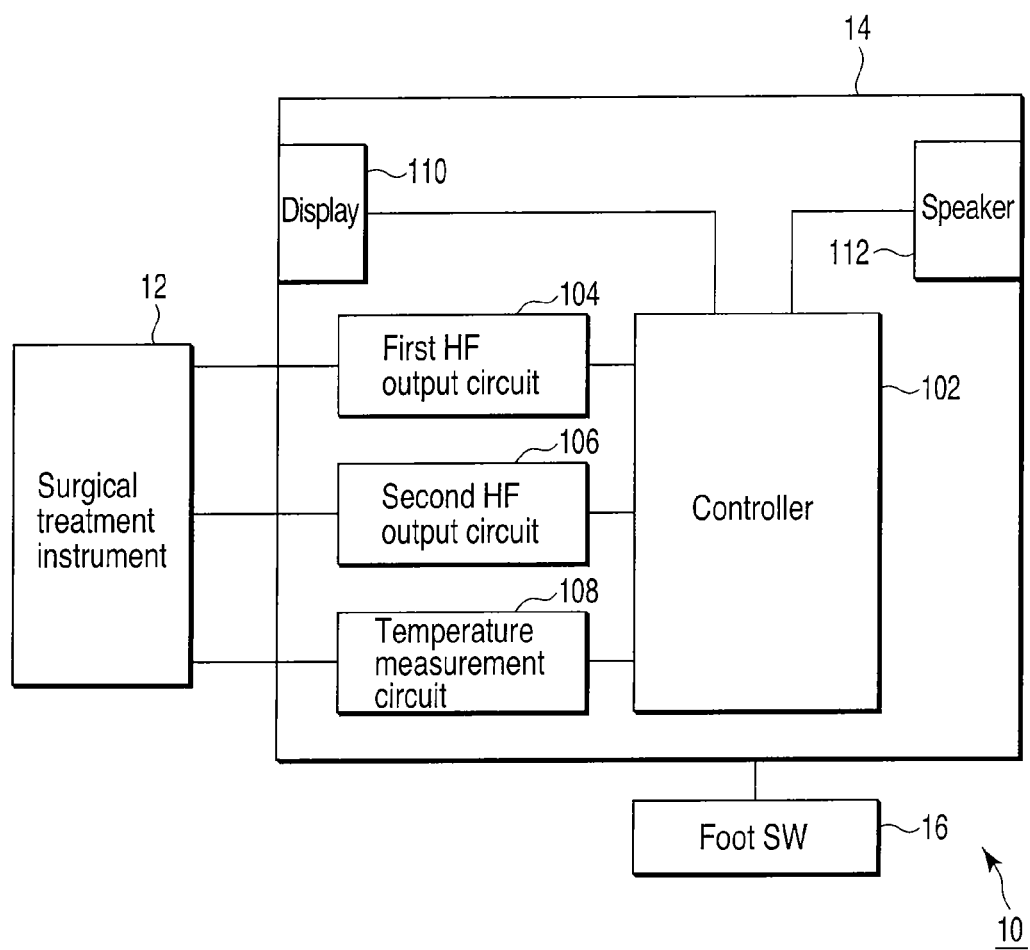
F I G. 4

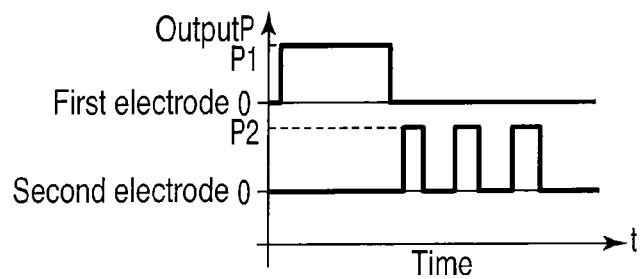
F I G. 6A
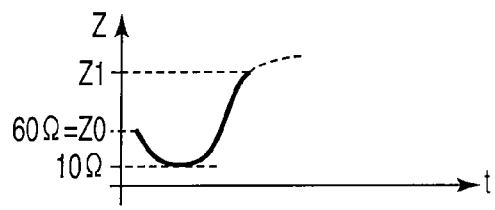
F I G. 6B
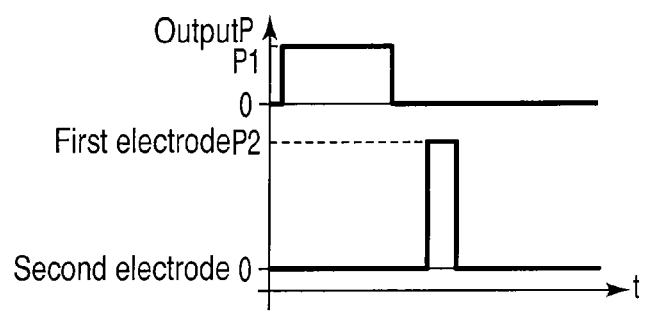
F I G. 6C
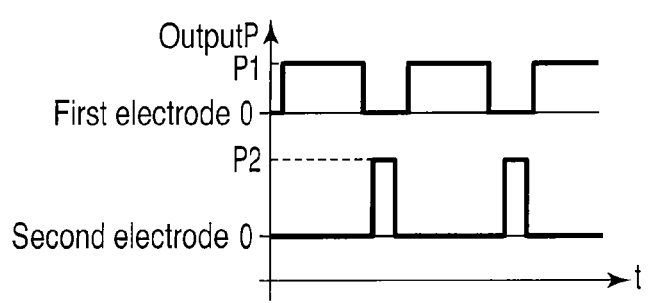
F I G. 6D

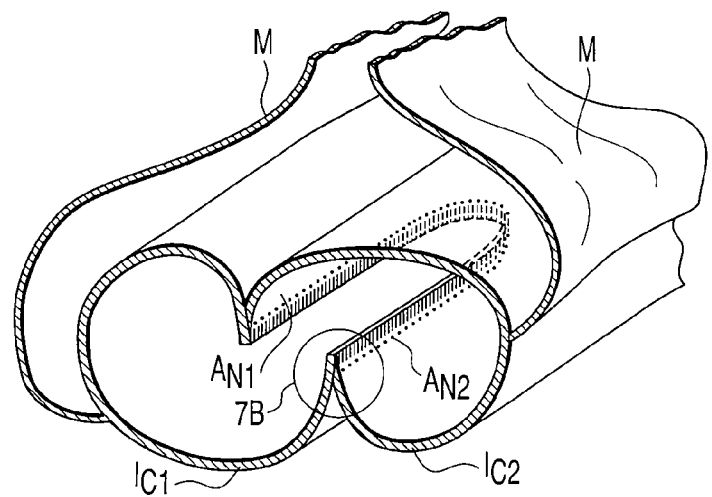
F I G. 7A
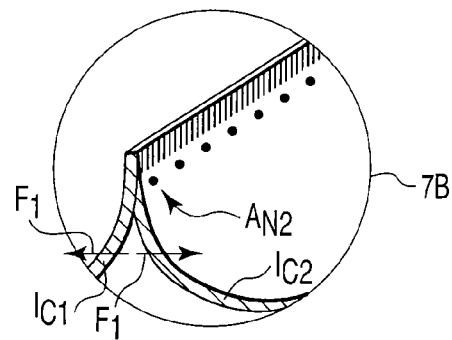
F I G. 7B
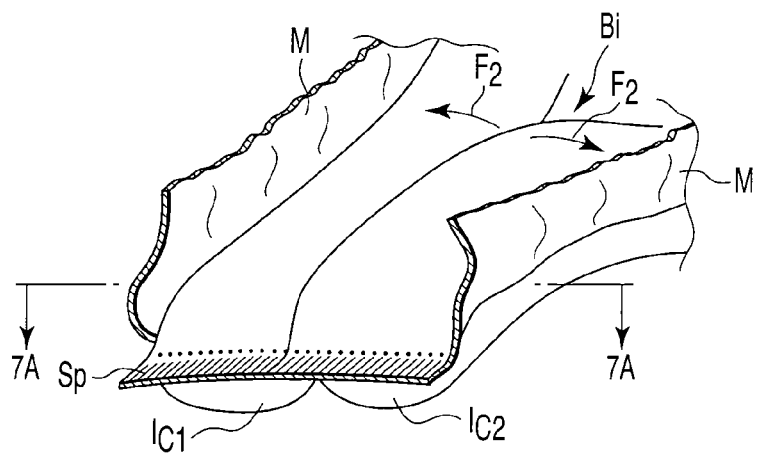
F I G. 7C

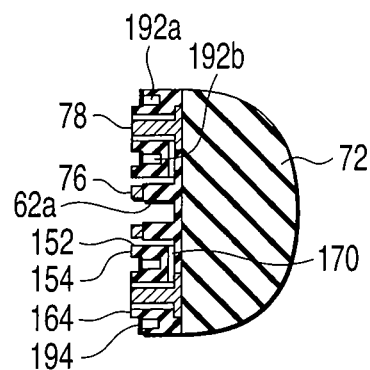
F I G. 9C
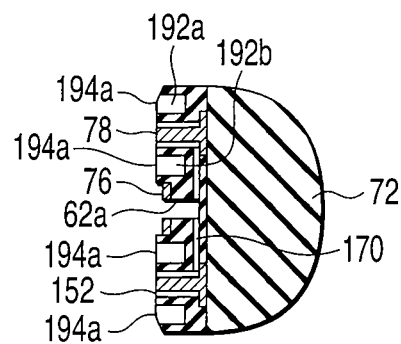
F I G. 9D

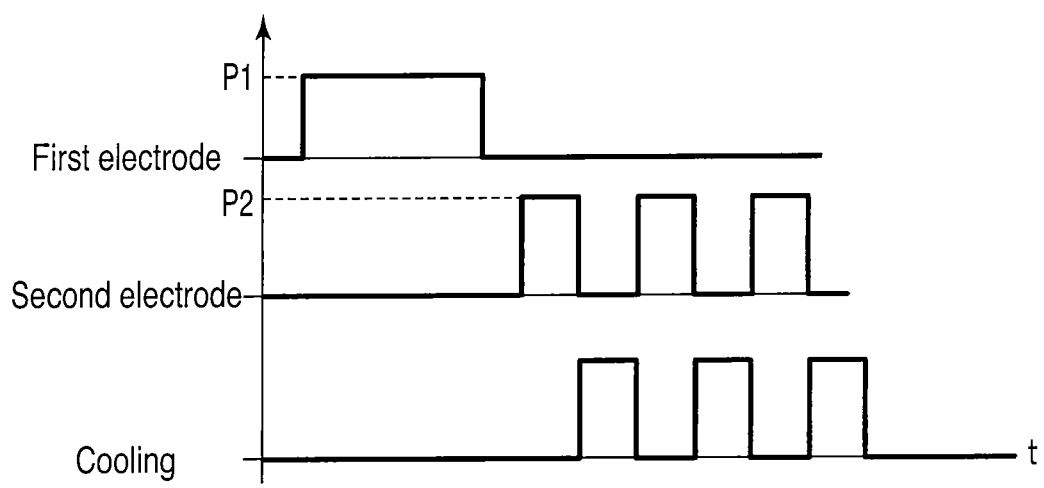
F I G. 12A
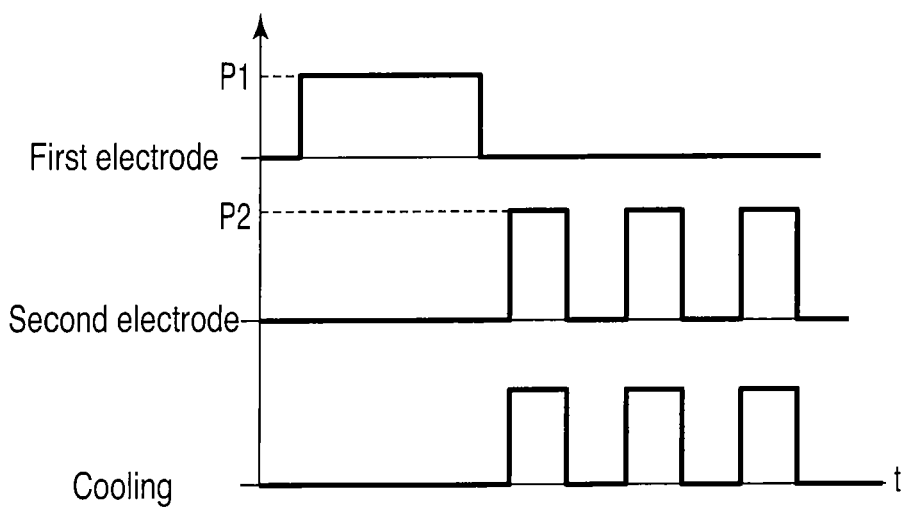
F I G. 12B

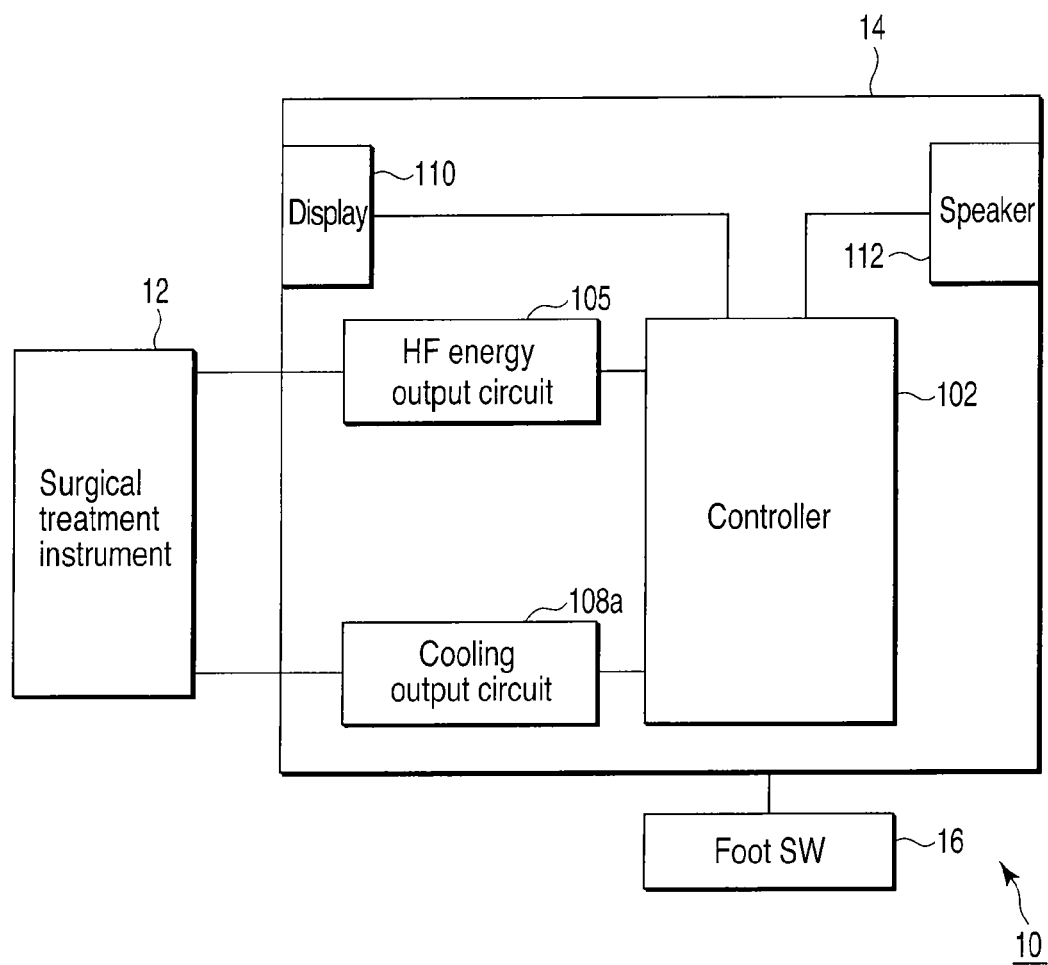
F I G. 14

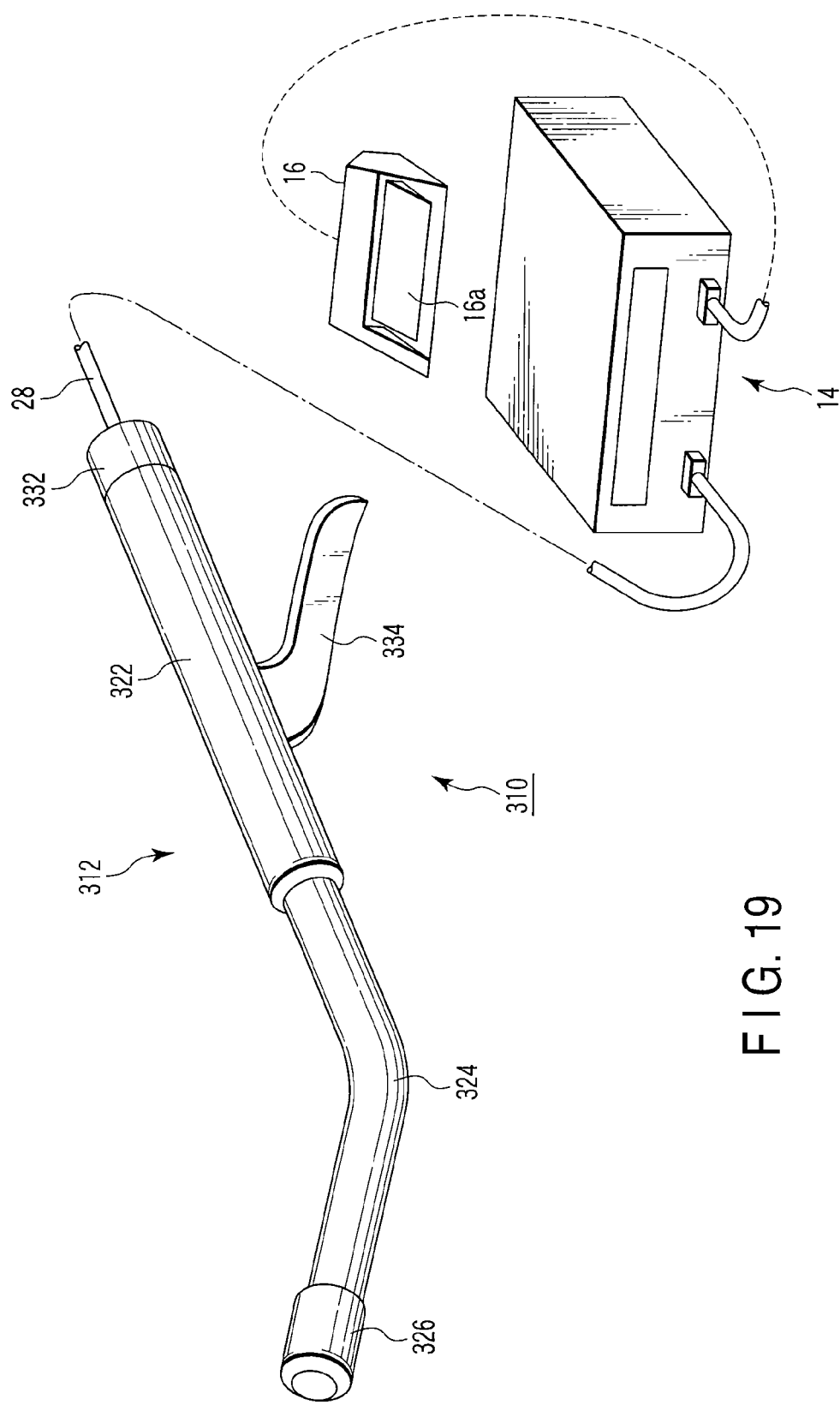
F I G. 19

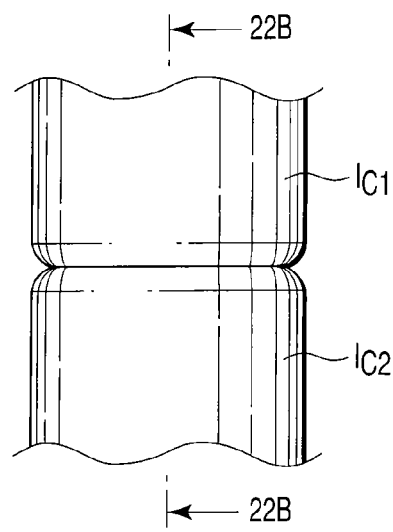
F I G. 22A
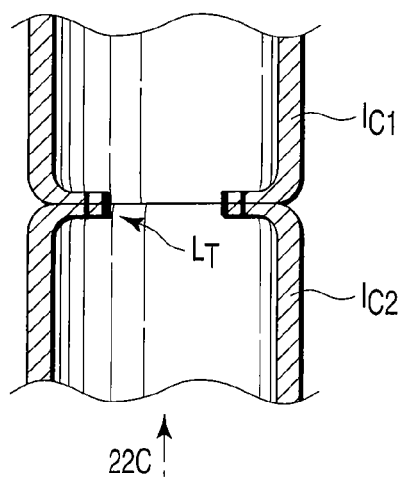
F I G. 22B
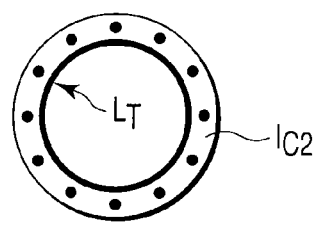
F I G. 22C

TREATMENT SYSTEM, TREATMENT INSTRUMENT, AND METHOD FOR TREATING LIVING TISSUE BY USE OF ENERGY

CROSS-REFERENCE TO RELATED APPLICATIONS

This is a Continuation Application of PCT Application No. PCT/JP2008/057701, filed Apr. 21, 2008, which was published under PCT Article 21(2) in Japanese.

BACKGROUND OF THE INVENTION

1. Field of the Invention

This invention relates to a treatment system for treating a living tissue by use of energy, and a method for treating a living tissue by use of energy.

2. Description of the Related Art

In U.S. Pat. No. 5,443,463, coagulation forceps provided with a plurality of electrodes are disclosed. In the forceps, an RF power output from one electrosurgical power supply is transmitted to the electrodes through an indifferent electrode connector. Therefore, the coagulation forceps treat a living tissue with high-frequency energy through the electrodes controlled in the same state.

BRIEF SUMMARY OF THE INVENTION

A treatment system configured to exert energy to a living tissue to treat the living tissue according to the invention comprises: a seal member configured to join a sealed region which seals desirable regions of at least two living tissues when the energy is exerted to the sealed region; a maintaining member configured to maintain the living tissues in the vicinity of the sealed region being brought into contact with each other when the energy is exerted to the living tissues; and a control section configured to offset energy output timings of the seal member and the maintaining member.

A treatment system configured to exert energy to a living tissue to treat the living tissue according to the invention comprises: a pair of holding members each having a holding face to hold at least two living tissues; an operation handle operated so that at least one of the holding faces relatively moves with respect to the other holding face; a first joining member configured to be disposed on at least one of the holding faces and exerts the energy to the at least two living tissues so that the tissues are joined to each other in a sealed state; a second joining member provided in the vicinity of the first joining member and discretely disposed to exert the energy to the living tissue while maintaining a state where the living tissue around the living tissues joined by the first joining member is brought into contact with the second joining member; and an energy output control section configured to offset the energy output timings of the first and second joining members.

A treatment system configured to exert energy to a living tissue to treat the living tissue according to the invention comprises: a seal member configured to exert the energy to at least two living tissues to join the living tissues in a state where desirable regions of the living tissues are sealed; a maintaining member configured to be integrally disposed on the seal member and exert the energy to the living tissues in a state where the living tissues are brought into contact with each other, thereby maintaining the contact of the living tissues; a cooling member provided in the vicinity of the maintaining member to cool the maintaining member; and a control section configured to control the energy output timings of the seal member, the maintaining member and the cooling member, respectively.

A according to the invention comprises treatment method for exerting energy to a living tissue to treat the living tissue according to the invention comprises: sealing desirable portions of at least two living tissues; and maintaining a state where the at least two living tissues are brought into contact with each other in the vicinity of a position where the desirable portions of the at least two living tissues are sealed at a timing to seal the desirable portions of the at least two living tissues and at an offset timing thereof.

A treatment instrument configured to exert energy to a living tissue to treat the living tissue according to the invention comprises: a seal member configured to join a sealed region which seals desirable regions of at least two living tissues when the energy is exerted to the sealed region; and a maintaining member configured to be provided independently of the seal member and maintain the living tissues in the vicinity of the sealed region being brought into contact with each other when energy is exerted separately from the seal member.

A treatment instrument configured to exert energy to a living tissue to treat the living tissue according to the invention comprises: a seal member configured to join a sealed region which seals desirable regions of at least two living tissues when the energy is exerted to the sealed region; a maintaining member configured to be provided independently of the seal member and maintain the living tissues in the vicinity of the sealed region being brought into contact with each other when energy is exerted separately from the seal member; and a cooling member configured to be provided in the vicinity of the maintaining member to cool the maintaining member and/or the vicinity of the maintaining member, wherein the output timing of the seal member is offset by the output timings of the maintaining member and the cooling member.

BRIEF DESCRIPTION OF THE SEVERAL VIEWS OF THE DRAWING

FIG. 2B is a schematic vertical sectional view showing the shaft and the opened first and second holding members of the holding section of the energy treatment instrument in the treatment system according to the first embodiment;

FIG. 3E is a schematic diagram showing that the high-frequency energy is applied to the living tissue to treat the tissue with a monopolar surgical treatment instrument of the treatment system according to the first embodiment;

FIG. 4 is a schematic block diagram of the treatment system according to the first embodiment;

FIG. 6A is a schematic graph showing one example of an input process of inputting the high-frequency energy into the living tissue with respect to time in a case where the treatment using the high-frequency energy is performed with respect to the living tissue by use of a treatment system according to a modification of the first embodiment;

FIG. 6B is a schematic graph showing the variance of impedance with respect to a time when predetermined high-frequency energy is input into the living tissue in a case where the treatment using the high-frequency energy is performed with respect to the living tissue by use of the treatment system according to the first embodiment;

FIG. 6C is a schematic graph showing one example of the input process of inputting the high-frequency energy into the living tissue with respect to the time in a case where the treatment using the high-frequency energy is performed with respect to the living tissue by use of the treatment system according to the modification of the first embodiment;

FIG. 6D is a schematic graph showing one example of the input process of inputting the high-frequency energy into the living tissue with respect to the time in a case where the treatment using the high-frequency energy is performed with respect to the living tissue by use of the treatment system according to the modification of the first embodiment;

FIG. 7A is a schematic perspective view showing a state where two intestinal canals of a small intestine are anastomosed, and a schematic diagram cut along the 7A-7A line of FIG. 7C described later;

FIG. 7B is a schematic diagram showing an enlarged part denoted with symbol 7B of FIG. 7A;

FIG. 7C is a schematic diagram showing a state where two intestinal canals of the small intestine are anastomosed, and then the ends of the intestinal canals are closed;

FIG. 9C is a schematic transverse sectional view cut along the 9B-9B line of FIG. 9A and showing a modification of the first holding member in the holding section of the energy treatment instrument of the treatment system according to a modification of the third modification of the first embodiment;

FIG. 9D is a schematic transverse sectional view cut along the 9B-9B line of FIG. 9A and showing a modification of a first holding member in a holding section of an energy treatment instrument of a treatment system according to a further modification of the third modification of the first embodiment;

FIG. 12A is a schematic graph showing one example of an input process of the high-frequency energy into the living tissue with respect to time in the case where the treatment using the high-frequency energy is performed with respect to the living tissue by use of the treatment system according to the third modification of the first embodiment;

FIG. 12B is a schematic graph showing one example of the input process of the high-frequency energy into the living tissue with respect to the time in the case where the treatment using the high-frequency energy is performed with respect to the living tissue by use of the treatment system according to the third modification of the first embodiment;

FIG. 14 is a schematic block diagram of the treatment system according to the fourth modification of the first embodiment;

FIG. 19 is a schematic diagram showing a modification of a treatment system according to a second embodiment;

FIG. 22A is a schematic diagram showing a state where intestinal canals are joined to each other by use of the energy treatment instrument according to the second embodiment;

FIG. 22B is a schematic vertical sectional view cut along the 22B-22B line of FIG. 22A and showing the state where the intestinal canals are joined to each other by use of the energy treatment instrument according to the second embodiment; and FIG. 22C is a schematic diagram showing that the state where the intestinal canals are joined to each other by use of the energy treatment instrument according to the second embodiment is observed from the direction of arrow 22C of FIG. 22B.

DETAILED DESCRIPTION OF THE INVENTION

Hereinafter, the best mode for carrying out this invention will be described with reference to the drawings.

[First Embodiment]

A first embodiment will be described with reference to FIGS. 1A to 7C.

Here, as an example of an energy treatment instrument (a treatment instrument), a linear type surgical treatment instrument 12 for performing a treatment, for example, through an abdominal wall will be described.

Figure 1A:
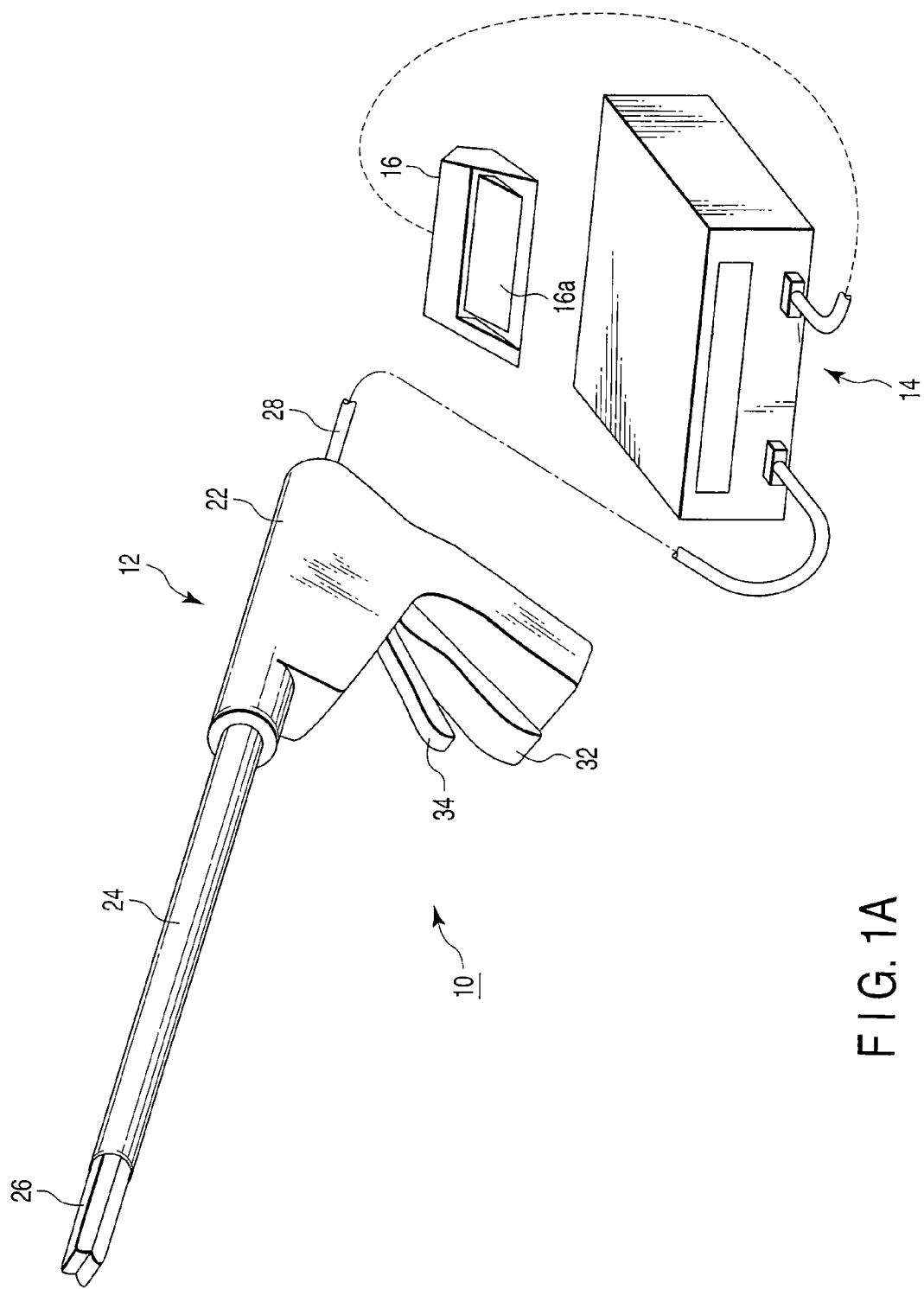
FIG. 1A is a schematic diagram showing a treatment system according to a first embodiment of the present invention.

As shown in FIG. 1A, a treatment system 10 includes the energy treatment instrument 12, an energy source (a control section) 14 and a foot switch 16.

The energy treatment instrument 12 includes a handle 22, a shaft 24 and an openable/closable holding section 26. The handle 22 is connected to the energy source 14 via a cable 28. The energy source 14 is connected to the foot switch (may be a hand switch) 16.

It is to be noted that the foot switch 16 includes a pedal 16a. In consequence, the pedal 16a of the foot switch 16 is switched on/off by an operator to perform/stop the supply of the energy from the energy source 14 to the surgical treatment instrument 12. When the pedal 16a is pressed, the high-frequency energy is output based on an appropriately set state (a state where an energy output amount, an energy output timing or the like is controlled). When the pressed pedal 16a is released, the output of the high-frequency energy is forcibly stopped.

The handle 22 is formed into such a shape as to be easily held by the operator, and is substantially formed into, for example, an L-shape. One end of the handle 22 is provided with the shaft 24. The cable 28 extends from the proximal end of the handle 22 disposed coaxially with respect to the shaft 24.

On the other hand, the handle 22 functions a grasping section to be grasped by the operator on the other end side thereof. The handle 22 includes a holding section opening/closing knob 32 disposed on the other end side of the handle. The holding section opening/closing knob 32 is connected to the proximal end of a sheath 44 (see FIGS. 2A and 2B) of the shaft 24 in the substantially middle portion of the handle 22 as described later. When the holding section opening/closing knob 32 comes close to or away from the other end of the handle 22, the sheath 44 moves along the axial direction thereof. The handle 22 further includes a cutter driving knob 34 for moving a cutter 54 described later in a state where the knob 34 is disposed in parallel with the holding section opening/closing knob 32.

Figure 1B:
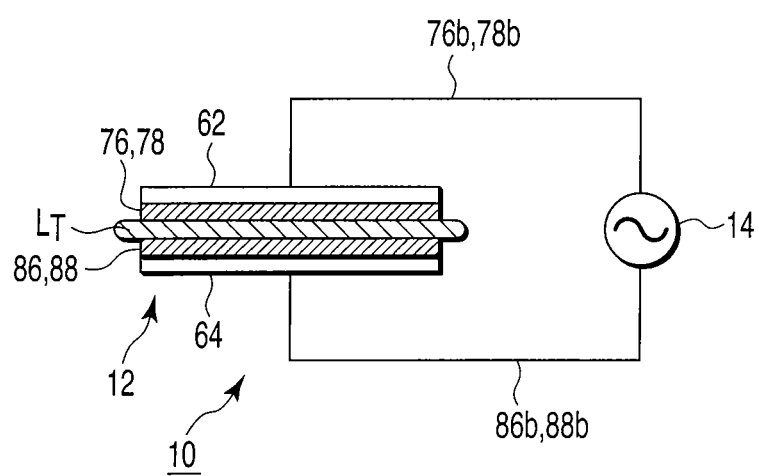
FIG. 1B is a schematic diagram showing that high-frequency energy is applied to a living tissue to treat the tissue with a bipolar surgical treatment instrument of the treatment system according to the first embodiment.
Figure 2A:
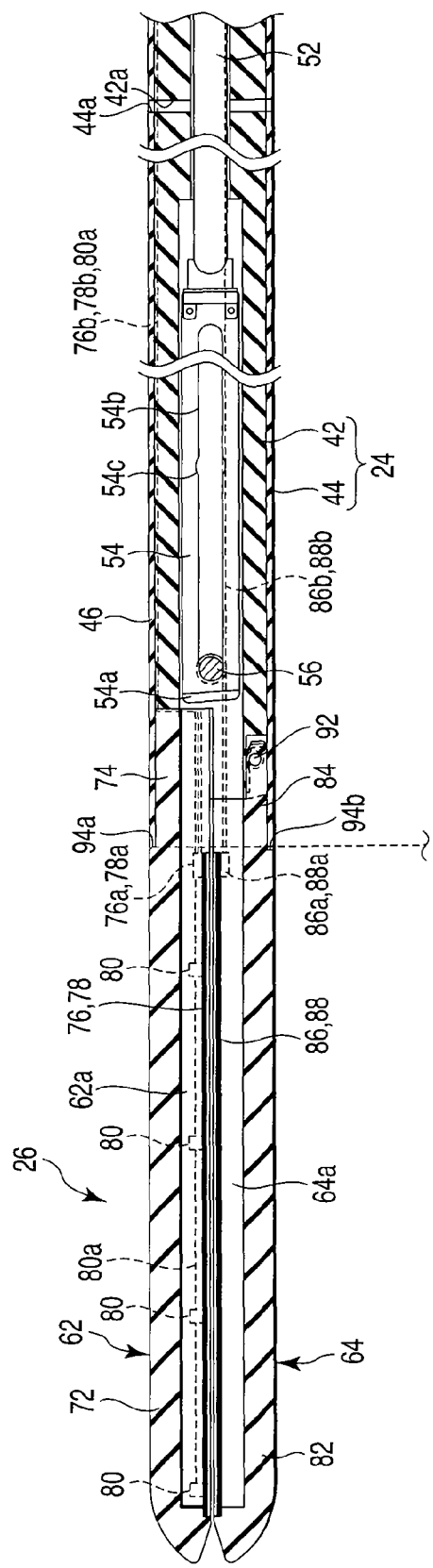
FIG. 2A is a schematic vertical sectional view showing a shaft and closed first and second holding members of a holding section of an energy treatment instrument in the treatment system according to the first embodiment.

As shown in FIGS. 2A and 2B, the shaft 24 includes a cylindrical member 42, and the sheath 44 slidably disposed outside the cylindrical member 42. The proximal end of the cylindrical member 42 is fixed to the handle 22 (see FIG. 1). The sheath 44 is slidable along the axial direction of the cylindrical member 42.

A recess portion 46 is formed along the axial direction of the cylindrical member 42 outside the member 42. The recess portion 46 is provided with a first electrode energization line 76b of a first continuous electrode (an output section) 76 described later, and a second electrode energization line 78b of a first discrete electrode (an output section) 78 described later. Although not shown, the first and second electrode energization lines 76b and 78b are interposed among first and second electrode connectors 76a and 78a described later and the cable 28. The first and second connectors 76a and 78a, the first electrode energization line 76b, the second electrode energization line 78b and the cable 28 are preferably integrated into one component.

Through the cylindrical member 42, there are inserted a third electrode energization line 86b of a second continuous electrode (an output section) 86 described later and a fourth electrode energization line 88b of a second discrete electrode (an output section) 88 described later. Although not shown, the third and fourth electrode energization lines 86b and 88b are interposed among third and fourth electrode connectors 86a and 88a described later and the cable 28. The third and fourth electrode connectors 86a and 88a and the cable 28 are preferably integrated into one component.

A driving rod 52 is disposed in the cylindrical member 42 of the shaft 24 so that the rod 52 can move along the axial direction thereof. The distal end of the driving rod 52 is provided with the thin-plate-like cutter (an auxiliary treatment instrument) 54. Therefore, when the cutter driving knob 34 is operated, the cutter 54 moves via the driving rod 52.

The distal end of the cutter 54 is provided with a blade 54a, and the distal end of the driving rod 52 is fixed to the proximal end of the cutter 54. A long groove 54b is formed between the distal and proximal ends of the cutter 54. In the long groove 54b, a movement regulation pin 56 extending in an orthogonal direction to the axial direction of the shaft 24 is fixed to the cylindrical member 42 of the shaft 24. Therefore, the cutter 54 moves along the long groove 54b via the movement regulation pin 56. In consequence, the cutter 54 moves in a straight line.

At this time, the cutter 54 is disposed in a cutter guide groove (a channel, a fluid discharge groove) 62a of a first holding member 62 and a cutter guide groove (a channel, a fluid discharge groove) 64a of a second holding member 64 described later.

It is to be noted that engagement portions 54c which engage with the movement regulation pin 56 to control the movement of the cutter 54 are formed in at least three portions, i.e., at one end, the other end and between the ends of the long groove 54b of the cutter 54.

As shown in FIGS. 1A, 2A and 2B, the holding section 26 is provided on the distal end of the shaft 24. As shown in FIGS. 2A and 2B, the holding section 26 includes the first holding member (a first jaw) 62 and the second holding member (a second jaw) 64.

The first and the second holding members 62, 64 themselves preferably entirely have insulation properties, respectively. The first holding member 62 integrally includes a first holding member main body (hereinafter referred to mainly as the main body) 72 and a base portion 74 provided on the proximal end of the main body 72. The first holding member main body 72 and the base portion 74 are provided with the cutter guide groove 62a for guiding the cutter 54.

As shown in FIGS. 2A to 3C, the main body 72 of the first holding member 62 is provided with a plurality of recess portions 72a, and a holding face 72b.

Moreover, in the plurality of recess portions 72a of the main body 72, one first continuous electrode 76 and a plurality of first discrete electrodes 78 are arranged. That is, the first holding member 62 is provided with the first continuous electrode 76 and the first discrete electrodes 78 as output members or energy release portions.

The first continuous electrode (a seal member, a first joining member) 76 is formed continuously without any cut. The first continuous electrode 76 is continuously formed into, for example, a substantial U-shape, and has two ends in the proximal end of the main body 72 of the first holding member 62. At least one of the two ends of the first continuous electrode 76 is electrically connected to the first electrode connector 76a disposed in the one end thereof. The first electrode connector 76a is connected to the cable 28 extended from the handle 22 via the first electrode energization line 76b. Moreover, the first continuous electrode 76 is connected to a first high-frequency energy output circuit 104 of the energy source 14 described later.

A space between the two ends of the first continuous electrode 76 is provided with a cutter guide groove (conveniently denoted with symbol 62a which is the same as that of the cutter guide groove 62a of the first holding member 62) for guiding the cutter 54 together with the main body 72 and the base portion 74 of the first holding member 62.

The first discrete electrodes (a maintaining member, a second joining member) 78 are discretely arranged outside the first continuous electrode 76. The plurality of first discrete electrodes 78 having the same shape are arranged at substantially equal intervals along a substantially U-shaped virtual track. The first discrete electrodes 78 are formed into, for example, a circular shape. The first discrete electrodes 78 are arranged with a substantially predetermined space being left therebetween, and the respective discrete electrodes 78 are arranged as much as an appropriate distance away from the first continuous electrode 76. The first discrete electrodes 78 are positioned so that when a treatment is performed, a living tissue $L_T$ between the first discrete electrode 78 and the second discrete electrode 88 of the second holding member 64 is denatured by heat, but the electrodes are positioned so that the denaturation of the living tissue $L_T$ between the first discrete electrodes 78 of the first holding member 62 due to the heat and the denaturation of the living tissue between the first discrete electrode 78 and the first continuous electrode 76 due to the heat are prevented as much as possible.

Although not shown, the plurality of first discrete electrodes 78 are electrically connected to one another in the main body 72, and are also electrically connected to the second electrode connector 78a disposed in parallel with the first electrode connector 76a. The second electrode connector 78a is connected to the cable 28 extended from the handle 22 via the second electrode energization line 78b. Moreover, the first discrete electrodes 78 are connected to a second high-frequency energy output circuit 106 of the energy source 14 described later.

It is to be noted that the holding face 72b of the surfaces of the first continuous electrode 76 and the first discrete electrodes 78 is formed to be one step higher. The holding face 72b comes closer to a facing main body 82 of the second holding member 64 than the surfaces of the first continuous electrode 76 and the first discrete electrodes 78, and abuts on a facing holding face (conveniently denoted with symbol 82b) of the main body 82 of the second holding member 64.

Figure 3A:
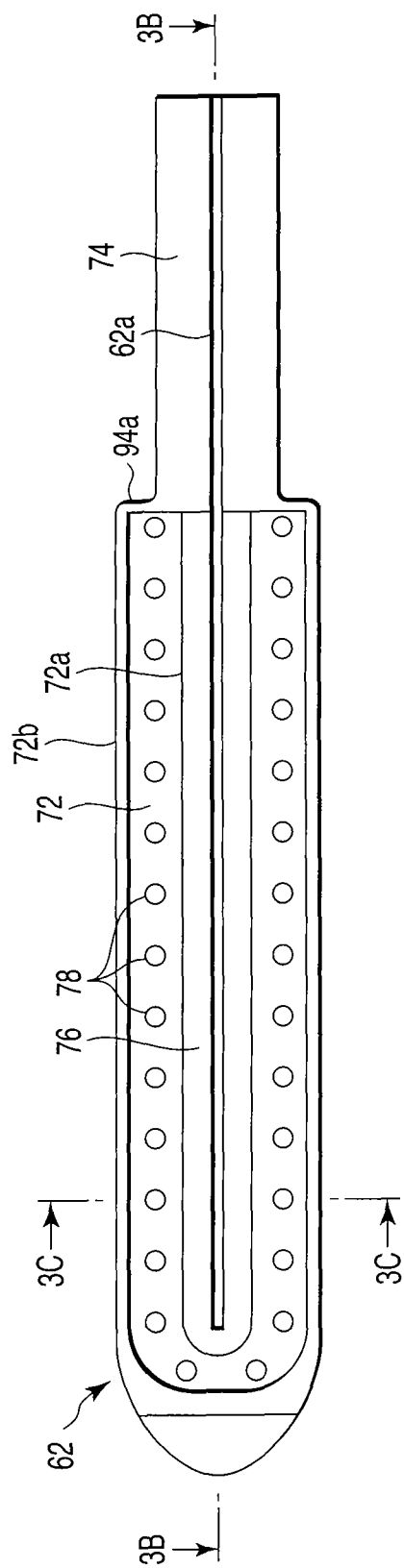
FIG. 3A is a schematic plan view showing the first holding member on a side close to the second holding member in the holding section of the energy treatment instrument of the treatment system according to the first embodiment.
Figure 3B:
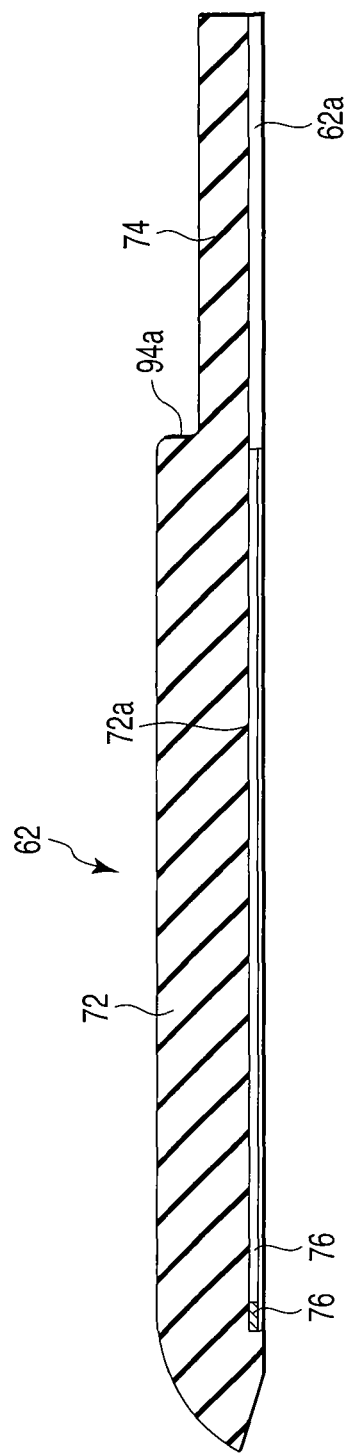
FIG. 3B is a schematic vertical sectional view showing the first holding member cut along the 3B-3B line of FIG. 3A in the holding section of the energy treatment instrument of the treatment system according to the first embodiment.
Figure 3C:
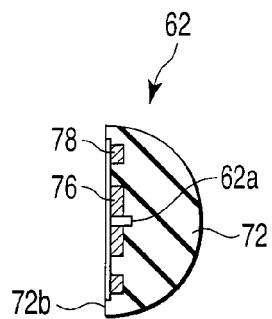
FIG. 3C is a schematic transverse sectional view showing the first holding member cut along the 3C-3C line of FIG. 3A in the holding section of the energy treatment instrument of the treatment system according to the first embodiment.
Figure 3D:
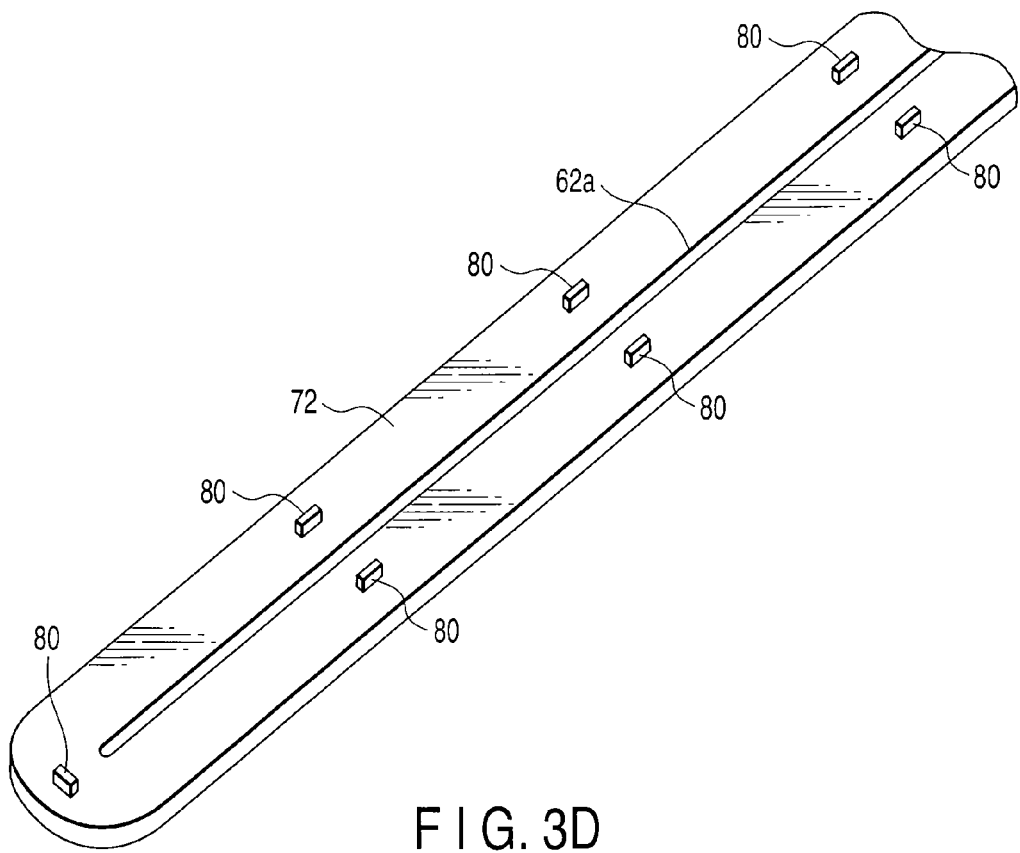
FIG. 3D is a schematic diagram showing the back surface of an electrode disposed on a main body of the first holding member on the side close to the second holding member in the holding section of the energy treatment instrument of the treatment system according to the first embodiment.

As shown in FIG. 3D, a plurality of temperature sensors 80 are embedded in the main body 72 of the first holding member 62. Here, as shown in FIGS. 2A and 2B, the plurality of temperature sensors 80 are arranged on the back surfaces of the first discrete electrodes 78 or in the vicinities of the first discrete electrodes 78. Therefore, it is possible to measure an approximate temperature T of the living tissue $L_T$ which comes in contact with the first discrete electrodes 78. It is to be noted that the temperature sensors 80 are connected to a temperature measurement circuit 108 described later via a temperature sensor signal line 80a in the same manner as in the first electrode energization line 76b of the first continuous electrode 76 and the second electrode energization line 78b of the first discrete electrodes 78.

The second holding member 64 integrally includes the second holding member main body 82 and a base portion 84 provided at the proximal end of the main body 82. The second holding member main body 82 and the base portion 84 are provided with the cutter guide groove 64a for guiding the cutter 54.

The main body 82 of the second holding member 64 is provided with a recess portion (conveniently denoted with symbol 82a) and the holding face 82b.

Moreover, in the recess portion 82a of the main body 82, the second continuous electrode 86 and the second discrete electrodes 88 are arranged. That is, the second holding member 64 is provided with the second continuous electrode 86 and the second discrete electrodes 88 as output members or energy release portions.

The second continuous electrode (a seal member, a first joining member) 86 is disposed symmetrically with respect to the first continuous electrode 76 disposed in the first holding member 62. Therefore, a space between the two ends of the second continuous electrode 86 is provided with a cutter guide groove (conveniently denoted with symbol 64a which is the same as that of the cutter guide groove 64a of the second holding member 64) for guiding the cutter 54 together with the main body 82 and the base portion 84 of the second holding member 64. The second discrete electrodes 88 are arranged symmetrically with respect to the first discrete electrodes 78 arranged in the first holding member 62. Therefore, the detailed description of the second continuous electrode 86 and the second discrete electrodes 88 is omitted.

It is to be noted that the second continuous electrode 86 is electrically connected to the third electrode connector 86a disposed at the end facing the end opposite to the first electrode connector 76a. Moreover, the third electrode connector 86a is connected to the cable 28 extended from the handle 22 via the third electrode energization line 86b. Moreover, the second continuous electrode 86 is connected to the first high-frequency energy output circuit 104 of the energy source 14 described later.

The second discrete electrodes 88 are electrically connected to the fourth electrode connector 88a disposed in parallel with the third electrode connector 86a. The fourth electrode connector 88a is connected to the cable 28 extended from the handle 22 via the fourth electrode energization line 88b. Moreover, the second discrete electrodes 88 are connected to the second high-frequency energy output circuit 106 of the energy source 14 described later.

It is to be noted that the cutter guide grooves 62a and 64a of the first and second holding members 62 and 64 are formed so as to face each other, and are formed along the axial direction of the shaft 24. Moreover, the one cutter 54 can be guided along the two cutter guide grooves 62a and 64a.

The cylindrical member 42 and the sheath 44 of the shaft 24 of the energy treatment instrument 12 shown in FIGS. 2A and 2B are provided with fluid discharge ports 42a and 44a through which a fluid such as vapor (a gas) or a liquid (a tissue liquid) described later is discharged. The fluid discharge ports 42a and 44a are formed in the proximal end of the shaft 24.

Here, although not shown, the outer peripheral surface of the fluid discharge port 44a of the sheath 44 is preferably provided with a connection mouthpiece. At this time, the fluid described later is discharged through the cutter guide grooves 62a and 64a, the fluid discharge port 42a of the cylindrical member 42 of the shaft 24, the fluid discharge port 44a of the sheath 44 of the shaft 24 and the connection mouthpiece. In this case, a fluid such as the vapor or the liquid discharged from the living tissue $L_T$ can easily be discharged through the fluid discharge ports 42a and 44a by sucking the fluid through the connection mouthpiece.

It is to be noted that the fluid discharge ports 42a and 44a are preferably provided in the shaft 24, but may preferably be provided in the handle 22 instead of the shaft 24.

The base portion 74 of the first holding member 62 is fixed to the distal end of the cylindrical member 42 of the shaft 24. On the other hand, the base portion 84 of the second holding member 64 is rotatably supported by the distal end of the cylindrical member 42 of the shaft 24 via a support pin 92 disposed in an orthogonal direction to the axial direction of the shaft 24. The second holding member 64 can rotate around the axis of the support pin 92 to open and close with respect to the first holding member 62. The second holding member 64 is urged by an elastic member 92a such as a leaf spring so as to open with respect to the first holding member 62.

The outer surfaces of the main bodies 72 and 82 of the first and second holding members 62 and 64 are formed into a smoothly curved shape. Similarly, the outer surfaces of the base portions 74 and 84 of the first and second holding members 62 and 64 are also formed into a smoothly curved shape. In a state where the second holding member 64 is closed with respect to the first holding member 62, the cross sections of the main bodies 72 and 82 of the respective holding members 62 and 64 are formed into a substantially circular or elliptic shape. In a state where the second holding member 64 is closed with respect to the first holding member 62, the holding faces 72b and 82b of the main bodies 72 and 82 of the first and second holding members 62 and 64 face each other, and the base portions 74 and 84 are formed into a cylindrical shape. In this state, the diameters of the proximal ends of the main bodies 72 and 82 of the first and second holding members 62 and 64 are formed to be larger than those of the base portions 74 and 84. Moreover, stepped portions 94a and 94b are formed between the main bodies 72, 82 and the base portions 74, 84, respectively.

Here, with regard to the first and second holding members 62, 64, in the state where the second holding member 64 is closed with respect to the first holding member 62, the outer peripheral surface of the substantially circular or elliptic shape obtained by combining the base portions 74 and 84 of the holding members is formed as substantially the same plane as the outer peripheral surface of the distal end of the cylindrical member 42 or formed with a diameter slightly larger than that of the outer peripheral surface. In consequence, the sheath 44 is slid with respect to the cylindrical member 42, whereby the distal end of the sheath 44 can cover the base portions 74 and 84 of the first holding member 62 and the second holding member 64. In this state, as shown in FIG. 2A, the first holding member 62 and the second holding member 64 close against the urging force of the elastic member 92a. On the other hand, when the sheath 44 is slid toward the proximal end of the cylindrical member 42 from the state where the distal end of the sheath 44 covers the base portions 74 and 84 of the first and second holding members 62 and 64, as shown in FIG. 2B, the second holding member 64 opens with respect to the first holding member 62 by the urging force of the elastic member 92a.

Moreover, in this embodiment, the sizes of a space between the proximal ends of the first continuous electrode 76 and a space between the proximal ends of the second continuous electrode 86 are approximately equal to the widths of the cutter guide grooves 62a and 64a of the first and second holding members 62 and 64, respectively (see FIG. 3A). However, the space between the proximal ends of the first continuous electrode 76 and the space between the proximal ends of the second continuous electrode 86 can appropriately be set, respectively. That is, the first and second continuous electrodes 76 and 86 may be provided away from the edges of the cutter guide grooves 62a and 64a of the first and second holding members 62 and 64.

As shown in FIG. 4, the energy source 14 includes a control section 102, the first high-frequency energy output circuit (a first control portion) 104, the second high-frequency energy output circuit (a second control portion) 106, the temperature measurement circuit 108, a display section 110 and a speaker 112 therein. The control section 102 is connected to the first and second high-frequency energy output circuit 104 and 106, the temperature measurement circuit 108, the display section 110 and the speaker 112, and the control section 102 controls these components. The control section 102 is connected to the foot switch 16. When the foot switch 16 is switched on (the pedal 16a is pressed), the energy treatment instrument 12 performs a treatment. When the switch is switched off (the pressed pedal 16a is released), the treatment stops. The display section 110 functions as setting means (a controller) in a case where the control section 102 controls the output amounts of the first and second high-frequency energy output circuit 104 and 106 (the output amounts themselves, or the treatment to be performed (a treatment for a purpose of joining the living tissues to each other, a treatment for a purpose of closing the opening of the living tissue or the like)), the display of the temperatures detected by the temperature sensors 80, or the output timing of the energy. Needless to say, the display section 110 has a display function of displaying the setting (various set values, etc.).

It is to be noted that the first high-frequency energy output circuit 104 outputs the high-frequency energy through the first and second continuous electrodes 76 and 86, and can detect an impedance Z of the living tissue between the first continuous electrode 76 and the second continuous electrode 86. The second high-frequency energy output circuit 106 outputs the high-frequency energy through the first and second discrete electrodes 78 and 88, and can detect the impedance Z of the living tissue between the first and second discrete electrodes 78 and 88. That is, the first high-frequency energy output circuit 104 and the first and second continuous electrodes 76 and 86 have a sensor function of measuring the impedance Z of the living tissue $L_T$ between the first and second continuous electrodes 76 and 86. The second high-frequency energy output circuit 106 and the first and second discrete electrodes 78 and 88 have a sensor function of measuring the impedance Z of the living tissue $L_T$ between the first and second discrete electrodes 78 and 88. It is to be noted that the temperature measurement circuit 108 and the temperature sensors 80 have a sensor function of measuring the temperatures.

Next, the operation of the treatment system 10 according to this embodiment will be described.

Figure 5:
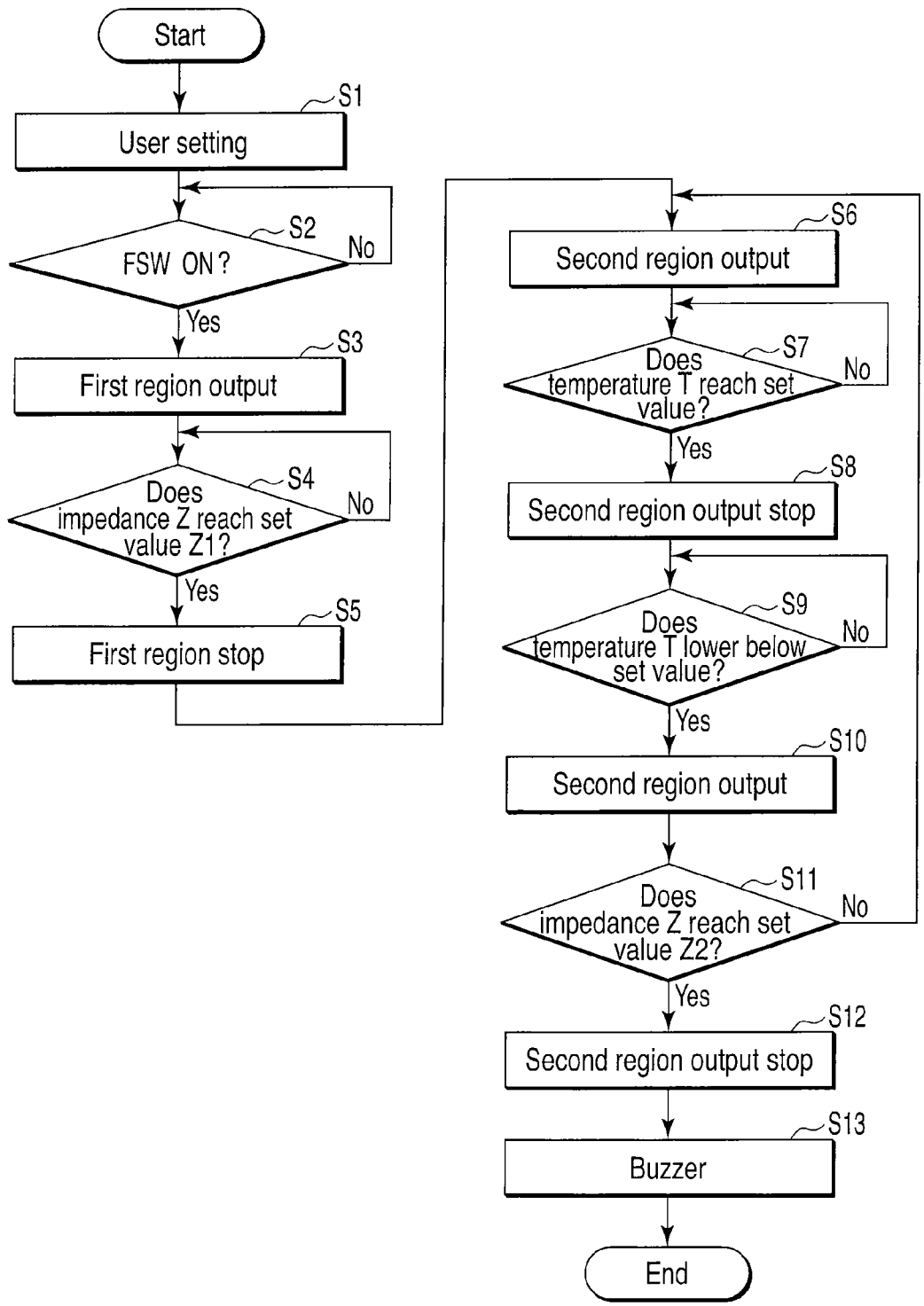
FIG. 5 is a schematic flow chart showing that a treatment using the high-frequency energy is performed with respect to the living tissue by use of the treatment system according to the first embodiment.

FIG. 5 shows one example of a control flow of the surgical treatment instrument 12 by the first and second high-frequency energy output circuits 104 and 106. FIG. 6A is a graph showing a relation between the output from the first high-frequency energy output circuit 104 and a time, and showing a relation between the output from the second high-frequency energy output circuit 106 and the time. FIG. 6B schematically shows, with respect to the time, the variance of the impedance Z usually measured when the energy is input as shown in FIG. 6A.

The operator beforehand operates the display section 110 of the energy source 14 to set the output conditions of the treatment system 10 (STEP 1). Specifically, the operator beforehand sets outputs (set powers P1set[W] and P2set[W]) from the first high-frequency energy output circuit 104 and the second high-frequency energy output circuit 106, threshold values Z1 and Z2 of the impedance Z of the living tissue $L_T$, a threshold value T1 of the temperature T described later and the like.

As shown in FIG. 2A, in the state where the second holding member 64 is closed with respect to the first holding member 62, the holding section 26 and the shaft 24 of the surgical treatment instrument 12 are inserted into, for example, an abdominal cavity through an abdominal wall. The holding section 26 of the surgical treatment instrument 12 is held so as to face the living tissue $L_T$ as a treatment target.

The holding section opening/closing knob 32 of the handle 22 is operated to hold the living tissue $L_T$ as the treatment target by the first and second holding members 62 and 64. At this time, the sheath 44 is moved toward the proximal end of the shaft 24 with respect to the cylindrical member 42. The cylindrical shape between the base portions 74 and 84 cannot be kept by the urging force of the elastic member 92a, and the second holding member 64 opens with respect to the first holding member 62.

The living tissue $L_T$ as the treatment target is disposed between the first and second continuous electrodes 76 and 86 of the first and second holding members 62 and 64 and between the first and second discrete electrodes 78 and 88 of the first and second holding members 62 and 64. In this state, the holding section opening/closing knob 32 of the handle 22 is operated. At this time, the sheath 44 is moved toward the distal end of the shaft 24 with respect to the cylindrical member 42. The base portions 74 and 84 are closed against the urging force of the elastic member 92a by the sheath 44 to obtain the cylindrical shape. In consequence, the main body 72 of the first holding member 62 integrally formed with the base portion 74 and the main body 82 of the second holding member 64 integrally formed with the base portion 84 are closed. That is, the second holding member 64 closes with respect to the first holding member 62. In this way, the living tissue $L_T$ as the treatment target is grasped between the first and second holding members 62 and 64.

At this time, the living tissue $L_T$ as the treatment target comes in contact with both the first and second continuous electrodes 76 and 86 of the first and second holding members 62 and 64. The living tissue $L_T$ as the treatment target comes in contact with both the first and second discrete electrodes 78 and 88 of the first and second holding members 62 and 64. The peripheral tissue of the living tissue $L_T$ as the treatment target comes in close contact with both facing contact faces of the edges of the holding faces 72b and 82b of the first and second holding members 62 and 64.

In this way, the pedal 16a of the foot switch 16 is operated in the state where the living tissue is grasped between the first and second holding members 62 and 64. The control section 102 of the energy source 14 judges whether or not the pedal 16a of the switch 16 has been pressed to switch on by the operation of the operator (STEP 2).

When it is judged that the pedal 16a of the foot switch 16 has been pressed to switch on, the high-frequency energy is supplied from the first high-frequency energy output circuit 104 of the energy source 14 to the living tissue (the living tissue of a first region) $L_T$ between the first and second continuous electrodes 76 and 86 (STEP 3).

Subsequently, the first high-frequency energy output circuit 104 supplies the set power P1set[W] preset by the display section 110, e.g., a power of about 20 [W] to 80 [W] between the first and second continuous electrodes 76 and 86 of the first and second holding members 62 and 64.

In consequence, the first high-frequency energy output circuit 104 supplies a high-frequency current to the living tissue $L_T$ as the treatment target between the first and second continuous electrodes 76 and 86 of the first and second holding members 62 and 64. That is, the high-frequency energy is supplied to the living tissue $L_T$ grasped between the electrodes 76 and 86. Therefore, Joule heat is generated in the living tissue $L_T$ grasped between the electrodes 76 and 86 to heat the living tissue $L_T$ itself. A cell membrane in the living tissue $L_T$ held between the electrodes 76 and 86 is broken by the function of the Joule heat to release substances from the cell membrane, and the tissue is homogenized with extracellular components including collagen. The high-frequency current is supplied through the living tissue $L_T$ between the electrodes 76 and 86, so that further Joule heat acts on the tissue $L_T$ homogenized in this manner, and, for example, the joining faces of the living tissue $L_T$ or the layers of the tissue are joined to each other. Therefore, when the high-frequency current is supplied between the electrodes 76 and 86, the living tissue $L_T$ itself generates the heat and is dehydrated, while the inside of the living tissue $L_T$ is denatured (the living tissue $L_T$ is cauterized). In consequence, the living tissue $L_T$ is continuously denatured (in a substantially U-shape) by the first and second continuous electrodes 76 and 86.

At this time, the impedance Z of the grasped living tissue $L_T$ is measured by the high-frequency energy output circuit 104 via the first and second continuous electrodes 76 and 86. An impedance Z0 at the start of the treatment is, for example, about 60 [Ω] as shown in FIG. 6B. Subsequently, when the high-frequency current flows through the living tissue $L_T$ to cauterize the living tissue $L_T$, the value of the impedance Z rises.

In this way, the fluid (e.g., the liquid (blood) and/or the gas (water vapor)) is discharged from the living tissue $L_T$ as the living tissue is cauterized. At this time, the holding faces 72b and 82b of the first and second holding members 62 and 64 come into closer contact with the living tissue $L_T$ than the first and second continuous electrodes 76 and 86. Therefore, the holding faces 72b and 82b function as barrier portions (dams) which inhibit the fluid from escaping to the outside from the first and second holding members 62 and 64. Therefore, the fluid discharged from the living tissue $L_T$ is caused to flow into the cutter guide groove 62a inside the first continuous electrode 76 and the cutter guide groove 64a inside the second continuous electrode 86, and is, for example, sucked to flow from the first and second holding members 62 and 64 into the shaft 24. While the fluid is discharged from the living tissue $L_T$, the fluid continues to flow into the cutter guide grooves 62a and 64a. This prevents thermal spread from being caused by the fluid discharged from the living tissue $L_T$ in a state where the temperature rises, and accordingly, can prevent a portion other than the treatment target from being influenced.

Subsequently, the control section 102 judges whether or not the impedance Z during the high-frequency energy output calculated based on a signal from the high-frequency energy output circuit 104 exceeds a threshold value Z1 (here, about 1000 [Ω] as shown in FIG. 6B) set beforehand (STEP 1) by the display section 110 (STEP 4). The threshold value Z1 is set to such a value that the rise ratio of the beforehand known value of the impedance Z lowers. Subsequently, when it is judged that the impedance Z is smaller than the threshold value Z1, processing is returned to STEP 3. That is, the high-frequency energy for the treatment is continuously applied to the living tissue $L_T$ grasped between the first and second continuous electrodes 76 and 86 of the first and second holding members 62 and 64.

When it is judged that the impedance Z becomes larger than the threshold value Z1, the control section 102 transmits the signal to the first high-frequency energy output circuit 104. Then, the output from the first high-frequency energy output circuit 104 to the first and second continuous electrodes 76 and 86 is stopped (STEP 5).

Next, the second high-frequency energy output circuit 106 of the energy source 14 supplies energy to the living tissue (the living tissue of a second region) $L_T$ between the first and second discrete electrodes 78 and 88 (STEP 6). That is, the second high-frequency energy output circuit 106 supplies the energy to the living tissue $L_T$ between the first and second discrete electrodes 78 and 88 in a state temporally offset from the time when the first high-frequency energy output circuit 104 supplies the energy to the living tissue $L_T$ between the first and second continuous electrodes 76 and 86 (in a state where an output timing is offset).

Subsequently, the second high-frequency energy output circuit 106 supplies the set power P2set[W] beforehand set by the display section 110, e.g., a power of about 20 [W] to 80 [W] between the first and second discrete electrodes 78 and 88 of the first and second holding members 62 and 64. It is to be noted that the output from the second high-frequency energy output circuit 106 to the first and second discrete electrodes 78 and 88 may be larger or smaller than that from the first high-frequency energy output circuit 104 to the first and second continuous electrodes 76 and 86. Such an output largeness is appropriately set in accordance with the treatment target, the purpose or the like before the treatment (STEP 1).

In consequence, the high-frequency current flows through the living tissue $L_T$ grasped between the first and second holding members 62 and 64, and the heat is generated from the living tissue $L_T$ by the function of the Joule heat to start the cauterization of the tissue (the denaturalization of the tissue). In this case, the living tissue $L_T$ between the first and second discrete electrodes 78 and 88 is discretely denatured by the electrodes 78 and 88. At this time, the impedance Z of the grasped living tissue $L_T$ is measured by the second high-frequency energy output circuit 106 via the first and second discrete electrodes 78 and 88. As to the impedance Z at the start of the treatment, since the living tissue $L_T$ is not denatured, the threshold value Z1 of FIG. 6B can be replaced with a threshold value Z2, and the first impedance Z is, for example, Z0. Moreover, when the high-frequency current flows through the living tissue $L_T$ to cauterize the living tissue $L_T$, the value of the impedance Z rises.

Furthermore, after starting the output from the second high-frequency energy output circuit 106, preferably continuously from the output of the first high-frequency energy output circuit 104, the temperature T in the vicinity of the living tissue $L_T$ which abuts on the first discrete electrodes 78 continues to be measured by the temperature sensors 80 embedded in the main body 72 of the first holding member 62. Subsequently, it is judged whether or not the temperature T reaches a predetermined temperature T1 (STEP 7). When the temperature T1 is reached, the output to the second high-frequency energy output circuit 106 is stopped (STEP 8). It is then waited until the temperature T in the vicinity of the living tissue $L_T$ which abuts on the first discrete electrodes 78 falls below the temperature T1. When it is judged that the temperature T falls below the set temperature T1 (STEP 9), the energy is again supplied to the second high-frequency energy output circuit 106 (STEP 10). In this way, the temperature T1 is used as the threshold value, thereby automatically switching on/off the supply of the energy from the second high-frequency energy output circuit 106.

Subsequently, as the living tissue $L_T$ is cauterized, the fluid (e.g., the liquid (the blood) and/or the gas (the water vapor)) is discharged from the living tissue $L_T$. At this time, the holding faces 72b and 82b of the first and second holding members 62 and 64 have a higher degree of close contact with the living tissue $L_T$ than the first and second discrete electrodes 78 and 88. Therefore, the holding faces 72b and 82b function as the barrier portions (dams) which inhibit the fluid from escaping to the outside from the first and second holding members 62 and 64. Consequently, the fluid discharged from the living tissue $L_T$ is caused to flow into the cutter guide grooves 62a and 64a further inside the first continuous electrode 76 inside the first discrete electrodes 78 and further inside the second continuous electrode 86 inside the second discrete electrodes 88, and the fluid is, for example, sucked to flow from the first and second holding members 62 and 64 to the shaft 24. While the fluid is discharged form the living tissue $L_T$, the fluid continues to flow into the cutter guide grooves 62a and 64a. This can prevent the thermal spread from being caused by the fluid discharged from the living tissue $L_T$ in a state where the temperature is raised, and can prevent the portion which is not the treatment target from being influenced. At this time, since the output timings of the first and second high-frequency energy output circuit 104 and 106 are offset, the fluid can be supplied through the cutter guide grooves 62a and 64a in a state where mutual interference is prevented.

Next, the control section 102 judges whether or not the impedance Z during the high-frequency energy output calculated based on the signal from the second high-frequency energy output circuit 106 exceeds the preset threshold value Z2 (here, about 1000 [Ω] as shown in FIG. 6B) (STEP 11). The threshold value Z2 is preferably set to such a value that the rise ratio of the beforehand known value of the impedance Z lowers. Subsequently, when it is judged that the impedance Z is smaller than the threshold value Z2, the processing is returned to STEP 6. That is, while switching on/off in accordance with the temperature T1, the high-frequency energy for the treatment is applied to the living tissue $L_T$ grasped between the first and second discrete electrodes 78 and 88 of the first and second holding members 62 and 64.

When it is judged that the impedance Z becomes larger than the threshold value Z2, the control section 102 transmits the signal to the second high-frequency energy output circuit 106. Then, the output from the second high-frequency energy output circuit 106 to the first and second discrete electrodes 78 and 88 is stopped (STEP 12).

Subsequently, after stopping the output, a buzzer is sounded by the control section 102 via the speaker 112 (STEP 13). In consequence, it is possible to easily recognize the end of the treatment of the living tissue $L_T$ performed by the second high-frequency energy output circuit 106 through the first and second discrete electrodes 78 and 88.

It is to be noted that the treatment is performed from the "start" to the "end" shown in FIG. 5 while the pedal 16a of the foot switch 16 is pressed, but if the pressed pedal 16a is released between the "start" and the "end", the control section 102 forcibly stops the treatment upon releasing the pressed pedal 16a. That is, when the pressed pedal 16a is released, the control section 102 stops the outputs of both the first and second high-frequency energy output circuits 104 and 106.

Here, there will be described a case where, for example, intestinal canals $I_{C1}$ and $I_{C2}$ of a small intestine disposed side by side are joined to each other, and the joined intestinal canals $I_{C1}$ and $I_{C2}$ are sealed by use of the treatment system 10 having such a function as shown in FIGS. 7A to 7C.

The display section 110 of the energy source 14 is operated to beforehand set the outputs from the first and second high-frequency energy output circuits 104 and 106. At this time, the pair of intestinal canals $I_{C1}$ and $I_{C2}$ disposed side by side are to be first joined to each other, and hence the output from the second high-frequency energy output circuit 106 is preset to be appropriately high.

The holding faces 72b and 82b of the first and second holding members 62 and 64 hold the pair of intestinal canals $I_{C1}$ and $I_{C2}$ arranged side by side so as to sandwich the wall surfaces of both the intestinal canals $I_{C1}$ and $I_{C2}$ therebetween.

When the pedal 16a of the foot switch 16 is pressed in this state, the energy is supplied to the living tissue $L_T$ between the first and second continuous electrodes 76 and 86. In consequence, the intestinal canals $I_{C1}$ and $I_{C2}$ are heated and denatured by the first and second continuous electrodes 76 and 86.

Subsequently, when the living tissue $L_T$ between the first and second continuous electrodes 76 and 86 reaches the predetermined threshold value Z1, the output of the energy from the first high-frequency energy output circuit 104 is stopped.

Afterward, the energy is supplied to the living tissue $L_T$ between the first and second discrete electrodes 78 and 88. In consequence, the first and second discrete electrodes 78 and 88 heat and denature the intestinal canals $I_{C1}$ and $I_{C2}$.

Subsequently, when the temperature T reaches the predetermined temperature T1, the output is automatically stopped (OFF). When the temperature falls below the temperature T1, the energy is automatically output (ON). When the output is repeatedly switched on/off and the impedance Z of the living tissue between the first and second discrete electrodes 78 and 88 reaches the predetermined threshold value Z2, the output from the second high-frequency energy output circuit 106 is completely stopped.

It is to be noted that when the impedance Z of the living tissue $L_T$ between the first and second continuous electrodes 76 and 86 reaches the threshold value Z1, the intestinal canals $I_{C1}$ and $I_{C2}$ are heated, denatured and joined to each other by the first and second continuous electrodes 76 and 86. When the impedance Z of the living tissue $L_T$ between the first and second discrete electrodes 78 and 88 reaches the predetermined threshold value Z2, the intestinal canals $I_{C1}$ and $I_{C2}$ are heated, denatured and joined to each other by the first and second discrete electrodes 78 and 88. In this way, the intestinal canals $I_{C1}$ and $I_{C2}$ are continuously and discretely denatured and joined (anastomosed) to each other.

Subsequently, while the intestinal canals $I_{C1}$ and $I_{C2}$ are grasped between the first and second holding members 62 and 64, the cutter driving knob 34 shown in FIG. 1A is operated to move the cutter 54 forwards along the cutter guide grooves 62a and 64a from the state shown in FIGS. 2A and 2B. As the cutter 54 is moved forwards, the inside of a portion denatured and joined by the first and second continuous electrodes 76 and 86 is cut with the blade 54a at the distal end of the cutter. Subsequently, the inside of the substantially U-shaped portion denatured by the first and second continuous electrodes 76 and 86 is cut to the vicinity of the distal end of the portion with the cutter 54. In consequence, as shown in FIG. 7A, a portion between the substantially U-shaped sealed wall surfaces of the intestinal canals $I_{C1}$ and $I_{C2}$ is cut to connect the wall surfaces of the intestinal canals $I_{C1}$ and $I_{C2}$ each other.

The cutter driving knob 34 is operated in this state to move the cutter 54 backwards. Afterward, the holding section opening/closing knob 32 of the handle 22 is operated to open the first and second holding members 62 and 64. At this time, a first anastomosed portion $A_{N1}$ on a mesenterium M side and a second anastomosed portion $A_{N2}$ on a side opposite to the mesenterium M side are formed. As shown in, for example, FIG. 7B, the continuously joined outer portions of the first anastomosed portion $A_{N1}$ and the second anastomosed portion $A_{N2}$ are discretely denatured.

Subsequently, the display section 110 of the energy source 14 is again operated to set the output from the first high-frequency energy output circuit 104 to a high output in accordance with the treatment target (the intestinal canals $I_{C1}$ and $I_{C2}$ are sealed).

The first and second holding members 62 and 64 are closed to hold the ends of the intestinal canals $I_{C1}$ and $I_{C2}$. The pedal 16a of the foot switch 16 is pressed in this state to apply the energy from the first high-frequency energy output circuit 104 to the first and second continuous electrodes 76 and 86 until the impedance Z reaches the threshold value Z1. In consequence, the ends of the intestinal canals $I_{C1}$ and $I_{C2}$ are joined to each other by the first and second continuous electrodes 76 and 86 to form a seal portion Sp.

Consequently, as shown in FIG. 7C, the ends of the intestinal canals $I_{C1}$ and $I_{C2}$ are denatured and sealed by the first and second continuous electrodes 76 and 86. That is, the ends of the intestinal canals $I_{C1}$ and $I_{C2}$ are provided with the seal portion Sp. At this time, the cross section cut along the 7A-7A line of FIG. 7C schematically has the state shown in FIG. 7A. In consequence, the intestinal canals $I_{C1}$ and $I_{C2}$ having the ends thereof sealed with the seal portion Sp are anastomosed with each other.

Afterward, the energy is applied from the second high-frequency energy output circuit 106 to the first and second discrete electrodes 78 and 88 until the impedance Z reaches the threshold value Z2. At this time, as described above, when the temperature T reaches the threshold value T1, the output is stopped (OFF). When the temperature falls below the threshold value T1, the energy is output (ON), and the ends of the intestinal canals $I_{C1}$ and $I_{C2}$ are joined to each other by the first and second discrete electrodes 78 and 88. Subsequently, when the impedance Z reaches the threshold value Z2, the output from the second high-frequency energy output circuit 106 is stopped.

It is to be noted that the extra portion of the seal portion Sp is cut with, for example, the cutter 54. At this time, the continuously joined peripheral portion of the sealed end (the seal portion Sp) of the intestinal canals $I_{C1}$ and $I_{C2}$ is discretely denatured in the same manner as shown in FIG. 7B. That is, the living tissue between the portions of the intestinal canals $I_{C1}$ and $I_{C2}$ denatured and joined by the first and second discrete electrodes 78 and 88 is not denatured. Therefore, the periphery (the vicinity) of the portion of the living tissue joined by the first and second discrete electrodes 78 and 88 comes in (close) contact with the living tissues of the intestinal canals $I_{C1}$ and $I_{C2}$ which are not denatured.

Therefore, at the first anastomosed portion $A_{N1}$ on the mesenterium M side, a force is exerted in a direction in which the intestinal canals $I_{C1}$ and $I_{C2}$ come in close contact with each other. In this case, the portion of the living tissue denatured by the first and second discrete electrodes 78 and 88 exerts such a force that the living tissues more firmly come in close contact with each other. Furthermore, at the second anastomosed portion $A_{N2}$ on the side opposite to the mesenterium M side, a force $F_1$ is exerted in a direction in which the intestinal canals $I_{C1}$ and $I_{C2}$ open, but the portion of the living tissue denatured by the first and second discrete electrodes 78 and 88 exerts such a force that the living tissues come in close contact with each other. Therefore, the mutual network of the living tissues of the intestinal canals $I_{C1}$ and $I_{C2}$ which are not denatured is generated, and the tissue regenerative force of the living tissue is exerted, whereby the living tissues of the intestinal canals $I_{C1}$ and $I_{C2}$ are regenerated earlier.

As described above, according to this embodiment, the following effect is obtained.

The first continuous electrode 76 and the first discrete electrodes 78 are separately arranged on the first holding member 62, and the second continuous electrode 86 and the second discrete electrodes 88 are separately arranged on the second holding member 64. Therefore, it is possible to separately set the output from the first high-frequency energy output circuit 104 to the first and second continuous electrodes 76 and 86 and the output from the second high-frequency energy output circuit 106 to the first and second discrete electrodes 78 and 88. Subsequently, after stopping the output from the first high-frequency energy output circuit 104, the energy is output from the second high-frequency energy output circuit 106 to treat the living tissue $L_T$. That is, since the output timing is offset, it is possible to prevent interference between the fluid generated from the first and second continuous electrodes 76 and 86 by the output from the first high-frequency energy output circuit 104 and the fluid generated from the first and second discrete electrodes 78 and 88 by the output from the second high-frequency energy output circuit 106. In consequence, the fluid generated by the treatment of the living tissue $L_T$ can securely be guided to the cutter guide grooves 62a and 64a.

Moreover, the respective outputs from the first high-frequency energy output circuit 104 and the second high-frequency energy output circuit 106 can be set for each treatment, so that various treatments can easily be performed, and the versatility of the treatment can be broadened. That is, the surgical treatment instrument 12 can optimally be set in accordance with various use applications, to perform the treatment, merely by operating the display section 110 to change the settings thereof.

As described above, the first continuous electrode 76 and the first discrete electrodes 78 are arranged on the holding face 72b of the first holding member 62, and the second continuous electrode 86 and the second discrete electrodes 88 are arranged on the holding face 82b of the second holding member 64. In consequence, the living tissues (e.g., the intestinal canals $I_{C1}$ and $I_{C2}$) between the first continuous electrode 76 of the first holding member 62 and the second continuous electrode 86 of the second holding member 64 can be heated, denatured and continuously joined to each other. Therefore, when, for example, tubular living tissues are joined to each other, the output from the second high-frequency energy output circuit 106 is increased. When the living tissues are sealed to each other, the output from the first high-frequency energy output circuit 104 is increased. Thus, the treatment can be performed in an optimum state.

At this time, as shown in, for example, FIG. 7B, portions of the living tissues continuously denatured and joined to each other are positioned close to portions of the living tissues discretely denatured and joined to each other. Then, a portion which is not denatured is present between the living tissues around the portions of the living tissues discretely denatured and joined to each other. In consequence, it is possible to maintain a state where the living tissues which are not denatured around the discretely denatured and joined portions are brought into (close) contact with each other. That is, the first and second discrete electrodes 78 and 88 perform an important role in maintaining the close contact state of the living tissues to which the force $F_1$ having, for example, such a direction that the tissues come away from each other is applied.

In a case where, for example, two intestinal canals $I_{C1}$ and $I_{C2}$ are anastomosed with each other, the force $F_1$ is exerted in a direction in which the intestinal canals $I_{C1}$ and $I_{C2}$ come away from each other on the side opposite to the mesenterium M side shown in FIGS. 7A and 7C. However, the intestinal canals $I_{C1}$ and $I_{C2}$ are discretely joined to each other by the first and second discrete electrodes 78 and 88, so that the intestinal canals $I_{C1}$ and $I_{C2}$ can discretely be joined to each other. Therefore, the mutual close contact state of the intestinal canals $I_{C1}$ and $I_{C2}$ can be maintained.

Therefore, the portions of the living tissues joined to each other by the first and second discrete electrodes 78 and 88 perform a function of maintaining a state where the living tissues are drawn to each other and brought into close contact with each other. That is, the portions of the living tissues joined to each other by the first and second discrete electrodes 78 and 88 perform a function of maintaining the conglutination of the living tissues. Therefore, the mutual network of the living tissues brought into close contact (conglutinated) with each other is generated, and the tissue regenerative force of the living tissue is more easily exerted, whereby the living tissue can be regenerated earlier.

It is to be noted that in this embodiment, it has been described that the first discrete electrodes 78 of the first holding member 62 are arranged at substantially equal intervals, and have a substantially equal area, but the space between the adjacent discrete electrodes 78 preferably varies, and the areas of the discrete electrodes 78 preferably vary, respectively. When the tissues are discretely treated by the discrete electrodes 78, the portions which come in contact with the discrete electrodes 78 are denatured. However, the discrete electrodes 78 may variously be modified as long as it is possible to maintain a state where a part of the living tissue between the discrete electrode 78 and the discrete electrode 78 adjacent to the former discrete electrode 78 is not denatured and the living tissues are brought into contact with each other. Needless to say, this also applies to the second discrete electrodes 88 of the second holding member 64.

Moreover, the plurality of first and second discrete electrodes 78 and 88 of the first and second holding members 62 and 64 may preferably be replaced with heaters (heat generation elements), or the first and second continuous electrodes 76 and 86 of the first and second holding members 62 and 64 may preferably be replaced with heaters (heat generation elements). Moreover, the plurality of first and second discrete electrodes 78 and 88, and the first and second continuous electrodes 76 and 86 of the first and second holding members 62 and 64 may preferably all be replaced with the heaters. Furthermore, the heaters may be arranged on the back surfaces of the electrodes to conduct the heat from the heaters to the electrodes, thereby treating the living tissue with the high-frequency energy and heat energy. The heaters are arranged instead of, for example, the temperature sensors 80 shown in FIG. 3D. When the heaters are used, for example, the first high-frequency energy output circuit 104 of the energy source 14 is also used as a circuit for applying the energy to the heaters.

Moreover, in this embodiment, a case where the cutter 54 is provided has been described, but the cutter 54 does not have to be provided, depending on the treatment target. When the cutter 54 is not provided, the cutter guide grooves 62a and 64a can function as fluid discharge grooves (channels) which guide a fluid such as vapor or a liquid generated from the living tissue to the handle 22 side of the energy treatment instrument 12.

Here, it has been described that as shown in FIG. 1B, the bipolar type surgical treatment instrument 12 including the electrodes provided on the first and second holding members 62 and 64 and having different potentials (a potential between the first continuous electrode 76 and the second continuous electrode 86 and a potential between the first and second discrete electrodes 78 and 88) is used for performing the high-frequency energy treatment. However, as shown in FIG. 3E, a monopolar type surgical treatment instrument for performing the high-frequency energy treatment may preferably be used. In this case, a return electrode plate 130 is attached to a patient P to be treated. This return electrode plate 130 is connected to the energy source 14 via an energization line 132. Furthermore, the first continuous electrode 76 of the first holding member 62 is electrically connected to the second continuous electrode 86 of the second holding member 64 via the first electrode energization line 76b and the third electrode energization line 86b in an equal potential state. Moreover, the first discrete electrodes 78 of the first holding member 62 are electrically connected to the second discrete electrodes 88 of the second holding member 64 via the second electrode energization line 78b and the fourth electrode energization line 88b in the equal potential state. In these cases, the areas of the living tissue $L_T$ which come in contact with the continuous electrodes 76 and 86 and the discrete electrodes 78 and 88 are small, respectively, so that a current density is high, but the current density of the return electrode plate 130 lowers. Therefore, the living tissue $L_T$ grasped between the first and second holding members 62 and 64 is heated, whereas the living tissue $L_T$ which comes in contact with the return electrode plate 130 is heated less to a negligible degree. Therefore, the only portions of the living tissue $L_T$ that are grasped between the first and second holding members 62 and 64 and that come in contact with the continuous electrodes 76 and 86 and the discrete electrodes 78 and 88 are heated and denatured.

Moreover, although not shown, the electrodes may preferably be arranged on only one of the first and second holding members 62 and 64 in a case where the monopolar type surgical treatment instrument is used.

Furthermore, in this embodiment, the use of the two high-frequency energy output circuits 104 and 106 has been described, but the number of the circuits is not limited to two, and three, four or more circuits may appropriately be used in accordance with the treatment. That is, in the treatment, setting can be performed with the display section 110, and the optimization of the treatment can be achieved.

In this embodiment, the energy is output as shown in FIG. 6A, but as shown in FIG. 6C, the output from the second high-frequency energy output circuit 106 may be increased as compared with the output from the first high-frequency energy output circuit 104 to shorten the treatment time by causing the impedance Z to reach the threshold value Z2 early while shortening the time to reach the predetermined temperature T1.

Moreover, as shown in FIG. 6D, the first high-frequency energy output circuit 104 and the second high-frequency energy output circuit 106 preferably alternately output the energy in a state where the output timing is offset. Furthermore, the constitution in which the impedances Z1 and Z2 and the set powers P1set and P2set are set by the operator has been described, but proper values may be programmed beforehand.

[First Modification of First Embodiment]

Next, a first modification of the first embodiment will be described with reference to FIGS. 8A and 8B. The description of the same members as those described in the first embodiment or members performing the same function as those of the first embodiment is omitted. This hereinafter applies to second to fourth modifications.

Figure 8A:
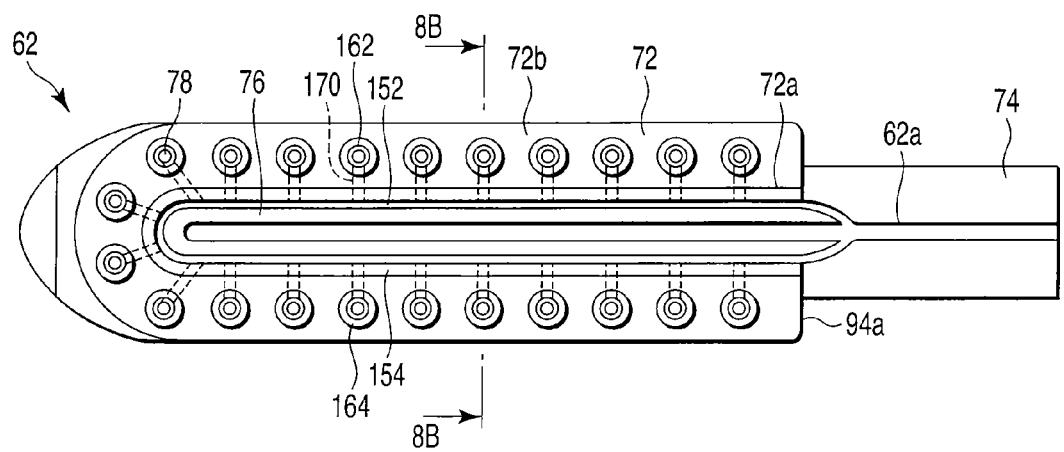
FIG. 8A is a schematic plan view showing a first holding member on a side close to a second holding member in a holding section of an energy treatment instrument of a treatment system according to a first modification of the first embodiment.

As shown in FIG. 8A, a first continuous and discrete electrodes 76 and 78 are arranged at substantially the same positions as those of the first embodiment shown in FIG. 3A.

Figure 8B:
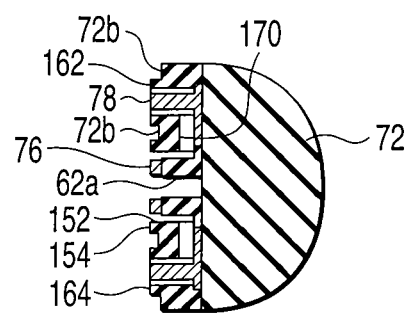
FIG. 8B is a schematic transverse sectional view cut along the 8B-8B line of FIG. 8A and showing the first holding member in the holding section of the energy treatment instrument of the treatment system according to the first modification of the first embodiment.

As shown in FIGS. 8A and 8B, outside the first continuous electrode 76, a main body 72 of a first holding member 62 is provided with a first fluid discharge groove (a continuous electrode fluid discharge groove) 152 as a channel of a fluid such as vapor or high-temperature liquid. Outside the first fluid discharge groove 152, a continuous electrode barrier portion (a dam) 154 is formed so that a fluid such as the vapor or the high-temperature liquid discharged by the function of the first continuous electrode 76 enters the first fluid discharge groove 152. As shown in FIG. 8B, the barrier portion 154 is projected from the flat surface of a holding face 72b.

In the outer periphery of each of the first discrete electrodes 78 of the main body 72, a second fluid discharge groove (a discrete electrode fluid discharge groove) 162 is formed as a channel of a fluid such as the vapor or the high-temperature liquid. On the outer periphery of the second fluid discharge groove 162, a barrier portion 164 for the discrete electrode is formed so that a fluid such as the vapor or the high-temperature liquid discharged by the function of the first discrete electrodes 78 enters the second fluid discharge groove 162. As shown in FIG. 8B, the barrier portion 164 is projected from the flat surface of the holding face 72b.

The first and second discharge grooves 152 and 162 are connected by communication paths 170. The communication paths 170 is formed as a conduit. That is, the communication path 170 is formed in the main body 72. Moreover, the communication path 170 is connected to a cutter guide groove 62a via a base portion 74. That is, the first and second fluid discharge grooves 152 and 162 are connected to the cutter guide groove 62a via the base portion 74.

It is to be noted that in the same manner as in a second holding member 64, a fluid discharge groove (conveniently denoted with reference numeral 172) is formed outside a second continuous electrode 86, and a barrier portion (conveniently denoted with reference numeral 174) is formed outside the fluid discharge groove 172. Moreover, a fluid discharge groove (conveniently denoted with reference numeral 182) is formed in the outer periphery of each second discrete electrode 88 of the second holding member 64, and a barrier portion (conveniently denoted with reference numeral 184) is formed on the outer periphery of the fluid discharge groove 182. Moreover, the fluid discharge groove 172 outside the second continuous electrode 86 is connected to the fluid discharge groove 182 in the outer periphery of the second discrete electrode 88 via a communication path (conveniently denoted with reference numeral 190).

Next, the schematic operation of a treatment system 10 according to this modification will be described.

As described in the first embodiment, a living tissue $L_T$ as a treatment target is held between the first and second holding members 62 and 64. At this time, the barrier portions 154 and 164 of the main body 72 of the first holding member 62 and the barrier portions 174 and 184 of a main body 82 of the second holding member 64 come in close contact with the living tissue $L_T$, and the living tissue $L_T$ comes in contact with the first and second continuous electrodes 76 and 86, and the first and second discrete electrodes 78 and 88.

A pedal 16a of a foot switch 16 is operated in this state. Energy is supplied from an energy source 14 to the first and second continuous electrodes 76 and 86. Then, the living tissue $L_T$ between the first and second continuous electrodes 76 and 86 is heated by high-frequency energy. At this time, a fluid such as vapor or a liquid is discharged from, for example, the heated portion of the living tissue $L_T$.

Here, the first fluid discharge groove 152 of the main body 72 of the first holding member 62 is disposed outside the first continuous electrode 76, and the second fluid discharge grooves 162 are arranged in the outer peripheries of the first discrete electrodes 78. The first fluid discharge groove 172 of the main body 82 of the second holding member 64 is disposed outside the second continuous electrode 86, and the second fluid discharge grooves 182 are arranged in the outer peripheries of the second discrete electrodes 88.

In consequence, the fluid discharged owing to the functions of the first and second continuous electrodes 76 and 86 flows into the cutter guide groove 62a and 64a, and also flows into the first and second fluid discharge grooves 152 and 172. Then, the fluid is prevented from flowing out by the barrier portions 154 and 174. Therefore, the fluid discharged from the living tissue $L_T$ is kept internally from the barrier portions 154 and 174, and is prevented from escaping to the outside. That is, the barrier portions 154 and 174 function as dams which prevent the fluid discharged from the living tissue $L_T$ from leaking to the outside of the barrier portions 154 and 174.

Moreover, the fluid is discharged to the outside of a surgical treatment instrument 12 via a fluid discharge port 44a of a sheath 44 through a fluid discharge port 42a of a cylindrical member 42 of a shaft 24.

After a treatment by use of the first and second continuous electrodes 76 and 86, the energy is supplied to the first and second discrete electrodes 78 and 88 in a state where an output timing is offset to the treatment by use of the first and second continuous electrodes 76 and 86.

The living tissue $L_T$ between the first and second discrete electrodes 78 and 88 is heated by the high-frequency energy. At this time, a fluid such as the vapor or the liquid is discharged from, for example, the heated portion of the living tissue $L_T$.

The fluid discharged by the functions of the first and second discrete electrodes 78 and 88 flows into the second fluid discharge grooves 162 and 182. Then, the fluid is prevented from flowing out by the barrier portions 164 and 184. In consequence, the fluid discharged from the living tissue $L_T$ is kept internally from the barrier portions 164 and 184, and is prevented from escaping to the outside. That is, the barrier portions 164 and 184 function as dams which prevent the fluid discharged from the living tissue $L_T$ from leaking to the outside from the barrier portions 164 and 184.

The fluid which has flowed into the second fluid discharge grooves 162 and 182 flows into the first fluid discharge grooves 152 and 172 through the communication paths 170 and 190. Then, this fluid flows toward the base portion 74 of the first holding member 62 and the base portion 84 of the second holding member 64. Furthermore, the fluid flows into the cutter guide grooves 62a and 64a connected to the first fluid discharge grooves 152 and 172 in, for example, the base portions 74 and 84. The first fluid discharge grooves 152 and 172 are connected inside the cylindrical member 42 of the shaft 24 (not shown).

Then, the fluid is discharged to the outside of the surgical treatment instrument 12 via the fluid discharge port 44a of the sheath 44 through the fluid discharge port 42a of the cylindrical member 42 of the shaft 24.

As described above, according to this modification, the following effect is obtained. The description of an effect similar to that described in the first embodiment is omitted.

When a high-frequency current is applied to the living tissue $L_T$ as the treatment target held by a holding section 26 of the surgical treatment instrument 12, the barrier portions 154, 164, 174 and 184 are brought into close contact with the living tissue, whereby even when the fluid discharged from the living tissue $L_T$ as the treatment target flows toward the barrier portions 154 and 164 of the first holding member 62 and the barrier portions 174 and 184 of the second holding member 64, the fluid can be introduced into the first and second fluid discharge grooves 152 and 162 of the first holding member 62, the first and second fluid discharge grooves 172 and 182 of the second holding member 64 and the communication paths 170 and 190.

In consequence, the peripheral tissue can be prevented from being influenced by the fluid discharged from the portions treated by the high-frequency energy during the treatment of the living tissue $L_T$. That is, a part influenced during the treatment of the living tissue $L_T$ can be limited to the living tissue $L_T$ to which the high-frequency current is supplied between the first and second continuous electrodes 76 and 86, and between the first and second discrete electrodes 78 and 88.

Moreover, the outflow timing of the fluid generated from the living tissue $L_T$ between the first and second continuous electrodes 76 and 86 is shifted from that of the fluid generated from the living tissue $L_T$ between the first and second discrete electrodes 78 and 88. This can prevent the fluids from interfering with each other in fluid channels (the first and second fluid discharge grooves 152, 162, 172 and 182 and the communication paths 170 and 190).

Therefore, according to this modification, a fluid such as the vapor or liquid (a high-temperature body fluid) generated from the living tissue $L_T$ is discharged to the outside of the surgical treatment instrument 12 on the side of, for example, the proximal end of the shaft 24 or a handle 22, whereby a living tissue around the living tissue $L_T$ as the treatment target can be inhibited from being influenced by a fluid such as the vapor or liquid (the body fluid).

Thus, it is important to guide a fluid such as the vapor or liquid to a position which does not come in contact with the tissue so that the thermal influence on the living tissue $L_T$ is suppressed. In the case of the treatment of a tissue which is larger than the holding section 26 to such an extent that the periphery of the holding section 26 is covered, the outside of the holding section 26 can be prevented from being thermally influenced. In a case where even a small open portion (space) through which a fluid such as the vapor or liquid leaks is formed in the holding section 26, the fluid is discharged from the portion to thermally influence the living tissue $L_T$ around the holding section 26.

Moreover, even when the peripheries of the electrodes (energy release portions) 76, 78, 86 and 88 are covered with the barrier portions 154, 164, 174 and 184 to eliminate such an open portion, an open portion might be formed by a fluid pressure such as a vapor pressure generated from the living tissue $L_T$, and the fluid might be discharged. Therefore, it is a useful means to provide channels (the first and second fluid discharge grooves 152, 162, 172 and 182 and the communication paths 170 and 190) which suppress the discharge of the unnecessary fluid due to the rise of the fluid pressure and which guide and discharge the fluid in a predetermined direction.

[Second Modification of First Embodiment]

Next, a second modification of the first embodiment will be described with reference to FIG. 8C.

Figure 8C:
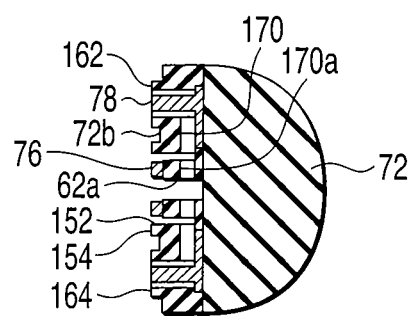
FIG. 8C is a schematic transverse sectional view cut along the 8B-8B line of FIG. 8A and showing a modification of a first holding member in a holding section of an energy treatment instrument of a treatment system according to a second modification of the first embodiment.

As shown in FIG. 8C, a communication path 170 (hereinafter referred to as the first communication path) is formed as a conduit. The first communication path 170 is provided with a tubular second communication path 170a also connected to a cutter guide groove 62a in a main body 72.

In this way, a fluid generated from a living tissue $L_T$ can be passed through the tubular first and second communication paths 170 and 170a to prevent, for example, the fluid which might have a high temperature from being brought into contact with the living tissue $L_T$ as much as possible.

[Third Modification of First Embodiment]

Next, a third modification of the first embodiment will be described with reference to FIGS. 9A to 12B.

Figure 9A:
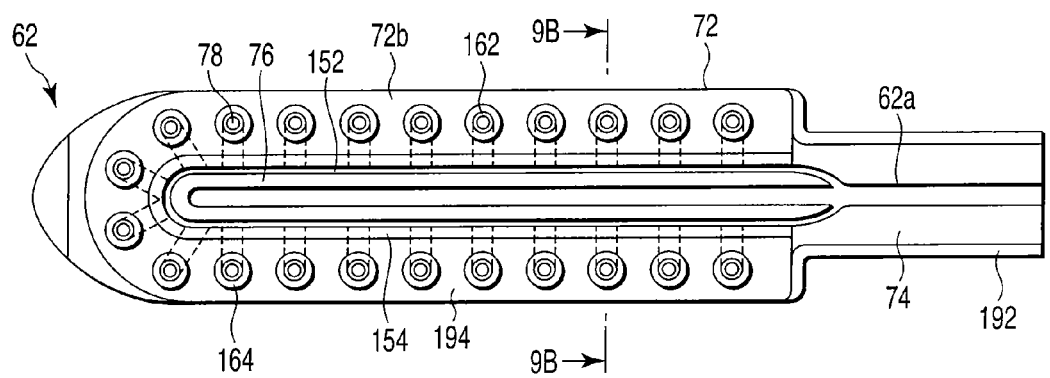
FIG. 9A is a schematic plan view showing a first holding member on a side close to a second holding member in a holding section of an energy treatment instrument of a treatment system according to a third modification of the first embodiment.
Figure 9B:
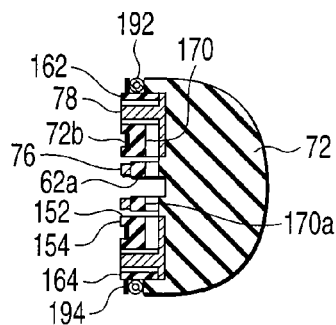
FIG. 9B is a schematic transverse sectional view cut along the 9B-9B line of FIG. 9A and showing the first holding member in the holding section of the energy treatment instrument of the treatment system according to the third modification of the first embodiment.

As shown in FIG. 9B, a communication path 170 of first and second fluid discharge grooves 152 and 162 is formed as a conduit in the same manner as shown in FIG. 8C of the second modification. Furthermore, a communication path 170a which connects the first fluid discharge groove 152 to a cutter guide groove 62a is also formed as a conduit.

As shown in FIGS. 9A and 9B, a cooling pipe 192 made of copper or the like having a satisfactory thermal conductivity is fixed to the edges of a main body 72 and a base portion 74 of a first holding member 62. Through the cooling pipe 192, a refrigerant such as cooling water (a liquid) or cooling air (a gas) is supplied.

A holding face 72b of the main body 72 is provided with a cooling plate 194 such as a copper plate having a satisfactory thermal conductivity. The cooling plate 194 is fixed to the main body 72 in a state where the plate comes in close contact with the cooling pipe 192. Therefore, when the refrigerant is passed through the cooling pipe 192, heat from the refrigerant is conducted from the cooling pipe 192 to the cooling plate 194. That is, the cooling plate 194 is cooled by the heat conducted from the cooling pipe 192.

Figure 10:
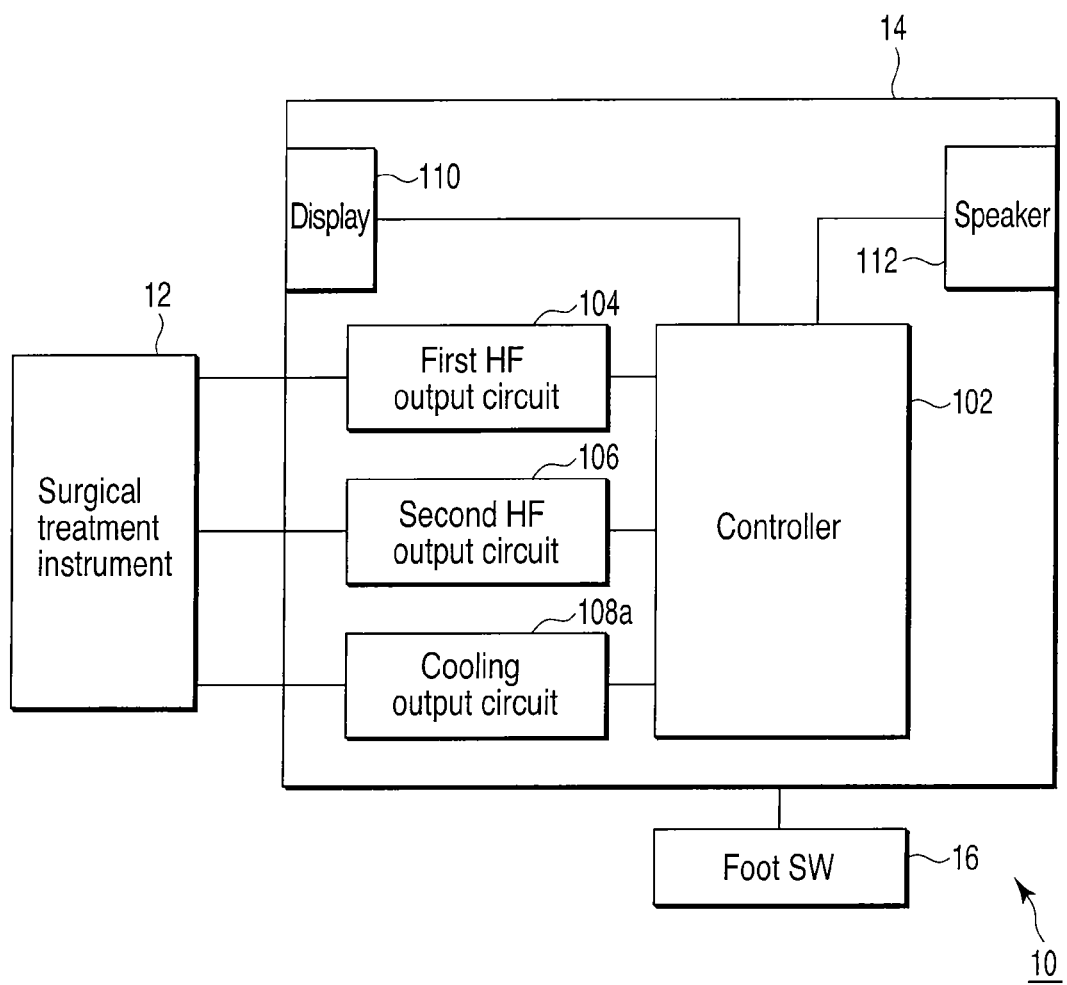
FIG. 10 is a schematic block diagram of the treatment system according to the third modification of the first embodiment.

Moreover, as shown in FIG. 10, in an energy source 14 of this modification, a cooling output circuit 108a is connected to a control section 102 instead of the temperature measurement circuit 108 described in the first embodiment. The cooling output circuit 108a can pass the refrigerant through the cooling pipe 192 of the surgical treatment instrument 12 in accordance with an instruction from the control section 102.

Next, an operation of a treatment system 10 according to this embodiment will be described.

Figure 11:
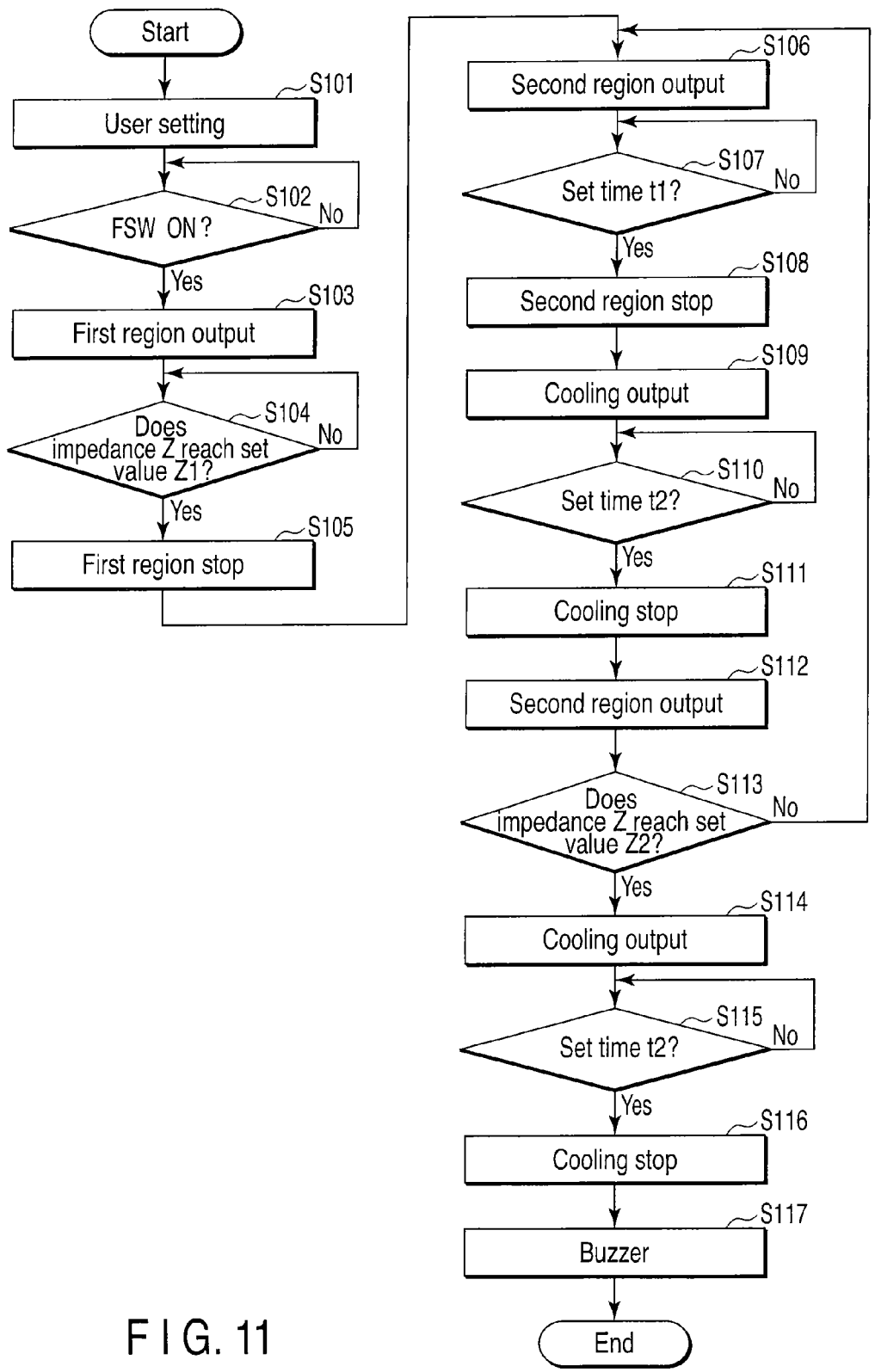
FIG. 11 is a schematic flow chart showing that a treatment using high-frequency energy is performed with respect to a living tissue by use of the treatment system according to the third modification of the first embodiment.

FIG. 11 shows one example of a control flow of the surgical treatment instrument 12 by a first high-frequency energy output circuit 104 and a second high-frequency energy output circuit 106.

An operator beforehand operates a display section 110 of the energy source 14 to beforehand set the output conditions of the treatment system 10 (STEP 101). Specifically, the operator beforehand sets the outputs (set powers P1set[W] and P2set[W]) from the first high-frequency energy output circuit 104 and the second high-frequency energy output circuit 106, threshold values Z1 and Z2 of an impedance Z of a living tissue $L_T$, a time of one output from the second high-frequency energy output circuit 106 (set time t1, t2) and the like.

The living tissue $L_T$ as a treatment target is grasped between the first and second holding members 62 and 64. At this time, the living tissue $L_T$ as the treatment target comes in contact with both a first and second continuous electrode 76 and 86 of the first and second holding members 62 and 64. The living tissue $L_T$ as the treatment target comes in contact with both first and second discrete electrodes 78 and 88 of the first and second holding members 62 and 64. A peripheral tissue of the living tissue $L_T$ as the treatment target comes in close contact with both facing contact faces at the edge of the holding face 72b of the first holding member 62 and the edge (not shown) of a holding face 82b of the second holding member 64. In consequence, the living tissue $L_T$ comes in close contact with the cooling plate 194.

In this way, a pedal 16a of a foot switch 16 is operated in the state where the living tissue $L_T$ is grasped between the first and second holding members 62 and 64. The control section 102 of the energy source 14 judges whether or not the pedal 16a of the switch 16 has been pressed to switch on by the operation of the operator (STEP 102).

When it is judged that the pedal 16a of the switch 16 has been pressed to switch on, high-frequency energy is supplied from the first high-frequency energy output circuit 104 of the energy source 14 to the living tissue (the living tissue of a first region) $L_T$ between the first continuous electrode 76 and the second continuous electrode 86 (STEP 103).

Consequently, the first high-frequency energy output circuit 104 supplies a high-frequency current to the living tissue $L_T$ as the treatment target between the first and second continuous electrodes 76 and 86 of the first and second holding members 62 and 64 as shown in the upper stage of FIG. 12A. That is, the high-frequency energy is applied to the living tissue $L_T$ grasped between the electrodes 76 and 86. In consequence, the living tissue $L_T$ is continuously denatured (a substantially U-shape) by the first and second continuous electrodes 76 and 86.

Next, the control section 102 judges whether or not the impedance Z during the high-frequency energy output calculated based on a signal from the high-frequency energy output circuit 104 exceeds the threshold value Z1 (here, about 1000 [Ω] as shown in FIG. 6B) beforehand (STEP 104). The threshold value Z1 is set to such a value that the rise ratio of the beforehand known value of the impedance Z falls. Subsequently, when it is judged that the impedance Z is smaller than the threshold value Z1, processing is returned to STEP 103. That is, the high-frequency energy for the treatment is continuously applied to the living tissue $L_T$ grasped between the first continuous electrode 76 of the first holding member 62 and the second continuous electrode 86 of the second holding member 64.

When it is judged that the impedance Z becomes larger than the threshold value Z1, the control section 102 transmits the signal to the first high-frequency energy output circuit 104. Then, the output from the first high-frequency energy output circuit 104 to the first and second continuous electrodes 76 and 86 is stopped (STEP 105).

Next, the second high-frequency energy output circuit 106 of the energy source 14 supplies energy to the living tissue (the living tissue of a second region) $L_T$ between the first and second discrete electrodes 78 and 88 (STEP 106). That is, the second high-frequency energy output circuit 106 supplies the high-frequency current to the living tissue $L_T$ between the first and second discrete electrodes 78 and 88 in a state offset temporally from the time when the first high-frequency energy output circuit 104 supplies the energy to the living tissue $L_T$ between the first and second continuous electrodes 76 and 86 (in a state where an output timing is offset) as shown in the middle stage of FIG. 12A.

In consequence, the high-frequency current flows through the living tissue $L_T$ grasped between the first and second holding members 62 and 64, and heat is generated from the living tissue $L_T$ by the function of Joule heat to start the cauterization of the tissue (the denaturalization of the tissue). In this case, the living tissue $L_T$ between the first and second discrete electrodes 78 and 88 is discretely denatured by the electrodes 78 and 88. At this time, the impedance Z of the grasped living tissue $L_T$ is measured by the second high-frequency energy output circuit 106 via the first and second discrete electrodes 78 and 88. Moreover, when the high-frequency current flows through the living tissue $L_T$ to cauterize the living tissue $L_T$, the value of the impedance Z rises.

Furthermore, after starting the output from the second high-frequency energy output circuit 106, it is judged whether or not the set time t1 has elapsed (STEP 107). When the set time t1 elapses, the output from the second high-frequency energy output circuit 106 to the first and second discrete electrodes 78 and 88 is stopped (STEP 108).

Immediately after the stop, as shown in the lower stage of FIG. 12A, the cooling output circuit 108a supplies a refrigerant through the cooling pipe 192 (STEP 109). In consequence, the living tissue $L_T$ is cooled via the cooling plate 194 which comes in close contact with the outer peripheral surface of the cooling pipe 192 having a high thermal conductivity. Therefore, the influence of the heat spread from the living tissue $L_T$ as the treatment target between the first and second discrete electrodes 78 and 88 is suppressed in a portion of the living tissue which comes in close contact with the cooling plate 194. That is, the thermal spread from the living tissue $L_T$ as the treatment target is suppressed by cooling the living tissue $L_T$ around the living tissue $L_T$ as the treatment target.

Subsequently, it is judged whether or not the set time t2 has elapsed after starting the supply of the refrigerant through the cooling pipe 192 (STEP 110). When the set time t2 elapses, the supply of the refrigerant from the cooling output circuit 108a is stopped (STEP 111).

Immediately after the stop, the second high-frequency energy output circuit 106 supplies the energy to the first and second discrete electrodes 78 and 88 (STEP 112). Subsequently, it is judged whether or not the impedance Z between the first and second discrete electrodes 78 and 88 has reached the threshold value Z2 (STEP 113). When it is judged that the impedance does not reach the threshold value, the processing returns to STEP 106, and the energy is again output from the second high-frequency energy output circuit 106 only for the set time t2. That is, the living tissue is repeatedly cauterized and cooled until the impedance Z reaches the threshold value Z2.

Moreover, when the impedance Z reaches the threshold value Z2, the cooling output circuit 108a supplies the refrigerant through the cooling pipe 192 to cool the living tissue $L_T$ via the cooling plate 194 (STEP 114). It is judged whether or not the refrigerant is supplied only for the set time t2 (STEP 115). After supplying the refrigerant only for the set time t2, the supply of the refrigerant is stopped to stop the cooling of the living tissue $L_T$ (STEP 116).

After the end of a series of treatments, a buzzer is sounded via a speaker 112 to inform the operator of the end of the treatment (STEP 117).

As described above, an effect is obtained as follows according to this embodiment.

In the treatment system 10 according to this embodiment, the description of the same effect as that described in the above embodiment is omitted.

According to the treatment instrument 12, immediately after applying the energy from the second high-frequency energy output circuit 106 to the living tissue $L_T$ as the treatment target held between the first and second discrete electrodes 78 and 88 of the first and second holding members 62 and 64, the cooling plates 194 of the first and second holding members 62 and 64 cooled, respectively, can be brought into close contact with the living tissue $L_T$. In consequence, the living tissue $L_T$ brought into close contact with the cooling plate 194 can be cooled. Therefore, the influence of the thermal spread caused from the living tissue $L_T$ as the treatment target to the peripheral living tissue $L_T$ can be suppressed in the portion of the living tissue which comes in contact with the cooling plate 194. In this case, the influence of the heat spread from the living tissue $L_T$ as the treatment target energized with high frequency during the treatment of the living tissue $L_T$ can be prevented from being exerted to another peripheral tissue.

Therefore, the first and second holding members 62 and 64 are provided with the cooling plates 194 which can cool the surfaces of the members, whereby a range in which the thermal spread occurs can securely be included inside the portion of the living tissue which comes in contact with the first and second holding members 62 and 64.

Moreover, even when the high-temperature fluid flows outwardly through the first and second holding members 62 and 64, the fluid comes in contact with the cooling plate 194 and can accordingly be cooled. In consequence, the living tissue $L_T$ around the living tissue $L_T$ held by the holding section 26 can be prevented from being influenced.

Furthermore, the other peripheral tissue can be prevented from being influenced by the fluid generated from the portion of the living tissue $L_T$ energized with the high frequency current during the treatment thereof. That is, a treatment region can be limited to the inside of barrier portions 98a and 98b, and the portions of the living tissue $L_T$ around the barrier portions 98a and 98b keep their normal state, which can contribute to earlier curing.

In addition, the supply of the high-frequency current to the living tissue $L_T$ between the first and second discrete electrodes 78 and 88 is offset from the supply of the refrigerant through the cooling pipe 192, whereby it is possible to suppress the rise of the impedance Z raised by the supply of the high-frequency current to the living tissue $L_T$ between the first and second discrete electrodes 78 and 88. In consequence, the living tissue $L_T$ between the first and second discrete electrodes 78 and 88 can more securely be subjected to a treatment such as joining.

It is to be noted that in this modification, there has been described an example in which the high-frequency current is supplied between the first and second continuous electrodes 76 and 86 and between the first and second discrete electrodes 78 and 88 and the refrigerant is supplied to the cooling pipe 192 as shown in FIG. 12A. Additionally, it is preferable to perform the energization with the high-frequency current and the supply of the refrigerant to the cooling pipe 192 in a state shown in FIG. 12B. That is, in a state offset from the output of the first high-frequency energy output circuit 104 and the stop of the output, the output from the second high-frequency energy output circuit 106 and the stop of the output are preferably performed simultaneously with the output from the cooling output circuit 108a and the stop of the output.

Moreover, in this modification, the output times t1 and t2 are set, but the control is preferably performed by use of a temperature T as described in the first embodiment. In this case, a threshold value T1 of the temperature T is set instead of the output times t1 and t2. Alternatively, the earliest reached threshold value may preferably be selected from the threshold values of the output times t1 and t2 and temperature T to perform the control.

Next, a modification of the third modification will be described with reference to FIG. 9C.

As shown in FIG. 9C, the cooling pipe 192 is removed. Instead, groove-like ducts 192a and 192b are integrally formed in a main body 72 and a base portion 74.

A cooling plate 194 is disposed on a holding face 72b of the main body 72. The cooling plate 194 seals the ducts 192a and 192b. In consequence, when a fluid is passed through the ducts 192a and 192b, the heat of the fluid is conducted to the cooling plate 194.

Next, a further modification of the third modification will be described with reference to FIG. 9D.

As shown in FIG. 9D, the cooling pipe 192 is removed. Instead, first and second groove-like ducts 192a and 192b are integrally formed in a main body 72 and a base portion 74. A pair of first or second ducts 192a or 192b are formed symmetrically with respect to the central axis of a cutter guide groove 62a of a first holding member 62. Among the pairs of first and second ducts 192a and 192b, a refrigerant such as cooling water flows into one pair, and the refrigerant flows out through the other pair.

It is to be noted that a communication path 170 which connects a first fluid discharge groove 152 to the cutter guide groove 62a is formed under the second duct 192b.

A holding face 72b of the main body 72 is provided with a thin and soft sheet-like member (a member for heat radiation) 194a. The sheet-like member 194a is made of, for example, a silicone material. The sheet-like member 194a seals the ducts 192a and 192b. In consequence, when a fluid is passed through the ducts 192a and 192b, the heat of the fluid is conducted to a living tissue $L_T$ through the sheet-like member 194a.

[Fourth Modification of First Embodiment]

Next, a fourth modification of the first embodiment will be described with reference to FIGS. 13A to 16. This modification is a further modification of the third modification.

Figure 13A:
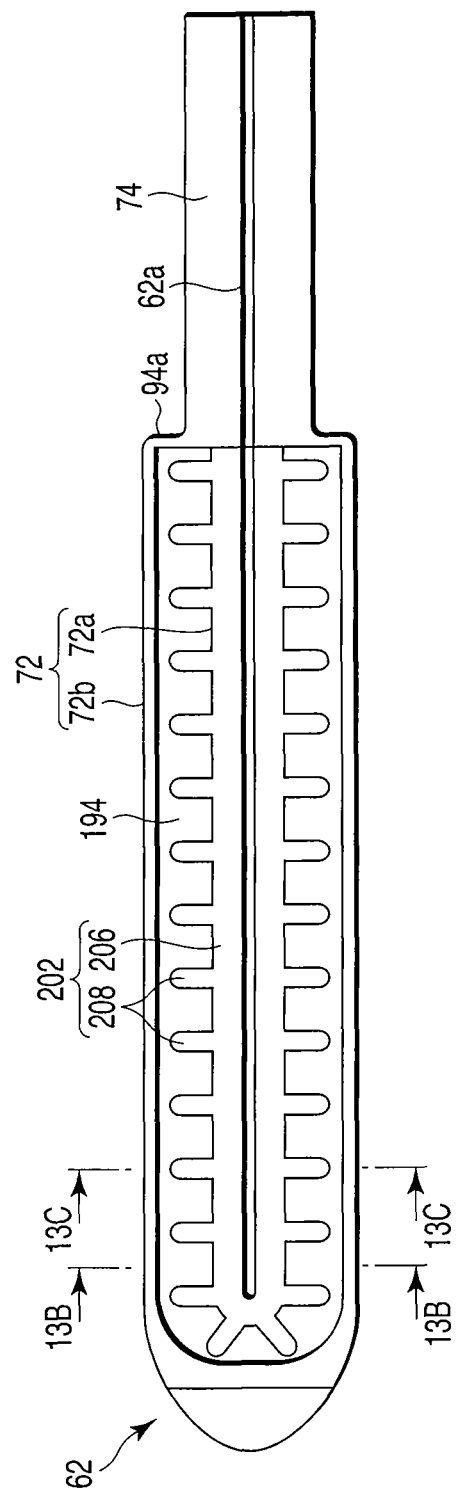
FIG. 13A is a schematic plan view showing a first holding member on a side close to a second holding member in a holding section of an energy treatment instrument of a treatment system according to a fourth modification of the first embodiment.
Figure 13B:
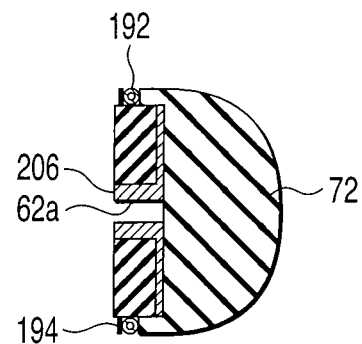
FIG. 13B is a schematic transverse sectional view cut along the 13B-13B line of FIG. 13A and showing the first holding member in the holding section of the energy treatment instrument of the treatment system according to the fourth modification of the first embodiment.
Figure 13C:
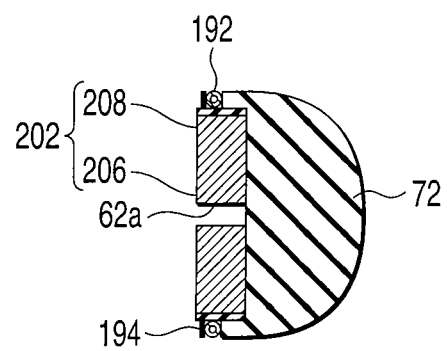
FIG. 13C is a schematic transverse sectional view cut along the 13C-13C line of FIG. 13A and showing a modification of the first holding member in the holding section of the energy treatment instrument of the treatment system according to the fourth modification of the first embodiment.

As shown in FIGS. 13B and 13C, a cooling pipe 192 is fixed to the edges of a main body 72 and a base portion 74 of a first holding member 62. Moreover, a holding face 72b of the main body 72 of the first holding member 62 is provided with a cooling plate 194. The cooling plate 194 is fixed to the main body 72 in a state where the cooling plate comes in close contact with the cooling pipe 192.

As shown in FIG. 13A, the main body 72 of the first holding member 62 is provided with a first electrode 202 instead of a first continuous electrode 76 and first discrete electrodes 78. That is, the first electrode 202 includes a first continuous electrode 206 corresponding to the first continuous electrode 76 and first branched electrodes 208 corresponding to the first discrete electrodes 78.

Although not shown, a main body 82 of a second holding member 64 is similarly provided with a second electrode (conveniently denoted with reference numeral 212) instead of a second continuous electrode 86 and second discrete electrodes 88. That is, the second electrode 212 includes a second continuous electrode (conveniently denoted with reference numeral 216) corresponding to the second continuous electrode 86 and second branched electrodes (conveniently denoted with reference numeral 218) corresponding to the second discrete electrodes 88.

It is to be noted that as shown in FIG. 14, an energy source 14 is provided with a high-frequency energy output circuit 105 instead of first and second high-frequency energy output circuits 104 and 106.

As shown in FIG. 13A, the first continuous electrode 206 is continuously formed into a substantially U-shape. Outside the first continuous electrode 206, a plurality of first branched electrodes (a maintaining member, a second joining member) 208 branched from the first continuous electrode 206 are integrally formed. The first branched electrodes 208 extend in an orthogonal direction to the axial direction of the first continuous electrode 206.

The first branched electrodes 208 are formed with a substantially equal length and a substantially equal width. That is, the first branched electrodes 208 extend as much as a substantially equal area from the first continuous electrode 206, respectively. Each space between the first branched electrodes 208 is a substantially equal space.

It is to be noted that the first branched electrodes 208 denature a living tissue $L_T$ which comes in contact with the first branched electrodes 208, but the electrodes emit output to such an extent that the denaturation of the living tissue $L_T$ between the adjacent first branched electrodes 208 is prevented. Such output depends on the energy input from the high-frequency energy output circuit 105 to the first branched electrodes 208 and additionally on the space between the first branched electrodes 208, the width of the first branched electrode 208 itself and the like.

It is to be noted that the length and width (thickness) of each of the first branched electrodes 208, the space between the first branched electrodes 208 and the number of the branched electrodes are appropriately set. In FIG. 13A, it is depicted that the thickness of the first continuous electrode 206 is larger than that of the first branched electrode 208, but the thickness may be equal, or the thickness of the first branched electrode 208 may be larger.

Next, an operation of a treatment system 10 according to this modification will be described.

Figure 15:
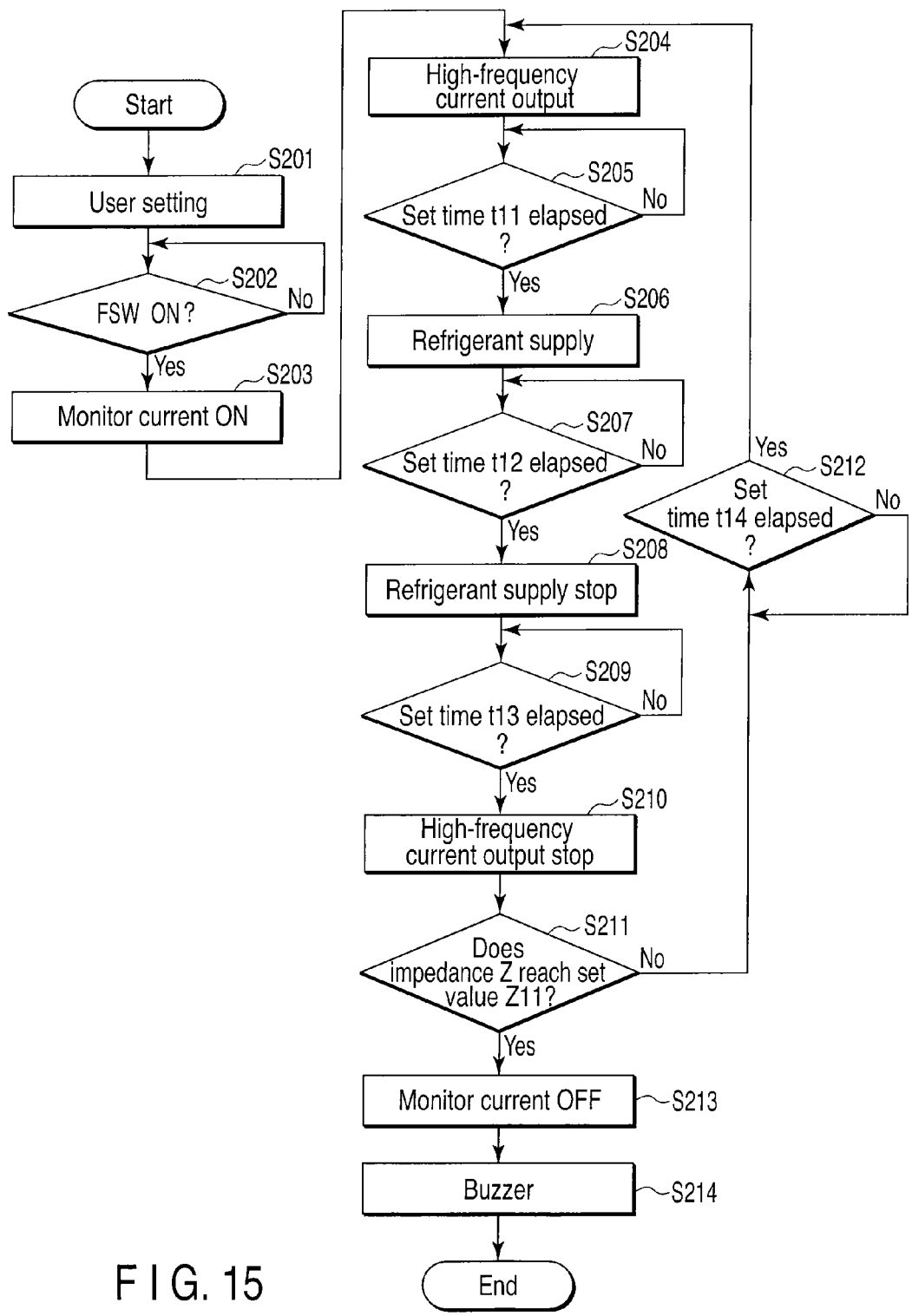
FIG. 15 is a schematic flow chart showing that a treatment using high-frequency energy is performed with respect to a living tissue by use of the treatment system according to the fourth modification of the first embodiment.

FIG. 15 shows one example of a control flow of a surgical treatment instrument 12 by the first high-frequency energy output circuit 105 and a cooling output circuit 108a.

An operator beforehand operates a display section 110 of the energy source 14 to beforehand set the output conditions of the treatment system 10 (STEP 201). Specifically, the operator beforehand sets the output (a set power P1set[W]) from the high-frequency energy output circuit 105, a threshold value Z11 of an impedance Z of a living tissue $L_T$, a time of one output from the cooling output circuit 108a (a set time t12), a time difference t11 between the output start time of the high-frequency energy output circuit 105 and the output start time of the cooling output circuit 108a, a time difference t13 between the output stop time of the cooling output circuit 108a and the output stop time of the high-frequency energy output circuit 105, a time difference t14 between the output start time of the high-frequency energy output circuit 105 and the output stop time of the high-frequency energy output circuit 105 and the like.

The living tissue $L_T$ as a treatment target is grasped between the first and second holding members 62 and 64. At this time, the living tissue $L_T$ as the treatment target comes in contact with both the first electrode 202 of the first holding member 62 and the second electrode 212 of the second holding member 64. That is, the living tissue $L_T$ as the treatment target comes in contact with portions between the first continuous and branched electrodes 206 and 208 of the first electrode 202 and the second continuous and branched electrodes 216 and 218 of the second electrode 212. Moreover, a peripheral tissue of the living tissue $L_T$ as the treatment target comes in close contact with both facing contact faces at the edge of the holding face 72b of the first holding member 62 and the edge (not shown) of a holding face 82b of the second holding member 64. In consequence, the living tissue $L_T$ comes in close contact with the cooling plate 194.

In this way, a pedal 16a of a foot switch 16 is operated in the state where the living tissue $L_T$ is grasped between the first and second holding members 62 and 64. A control section 102 of the energy source 14 judges whether or not the pedal 16a of the switch 16 has been pressed to switch on by the operation of the operator (STEP 202).

When it is judged that the pedal 16a of the switch 16 has been pressed to switch on, the supply of a monitor current from the high-frequency energy output circuit 105 is switched on (STEP 203), and high-frequency energy is supplied from the high-frequency energy output circuit 105 of the energy source 14 to the living tissue $L_T$ between the first and second electrodes 202 and 212 (STEP 204).

Figure 16:
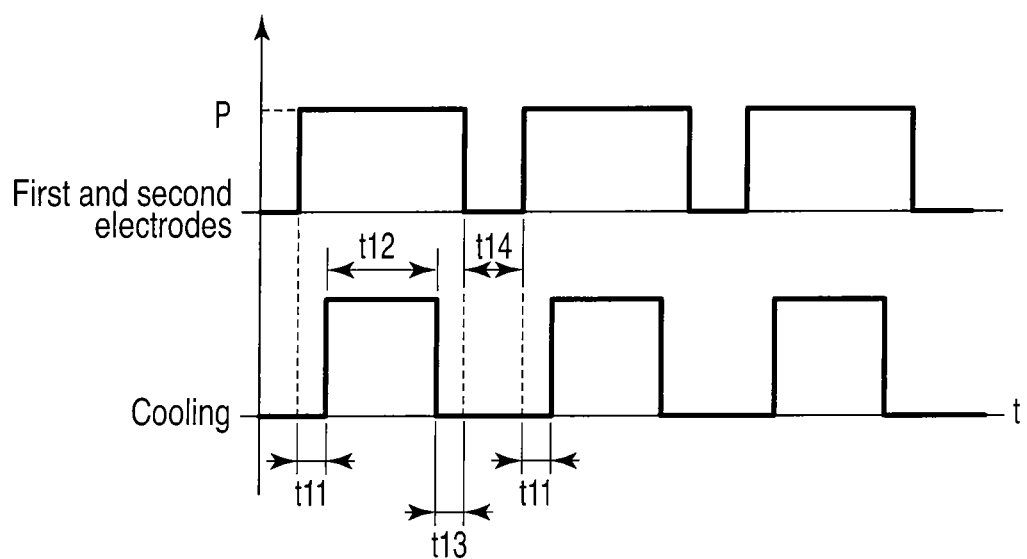
FIG. 16 is a schematic graph showing one example of an input process of inputting the high-frequency energy into the living tissue with respect to time in the case where the treatment using the high-frequency energy is performed with respect to the living tissue by use of the treatment system according to the fourth modification of the first embodiment.

Consequently, the high-frequency energy output circuit 105 supplies a high-frequency current to the living tissue $L_T$ as the treatment target between the first and second electrodes 202 and 212 of the first and second holding members 62 and 64 as shown in the upper stage of FIG. 16. In consequence, the living tissue $L_T$ is continuously denatured (substantially U-shaped) by the first and second electrodes 202 and 212, and is denatured in a branched state at each predetermined interval.

Afterward, when the set time t11 elapses (STEP 205), as shown in the lower stage of FIG. 16, the cooling output circuit 108a supplies a refrigerant to the cooling pipe 192 (STEP 206). Subsequently, when the set time t12 elapses (STEP 207), the supply of the refrigerant is stopped (STEP 208). It is to be noted that during these operations, the high-frequency current continues to be supplied to the living tissue $L_T$ between the first and second electrodes 202 and 212.

Subsequently, when the set time t13 elapses from the stop of the supply of the refrigerant (STEP 209), the monitor current maintains its on-state to stop the supply of the high-frequency current (STEP 210), and the value of the impedance Z of the living tissue $L_T$ between the first and second electrodes 202 and 212 is determined (STEP 211). When the impedance Z does not reach the set value (the threshold value) Z11 and the set time t14 elapses (STEP 212), the processing again returns to STEP 204, thereby repeating the energization with the high-frequency current and the supply of the refrigerant.

On the other hand, when the impedance Z reaches the set value Z11, the monitor current from the high-frequency energy output circuit 105 is turned off (STEP 213), and a buzzer is sounded via a speaker 112 (STEP 214) to end the treatment.

Figure 17A:
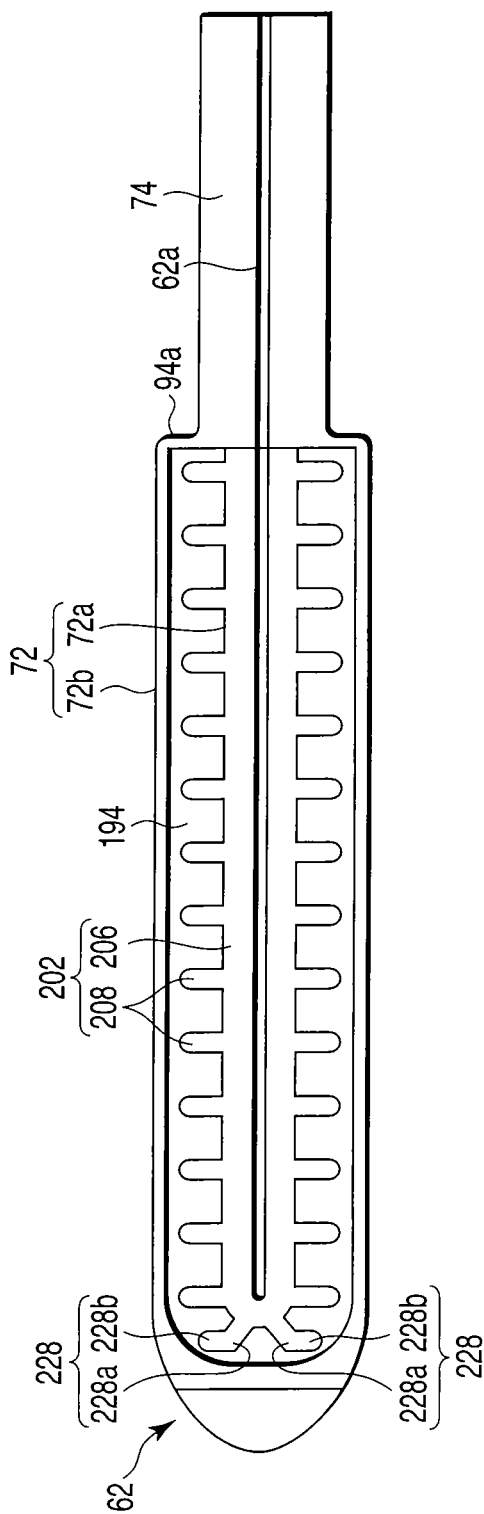
FIG. 17A is a schematic plan view showing a first holding member on a side close to a second holding member in a holding section of an energy treatment instrument of a treatment system according to a modification of the fourth modification of the first embodiment.
Figure 17B:
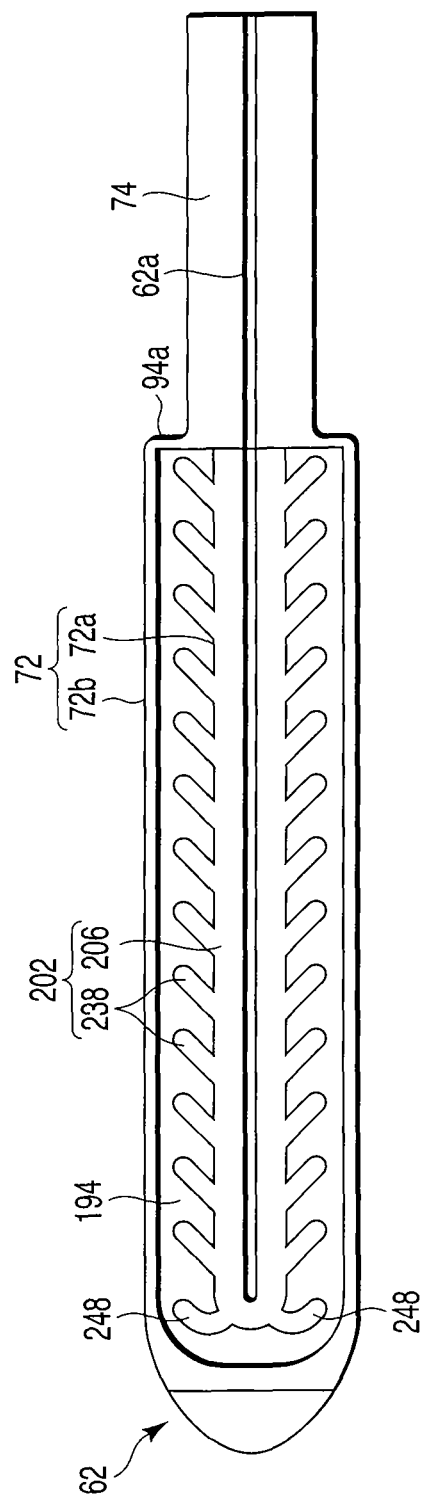
FIG. 17B is a schematic plan view showing a first holding member on a side close to a second holding member in a holding section of an energy treatment instrument of a treatment system according to a further modification of the fourth modification of the first embodiment.

It is to be noted that in this modification, the use of the first electrode 202 having a shape shown in FIG. 13A has been described, but an electrode having a shape shown in FIG. 17A or 17B is preferably used.

A modification of the first branched electrode 208 of the first electrode 202 will be described with reference to FIG. 17A.

As shown in FIG. 17A, first branched electrodes (a maintaining member, a second joining member) 228 on the most distal end (a side away from a base portion 74) of a main body 72 of a first holding member 62 are deformed with respect to branched electrodes 208 on the most distal end of the main body 72 of the first holding member 62 shown in FIG. 13A. That is, the branched electrodes 228 shown in FIG. 17A are formed to be long as compared with the branched electrodes 208 on the most distal end of the main body 72 of the first holding member 62 shown in FIG. 13A.

Moreover, the branched electrodes 208 on the most distal end shown in FIG. 13A extend only in one direction (straight). On the other hand, the extending angle of each of the branched electrodes 228 shown in FIG. 17A varies at the midpoint (the electrode is bent at the midpoint). This is because a joining force to join intestinal canals $I_{C1}$ and $I_{C2}$ to each other is increased to prevent the release of the anastomosed canals, in a case where when the intestinal canals $I_{C1}$ and $I_{C2}$ are anastomosed as shown in, for example, FIG. 7C, and a force $F_2$ is exerted so as to release the anastomosed intestinal canals $I_{C1}$ and $I_{C2}$ from the tip of a portion denatured by a continuous electrode 206, i.e., a portion $B_i$ where the intestinal canals $I_{C1}$ and $I_{C2}$ are branched.

The branched electrodes 228 shown in FIG. 17A extend in at least two directions, respectively. Each of the branched electrodes 228 includes a first portion 228a formed integrally with the continuous electrode 206 and extended in an orthogonal direction to a substantially U-shaped virtual track of the continuous electrode 206, and a second portion 228b formed integrally with the first portion 228a and extended further from the first portion 228a. The second portion 228b of these portions extends in parallel with the branched electrodes 208. Moreover, in such a constitution, the branched electrode 228 has the first portion 228a and the second portion 228b, whereby a joining area corresponding to the force $F_2$ generated in the branched portion $B_i$ can be increased. That is, owing to the first portion 228a and the second portion 228b, the intestinal canals $I_{C1}$ and $I_{C2}$ joined to each other do not easily peel.

Therefore, a resistance to the force $F_2$ applied to the intestinal canals $I_{C1}$ and $I_{C2}$ can be increased to obtain a state where the anastomosed intestinal canals $I_{C1}$ and $I_{C2}$ are not easily released.

Next, a further modification of the branched electrodes 208 will be described with reference to FIG. 17B.

As shown in FIG. 17B, branched electrodes (a maintaining member, a second joining member) 238 of a first holding member 62 are deformed with respect to the branched electrodes 208 of the first holding member 62 shown in FIG. 13A. The branched electrodes 238 are arranged in an oblique direction, instead of an orthogonal direction to the axial direction of a continuous electrode 206 (a substantially U-shaped virtual track) of the continuous electrode 206. In this modification, the branched electrodes 238 extend toward, for example, a proximal end.

Figure 7D:
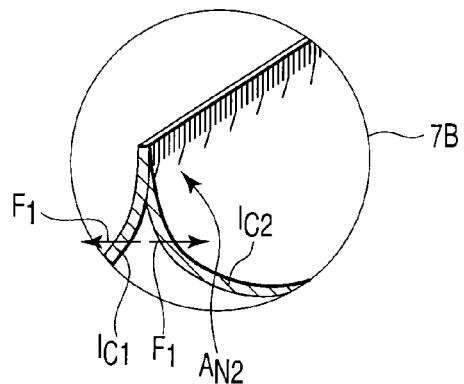
FIG. 7D is a schematic diagram as a modification of FIG. 7B showing the enlarged part denoted with the symbol 7B of FIG. 7A.

Therefore, as shown in FIG. 7D, in intestinal canals $I_{C1}$ and $I_{C2}$, there are portions joined by the continuous electrode 206 and portions joined by the branched electrodes 238 with an appropriate angle in the longitudinal direction of the portions joined by the continuous electrode 206. The branched electrodes 238 are formed to be long as compared with the branched electrodes 208 shown in FIG. 13A. Moreover, the portions joined by the branched electrodes 238 are disposed obliquely with respect to the direction of a force $F_1$ applied to the intestinal canals $I_{C1}$ and $I_{C2}$. Therefore, with regard to the branched electrodes 238, a joining area corresponding to the force $F_1$ having such a direction as to release the anastomosed canals increases, so that it is possible to obtain a state where the anastomosed intestinal canals $I_{C1}$ and $I_{C2}$ are not easily released. Therefore, the branched electrodes 238 having an appropriate angle with respect to the longitudinal direction of the portion connected to the continuous electrode 206 can have an increased joining force to join the intestinal canals $I_{C1}$ and $I_{C2}$ to each other.

It is to be noted that as shown in FIG. 17B, branched electrodes (a maintaining member, a second joining member) 248 on the most distal end of the first holding member 62 are deformed with respect to the branched electrodes 208 and 228 on the most distal end of the first holding member 62 shown in FIGS. 13A and 17A. That is, the branched electrodes 248 of this modification are formed to be long as compared with the branched electrodes 208 and 228 on the most distal end of the first holding member 62 shown in FIGS. 13A and 17A.

Furthermore, the branched electrodes 248 shown in FIG. 17B are circularly extended. Therefore, the branched electrodes 248 are extended in a direction different from that of the branched electrodes 238. In such branched electrodes 248 provided on the distal end of the first holding member 62, a resistance is increased against a force $F_2$ generated in a portion $B_i$ shown in FIG. 17B, in a case where the intestinal canals $I_{C1}$ and $I_{C2}$ are anastomosed, whereby the intestinal canals $I_{C1}$ and $I_{C2}$ do not easily peel from each other.

This is because the joining force to join the intestinal canals $I_{C1}$ and $I_{C2}$ to each other is increased to prevent the release of the anastomosed canals, in a case where, for example, when the intestinal canals $I_{C1}$ and $I_{C2}$ are anastomosed, the force $F_2$ is exerted so as to release the anastomosed intestinal canals $I_{C1}$ and $I_{C2}$ from the distal end of a portion denatured by the continuous electrode 206, i.e., the portion $B_i$ where the intestinal canals $I_{C1}$ and $I_{C2}$ are branched from each other.

It is to be noted that in this modification, the branched electrodes 228 each having the first portion 228a and the second portion 228b and the branched electrodes 248 have been described as the branched electrodes disposed on the most distal end of a main body 72 of the first holding member 62 in a case where the area of the joining portion corresponding to the force $F_2$ is increased. However, the shapes of the branched electrodes disposed on the most distal end of the main body 72 of the first holding member 62 are not limited to the branched electrodes 228 and 248, as long as the area of the joining portion corresponding to the force $F_2$ increases.

Figure 18:
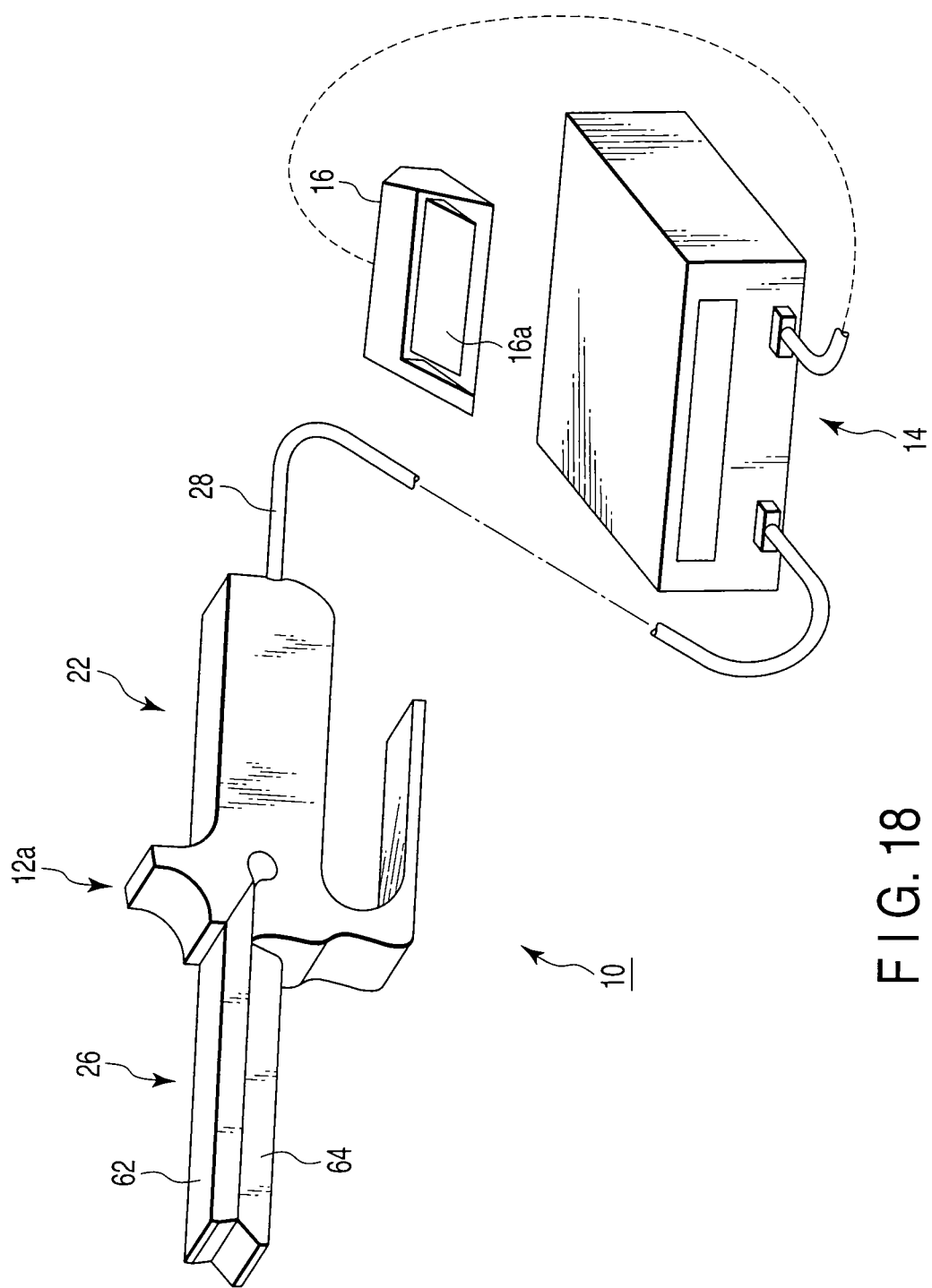
FIG. 18 is a schematic diagram showing a modification of the treatment system according to the first embodiment.

Moreover, in the first embodiment and the modifications thereof, the linear type energy treatment instrument 12 (see FIG. 1A) for treating the living tissue $L_T$ in the abdominal cavity (in the body) through the abdominal wall has been described as the example, but as shown in, for example, FIG. 18, there may be used an opening linear type energy treatment instrument (a treatment instrument) 12a for taking a treatment target tissue from the body through the abdominal wall to treat the tissue.

The energy treatment instrument 12a includes a handle 22 and a holding section 26. That is, unlike the energy treatment instrument 12 (see FIG. 1A) for treating the tissue through the abdominal wall, a shaft 24 is omitted. On the other hand, a member having a function similar to that of the shaft 24 is disposed in the handle 22. In consequence, the energy treatment instrument 12a shown in FIG. 18 can be used in the same manner as in the energy treatment instrument 12 described above with reference to FIG. 1A.

[Second Embodiment]

Next, a second embodiment will be described with reference to FIGS. 19 to 21. This embodiment is a modification of the first embodiment including various modifications.

Here, as one example of an energy treatment instrument, a circular type bipolar energy treatment instrument (a treatment instrument) 312 for performing a treatment, e.g., through or outside an abdominal wall will be described.

As shown in FIG. 19, a treatment system 310 includes the energy treatment instrument 312, an energy source 14 and a foot switch 16. The surgical treatment instrument 312 includes a handle 322, a shaft 324 and an openable/closable holding section 326. The handle 322 is connected to the energy source 14 via a cable 28.

The handle 322 is provided with a holding section opening/closing knob 332 and a cutter driving lever 334. The holding section opening/closing knob 332 is rotatable with respect to the handle 322. When the holding section opening/closing knob 332 is rotated, for example, clockwise with respect to the handle 322, a detachable side holding section (a detachable side grasping section) 344 of the holding section 326 described later comes away from a main body side holding section (a main body side grasping section) 342. When the knob is rotated counterclockwise, the detachable side holding section 344 comes close to the main body side holding section 342.

The shaft 324 is formed into a cylindrical shape. The shaft 324 is appropriately curved in consideration of insertion properties upon insertion into a living tissue $L_T$. Needless to say, it is also preferable that the shaft 324 is formed to be straight.

Figure 20A:
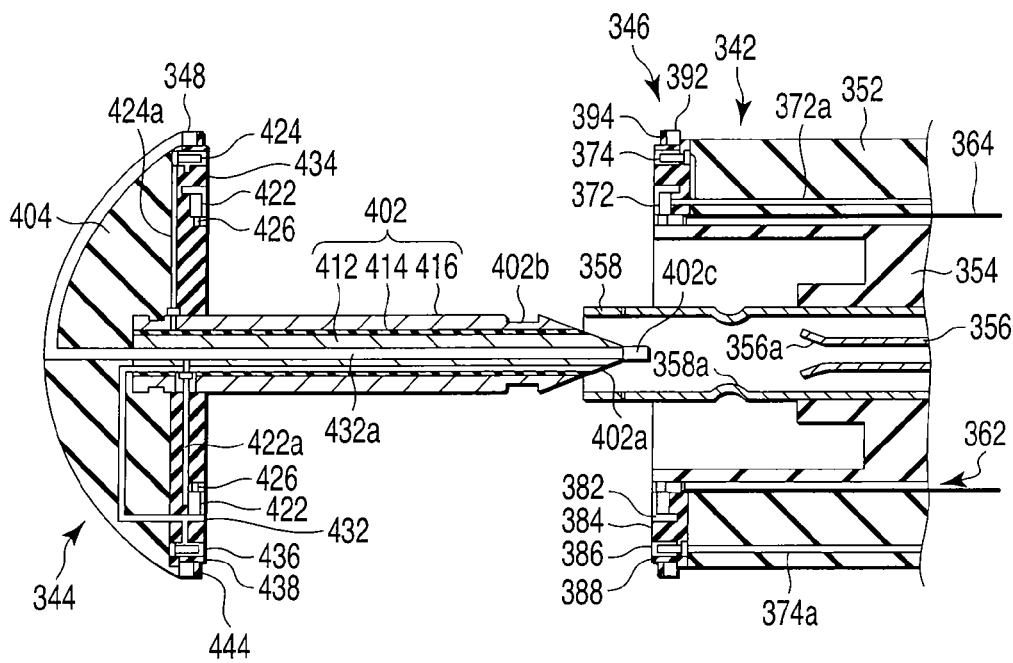
FIG. 20A is a schematic vertical sectional view showing a state where a main body side holding section and a detachable side holding section of an energy treatment instrument according to the second embodiment are disengaged.
Figure 20B:
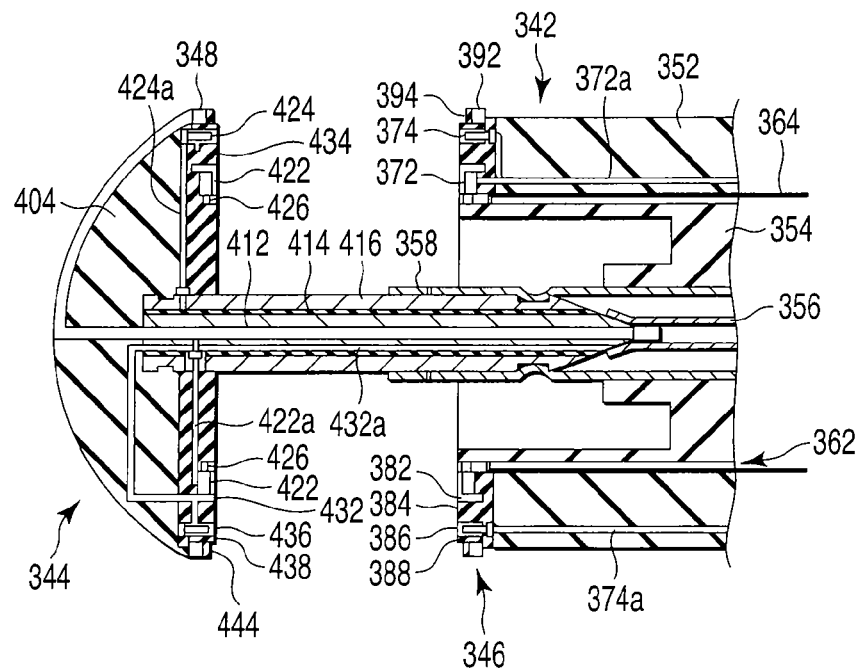
FIG. 20B is a schematic vertical sectional view showing a state where the main body side holding section and the detachable side holding section of the energy treatment instrument according to the second embodiment are engaged, and the detachable side holding section is disposed away from the main body side holding section.

The distal end of the shaft 324 is provided with the holding section 326. As shown in FIGS. 20A and 20B, the holding section 326 includes the main body side holding section (a first holding member, a first jaw) 342 formed on the distal end of the shaft 324, and the detachable side holding section (a second holding member, a second jaw) 344 detachably attached to the main body side holding section 342. In a state where the detachable side holding section 344 closes with respect to the main body side holding section 342, holding faces 384, 388, 434 and 438 of the main body side holding section 342 and the detachable side holding section 344 described later come in contact with one another.

Outside the shaft 324 and the main body side holding section 342, a first conduit 346 is formed. The first conduit 346 is disposed around the outer peripheral surface of the edge of the distal end of the main body side holding section 342, and is extended from the main body side holding section 342 to the proximal end side of the shaft 324.

The detachable side holding section 344 is provided with a second conduit 348. The second conduit 348 is disposed around the edge of a head section 404 of the detachable side holding section 344, and is connected from the energization shaft 324 of the detachable side holding section 344 described later to a first energizing pipe 356 and a fluid supplying pipe 360 in the main body side holding section 342 and the shaft 324 described later.

The main body side holding section 342 includes a cylindrical member 352, a frame 354, the first energizing pipe 356 having a fluid collecting function, a second energizing pipe 358 and the fluid supplying pipe 360. The first energizing pipe 356 is connected to a first high-frequency energy output circuit 104 of the energy source 14 via the main body side holding section 342, the shaft 324, the handle 322 and the cable 28. The second energizing pipe 358 is connected to a second high-frequency energy output circuit 106 of the energy source 14 via the main body side holding section 342, the shaft 324, the handle 322 and the cable 28 in the same manner as in the first energizing pipe 356.

The fluid supplying pipe 360 is preferably made of a resin material such as a silicone material having insulation properties. The fluid supplying pipe 360 is used to supply a refrigerant to the second conduit (a detachable side cooling pipe) 348 of the detachable side holding section 344. The first energizing pipe 356 is used to collect the refrigerant supplied from the fluid supplying pipe 360 to the second conduit 348.

The cylindrical member 352 and the frame 354 have insulation properties. The cylindrical member 352 is connected to the distal end of the shaft 324. The frame 354 is disposed to be fixed to the cylindrical member 352.

Figure 20C:
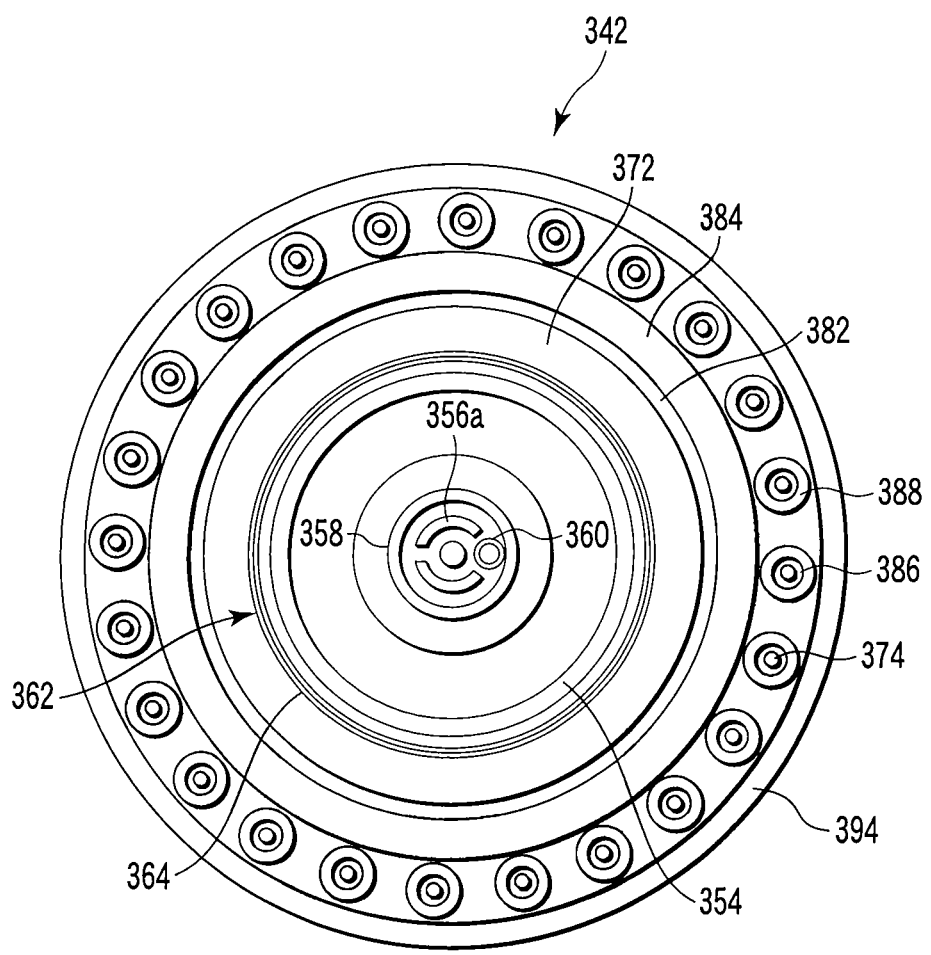
FIG. 20C is a schematic diagram showing the surface of the main body side holding section of the energy treatment instrument according to the second embodiment.

The central axis of the frame 354 is opened. The opened central axis of the frame 354 is provided with the first energizing pipe 356 so that the pipe 356 is movable in a predetermined range along the central axis of the frame 354. When the holding section opening/closing knob 332 is rotated, the first energizing pipe 356 is movable in the predetermined range owing to, for example, the function of a ball screw (not shown). In the first energizing pipe 356, a plurality of (e.g., two as shown in FIG. 20C or three (not shown)) divided and enlarged diameter portions 356a are formed to receive a distal end 402a of an energizing shaft 402 of the detachable side holding section 344 described later as shown in FIGS. 20A to 20C. The enlarged diameter portions 356a impart spring properties to the distal end of the first energizing pipe 356 and flexibly hold the distal end 402a while keeping a state where the distal end 402a of the energizing shaft 402 comes in contact with the distal end of the pipe 356.

The second energizing pipe 358 is disposed along the central axis of the first energizing pipe 356. When the holding section opening/closing knob 332 is rotated, the second energizing pipe 358 is movable together with the first energizing pipe 356 in a predetermined range by the function of, for example, a ball screw (not shown). The inner peripheral surface of the distal side of the second energizing pipe 358 is provided with a protrusion 358a protruding inwardly in a diametric direction so that the protrusion can disengageably be engaged with a connecting portion 402b of the energizing shaft 402.

It is to be noted that the first and second energizing pipes 356 and 358 are arranged so that the pipes 356 and 358 do not come in contact with each other, but the outer peripheral surface of the first energizing pipe 356 is covered with a material having insulation properties (not shown). In consequence, even when the first energizing pipe 356 comes in contact with the second energizing pipe 358, the pipes are prevented from being influenced by each other.

As shown in FIGS. 20A and 20B, a cutter guide groove (a first fluid passage) 362 is formed between the cylindrical member 352 and the frame 354. A cylindrical cutter 364 is disposed in the cutter guide groove 362. The proximal end of the cutter 364 is connected to the outer peripheral surface of the distal end of a pusher for the cutter (not shown) disposed on the proximal end side of the frame 354. The proximal end of this pusher for the cutter is connected to the cutter driving lever 334 of the handle 322. Therefore, when the cutter driving lever 334 of the handle 322 is operated, the cutter 364 moves via the pusher for the cutter.

A first fluid passage (a fluid passage) (not shown) connected to the cutter guide groove 362 is formed between this pusher for the cutter and the frame 354. Moreover, the shaft 324 or the handle 322 is provided with a fluid discharge port (not shown) through which the fluid passed through the cutter guide groove 362 is discharged to the outside.

As shown in FIGS. 20A to 20C, the distal end of the cylindrical member 352 is provided with a first continuous electrode (a seal member, a first joining member) 372 and a plurality of first discrete electrodes (a maintaining member, a second joining member) 374 as an output member or an energy release section. The first continuous electrode 372 is formed into a continuous annular shape without any cut. The first discrete electrodes 374 are discretely arranged at predetermined intervals outside the first continuous electrode 372.

The first continuous electrode 372 is fixed to the distal end of a first energization line 372a. The first energization line 372a is connected to the cable 28 via the main body side holding section 342, the shaft 324 and the handle 322. The first discrete electrodes 374 are electrically connected to each other, and the one first discrete electrode 374 is fixed to the distal end of a second energization line 374a. The second energization line 374a is connected to the cable 28 via the main body side holding section 342, the shaft 324 and the handle 322.

The first continuous electrode 372 is interposed between the edge of the cutter guide groove 362 provided with the cutter 364 and the edge of the cylindrical member 352. The first continuous electrode 372 is disposed on a side close to the outer edge of the cutter guide groove 362.

The first discrete electrodes 374 having the same shape are arranged at substantially equal intervals along a substantially annular virtual track. Each of the first discrete electrodes 374 is formed into, for example, a circular shape. The first discrete electrodes 374 are arranged with a substantially predetermined interval therebetween, and each of the first discrete electrodes 374 is positioned as much as an appropriate distance away from the first continuous electrode 372. The first discrete electrodes 374 are positioned so that a living tissue $L_T$ between the adjacent first discrete electrodes 374 is prevented from being denatured by heat during a treatment as much as possible and so that the living tissue $L_T$ between the first discrete electrode 374 and the first continuous electrode 372 is prevented from being denatured by the heat as much as possible.

An annular vapor discharge groove 382 is formed outside the first continuous electrode 372. That is, the vapor discharge groove 382 is formed between the first continuous electrode 372 and the first discrete electrode 374. The fluid discharge groove 382 is connected to the cutter guide groove 362 in which the cutter 364 is disposed. Outside the fluid discharge groove 382, the holding face (a tissue contact face) 384 is formed at a position higher than the surface of the first continuous electrode 372. That is, the holding face 384 of the main body side holding section 342 is disposed closer to the head section 404 of the detachable side holding section 344, described later, than the surface of the first continuous electrode 372 is. Therefore, the holding face 384 functions as a barrier portion (a dam) which prevents a fluid such as vapor from escaping to the outside from the fluid discharge groove 382.

An annular vapor discharge groove 386 is formed outside the first discrete electrodes 374. The fluid discharge groove 386 is connected to the fluid discharge groove 382 and the cutter guide groove 362 arranged outside the first continuous electrode 372. Outside the fluid discharge groove 386, the holding face (a tissue contact face) 388 is formed at a position higher than the surfaces of the first discrete electrodes 374. In consequence, the holding face 388 functions as a barrier portion (a dam) which prevents a fluid such as the vapor from escaping to the outside from the fluid discharge groove 386.

Figure 21:
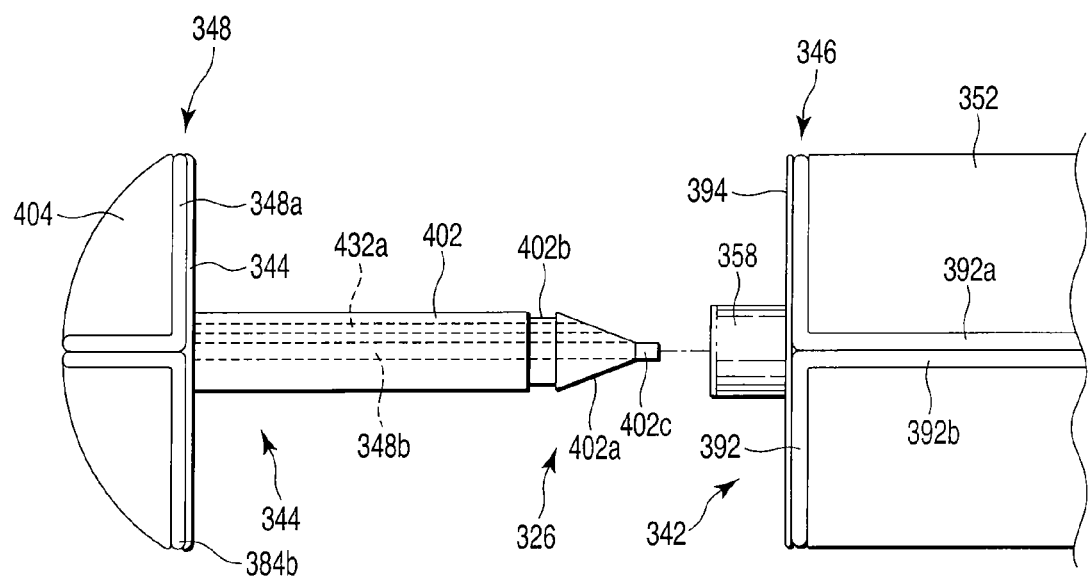
FIG. 21 is a schematic diagram showing the state where the main body side holding section and the detachable side holding section of the energy treatment instrument according to the second embodiment are disengaged.

As shown in FIGS. 20A to 21, the first conduit 346 includes a main body side cooling pipe 392 fixed to the outermost periphery of the cylindrical member 352 of the main body side holding section 342. The cooling pipe 392 is disposed on the outer peripheral surfaces of the main body side holding section 342 and the shaft 324, and is extended to the proximal end side of the shaft 324. The cooling pipe 392 is made of, for example, copper or the like having a satisfactory thermal conductivity. Through the cooling pipe 392, a refrigerant such as cooling water (a liquid) or cooling air (a gas) is circulated and discharged. It is to be noted that the cooling pipe 392 supplies the fluid on a side denoted with symbol 392a shown in FIG. 21, and collects the fluid on a side denoted with symbol 392b.

The holding face 388 of the main body side holding section 342 is provided with a main body side cooling plate 394 such as a copper plate having a satisfactory thermal conductivity. The cooling plate 394 is fixed to the distal end of the cylindrical member 352 in a state where the plate comes in close contact with the cooling pipe 392. In consequence, when a refrigerant is passed through the cooling pipe 392, the heat of the refrigerant is conducted from the cooling pipe 392 to the cooling plate 394. That is, the cooling plate 394 is cooled.

Moreover, in the energy source 14 of this modification, a cooling output circuit 108a is connected to a control section 102 instead of the temperature measurement circuit 108 described in the first embodiment. The cooling output circuit 108a can supply the refrigerant through the cooling pipe 392 of the surgical treatment instrument 312 in accordance with an instruction from the control section 102.

On the other hand, the detachable side holding section 344 includes the energizing shaft 402 and the head section 404 having insulation properties. The energizing shaft 402 has a circular cross section, and has one end tapered and the other end fixed to the head section 404. The energizing shaft 402 has a three-layer structure in which three cylindrical members 412, 414 and 416 schematically come in close contact with one another. The inside (the inner layer) 412 of the energizing shaft 402 is a cylindrical member having a conductivity, the intermediate layer 414 is a cylindrical member having insulation properties, and the outside (the outer layer) 416 is a cylindrical member having a conductivity.

Moreover, the distal end of the inner layer 412 (the distal end 402a of the energizing shaft 402) is electrically connected to the enlarged diameter portions 356a of the first energizing pipe 356. The outer peripheral surface of the distal end side of the outer layer 416 is provided with the connecting portion (a recess groove portion) 402b which engages with the protrusion 358a of the second energizing pipe 358. It is to be noted that in the outer peripheral surface of the outer layer 416, a portion other than the connecting portion 402b is preferably covered with a material having insulation properties by coating or the like.

The head section 404 is provided with a second continuous electrode (a seal member, a first joining member) 422 and second discrete electrodes (a maintaining member, a second joining member) 424 so that the electrodes face the first continuous electrode 372 and the first discrete electrodes 374 of the main body side holding section 342. The second continuous electrode 422 is fixed to one end of a third energization line 422a. The other end of the third energization line 422a is electrically connected to the inner layer 412 through the outer layer 416 and the intermediate layer 414 of the energizing shaft 402. The second discrete electrodes 424 are fixed to one end of a fourth energization line 424a. The other end of the fourth energization line 424a is electrically connected to the outer layer 416 of the energizing shaft 402.

Inside the first continuous electrode 372 disposed on the head section 404, an annular cutter receiving portion 426 is formed to receive the blade of the cutter 364. On the other hand, an annular fluid discharge groove 432 is formed outside the second continuous electrode 422. Outside the fluid discharge groove 432, the holding face (a tissue contact face) 434 is formed at a position higher than the surface of the second continuous electrode 422. That is, the holding face 434 of the detachable side holding section 344 is disposed closer to the main body side holding section 342 than the surface of the second continuous electrode 422. Therefore, the holding face 434 functions as a barrier portion (a dam) which prevents a fluid such as the vapor from escaping to the outside from the vapor discharge groove 432.

Outside the second discrete electrodes 424, an annular vapor discharge groove 436 is formed. The fluid discharge groove 436 is connected to the fluid discharge groove 432 disposed outside the second continuous electrode 422. Outside the fluid discharge groove 436, the holding face (a tissue contact face) 438 is formed at a position higher than the surfaces of the second discrete electrodes 424. In consequence, the holding face 438 functions as a barrier portion (a dam) which prevents a fluid such as the vapor from escaping to the outside from the fluid discharge groove 436.

Furthermore, the fluid discharge groove 432 is connected to a fluid discharge path 432a inside the head section 404 and the inner layer 412 of the energizing shaft 402. The fluid discharge path 432a is positioned away from the central axis of the energizing shaft 402, and is interposed between the outer peripheral surface of the first energizing pipe 356 and the inner peripheral surface of the second energizing pipe 358 through a space between the two enlarged diameter portions 356a of the first energizing pipe 356 of the main body side holding section 342 (see FIG. 20C). The shaft 324 or the handle 322 is provided with a fluid discharge port (not shown) through which the fluid passed between the outer peripheral surface of the first energizing pipe 356 and the inner peripheral surface of the second energizing pipe 358 is discharged to the outside.

As shown in FIGS. 20A to 21, the second conduit 348 extends from the lower end of the energizing shaft 402 to the vertex of the head section 404, extends from the vertex to the outer edge of the head section 404, extends around the outer edge of the head section, is again passed through the energizing shaft 402 and is inserted into the lower end of the energizing shaft 402. Two ends of the second conduit 348 are present in the distal end 402a of the energizing shaft 402. It is to be noted that in FIG. 21, the second conduit 348 supplies the fluid on a side denoted with symbol 348a, and collects the fluid on a side denoted with symbol 348b. The second conduit 348 extends from the distal end 402a of the energizing shaft 402 to the vertex of the head section 404, extends from the vertex to the outer edge of the head section 404, extends around the outer edge of the head section, is again passed through the energizing shaft 402 and is inserted into the distal end 402a of the energizing shaft 402.

Moreover, the end of the second conduit 348 for supplying the fluid is connected to the fluid supplying pipe 360, and the end of the second conduit 348 for collecting the fluid is connected to the first energizing pipe (the fluid collecting pipe) 356. In consequence, when cooling water or the like is supplied through the fluid supplying pipe 360 in a state where the fluid supplying pipe 360 is connected to the first energizing pipe (the fluid collecting pipe) 356 via the second conduit 348, the fluid is collected via the first energizing pipe (the fluid collecting pipe) 356 through the second conduit 348. That is, a fluid such as the cooling water can be circulated through the second conduit 348.

On the holding faces 434 and 438 of the detachable side holding section 344, a detachable side cooling plate 444 such as a copper plate having a satisfactory thermal conductivity is disposed. The cooling plate 444 brought into close contact with the second conduit (the cooling pipe) 348 is fixed to the head section 404. In consequence, when the refrigerant is passed through the second conduit 348, the heat of the refrigerant is conducted from the second conduit 348 to the cooling plate 444. That is, the cooling plate 444 is cooled.

Next, the operation of the treatment system 310 according to this embodiment will be described with reference to the flow chart shown in FIG. 11.

An operator beforehand operates a display section 110 of the energy source 14 shown in FIG. 10 to beforehand set the output conditions of the treatment system 310 (STEP 101). Specifically, the operator beforehand sets the outputs (set powers P1set [W] and P2set [W]) from the first and second high-frequency energy output circuits 104 and 106, threshold values Z1 and Z2 of an impedance Z of a living tissue $L_T$, a time of one output from the second high-frequency energy output circuit 106 (set time t1, t2) and the like.

The holding section 326 and the shaft 324 of the surgical treatment instrument 312 are inserted into an abdominal cavity through, for example, an abdominal wall in a state where the main body side holding section 342 is closed with respect to the detachable side holding section 344. The main body side holding section 342 and the detachable side holding section 344 of the surgical treatment instrument 312 are opposed to the living tissue $L_T$ to be treated.

To grasp the living tissue $L_T$ to be treated between the main body side holding section 342 and the detachable side holding section 344, the holding section opening/closing knob 332 of the handle 322 is operated. At this time, the knob 332 is rotated, for example, clockwise with respect to the handle 322. The energizing pipe 356 is moved to the distal end with respect to the frame 354 of the shaft 324. In consequence, the main body side holding section 342 and the detachable side holding section 344 open, whereby the detachable side holding section 344 can be detached from the main body side holding section 342.

Then, the living tissue $L_T$ to be treated is interposed between the first continuous electrode 372 and first discrete electrodes 374 of the main body side holding section 342 and the second continuous electrode 422 and second discrete electrodes 424 of the detachable side holding section 344. In this state, the grasping section opening/closing knob 332 of the handle 322 is rotated, for example, counterclockwise. In consequence, the detachable side holding section 344 closes with respect to the main body side holding section 342. Thus, the living tissue $L_T$ as the treatment target is held between the main body side holding section 342 and the detachable side holding section 344.

In this state, a pedal 16a of the foot switch 16 is operated. The control section 102 of the energy source 14 judges whether or not the pedal 16a of the switch 16 has been pressed to switch on by the operation of the operator (STEP 102).

When it is judged that the pedal 16a of the switch 16 has been pressed to switch on, high-frequency energy is supplied from the first high-frequency energy output circuit 104 of the energy source 14 to the living tissue (the living tissue of a first region) $L_T$ between the first continuous electrode 372 and the second continuous electrode 422 (STEP 103).

Consequently, the first high-frequency energy output circuit 104 supplies a high-frequency current to the living tissue $L_T$ as the treatment target between the first continuous electrode 372 of the main body side holding section 342 and the second continuous electrode 422 of the detachable side holding section 344 to generate Joule heat in the living tissue $L_T$ grasped between the electrodes 372 and 422, thereby heating the living tissue $L_T$ itself. Consequently, the living tissue $L_T$ is annularly continuously denatured by the first and second continuous electrodes 372 and 422.

At this time, the impedance Z of the grasped living tissue $L_T$ is measured by the first continuous electrode 372, the second continuous electrode 422 and the first high-frequency energy output circuit 104. An impedance Z0 at the start of treatment is, for example, about 60 [Ω] as shown in FIG. 6B. Subsequently, when the high-frequency current flows through the living tissue $L_T$ and the living tissue $L_T$ is cauterized, the value of the impedance Z rises.

Thus, when the living tissue $L_T$ is cauterized, the fluid (a liquid (blood) and/or a gas (water vapor)) is discharged from the living tissue $L_T$. At this time, the holding face 384 of the main body side holding section 342 and the holding face 434 of the detachable side holding section 344 come in closer contact with the living tissue $L_T$ than the first continuous electrode 372 and the second continuous electrode 422. In consequence, the holding faces 384 and 434 function as barrier portions (dams) which prevent the fluid from escaping to the outside of the main body side holding section 342 and the detachable side holding section 344.

Therefore, the fluid discharged from the living tissue $L_T$ is caused to flow from the vapor discharge groove 382 outside the first continuous electrode 372 to the cutter guide groove 362 inside the first continuous electrode 372 or to directly flow into the cutter guide groove 362, and the fluid is, for example, sucked to flow from the main body side holding section 342 to the shaft 324. While the fluid is discharged from the living tissue $L_T$, the fluid continues to flow into the cutter guide groove 362. In consequence, thermal spread is prevented from being caused by the fluid discharged from the living tissue $L_T$ in a state where the temperature is raised, so that a portion which is not the treatment target can be prevented from being influenced.

Moreover, the fluid discharged from the living tissue $L_T$ is caused to flow into the fluid discharge groove 432 outside the second continuous electrode 422, and is, for example, sucked to flow from the inside of the first energizing pipe 356 to the shaft 24 through the fluid discharge path 432a formed in the head section 404 and the energizing shaft 402. While the fluid is discharged from the living tissue $L_T$, the fluid continues to flow into the fluid discharge path 432a. In consequence, the thermal spread is prevented from being caused by the fluid discharged from the living tissue $L_T$ in the state where the temperature is raised, so that the portion which is not the treatment target can be prevented from being influenced.

Next, the control section 102 judges whether the impedance Z during the high-frequency energy output calculated based on a signal from the high-frequency energy output circuit 104 exceeds the threshold value Z1 (here, about 1000 [Ω] as shown in FIG. 6B) beforehand (STEP 1) set in the display section 110 (STEP 104). The threshold value Z1 is set to such a value that the rise ratio of the beforehand known value of the impedance Z falls. Then, when it is judged that the impedance Z is smaller than the threshold value Z1, the processing is returned to STEP 103. That is, the high-frequency energy for the treatment is continuously applied to the living tissue $L_T$ grasped between the first continuous electrode 372 of the main body side holding section 342 and the second continuous electrode 422 of the detachable side holding section 344.

When it is judged that the impedance Z becomes larger than the threshold value Z1, the control section 102 transmits the signal to the first high-frequency energy output circuit 104. This stops the output of the energy from the first high-frequency energy output circuit 104 to the first continuous electrode 372 and the second continuous electrode 422 (STEP 105).

Next, the second high-frequency energy output circuit 106 of the energy source 14 outputs the energy to the living tissue (the living tissue of a second region) $L_T$ between the first and second discrete electrodes 374 and 424 (STEP 106). That is, in a state temporally offset from the time when the first high-frequency energy output circuit 104 supplies the energy to the living tissue $L_T$ between the first and second continuous electrodes 372 and 422 (in the state the output timing is offset), as shown in the middle stage of FIG. 12A, the second high-frequency energy output circuit 106 supplies the high-frequency current to the living tissue $L_T$ between the first and second discrete electrodes 374 and 424.

In consequence, the high-frequency current flows through the living tissue $L_T$ grasped between the main body side holding section 342 and the detachable side holding section 344, to generate heat in the living tissue $L_T$ owing to the function of Joule heat, thereby starting the cauterization of the tissue (the denaturation of the tissue). In this case, the living tissue $L_T$ between the first and second discrete electrodes 374 and 424 is discretely denatured by the discrete electrodes 374 and 424. At this time, the impedance Z of the grasped living tissue $L_T$ is measured by the second high-frequency energy output circuit 106 via the first and second discrete electrodes 374 and 424. Subsequently, when the high-frequency current flows through the living tissue $L_T$ to cauterize the living tissue $L_T$, the value of the impedance Z rises.

Furthermore, after starting the output from the second high-frequency energy output circuit 106, it is judged whether or not the set time t1 has elapsed (STEP 107). When the set time t1 elapses, the second high-frequency energy output circuit 106 stops the output to the first and second discrete electrodes 374 and 424 (STEP 108).

Immediately after the stop, as shown in the lower stage of FIG. 12A, the cooling output circuit 108a supplies the refrigerant through the first and second conduits 346 and 348 (STEP 109). In consequence, the living tissue $L_T$ is cooled by the cooling plates 394 and 444 which come in close contact with the outer peripheral surfaces of the first and second conduits 346 and 348 having a high thermal conductivity. Therefore, the influence of the heat spread from the living tissue $L_T$ as the treatment target between the first and second discrete electrodes 374 and 424 is suppressed by the portions of the tissue which come in close contact with the cooling plates 394 and 444. That is, the thermal spread from the living tissue $L_T$ as the treatment target is suppressed by cooling the living tissue $L_T$ around the living tissue $L_T$ as the treatment target.

Subsequently, it is judged whether or not the set time t2 has elapsed after the refrigerant is started to flow through the first and second conduits 346 and 348 (STEP 110). When the set time t2 elapses, the supply of the refrigerant from the cooling output circuit 108a is stopped (STEP 111).

Immediately after the stop, the second high-frequency energy output circuit 106 supplies the energy to the first and second discrete electrodes 374 and 424 (STEP 112). Subsequently, it is judged whether or not the impedance Z between the first and second discrete electrodes 374 and 424 has reached the threshold value Z2 (STEP 113). When it is judged that the impedance does not reach the threshold value Z2, the processing returns to STEP 106 to again output the energy from the second high-frequency energy output circuit 106 only for the set time t2. That is, the living tissue $L_T$ is repeatedly cauterized and cooled until the impedance Z reaches the threshold value Z2.

Subsequently, when the impedance Z reaches the threshold value Z2, the cooling output circuit 108a supplies the refrigerant through the first and second conduits 346 and 348 to cool the living tissue $L_T$ via the cooling plates 394 and 444 (STEP 114). It is judged whether or not the refrigerant is supplied only for the set time t2 (STEP 115). After supplying the refrigerant only for the set time t2, the supply of the refrigerant is stopped to stop cooling the living tissue $L_T$ (STEP 116).

After the end of such a series of treatments, a buzzer is sounded via the speaker 112 to inform the operator of the end of the treatment (STEP 117).

Here, there will be described a case where, for example, intestinal canals $I_{C1}$ and $I_{C2}$ of a small intestine disposed side by side in an axial direction are joined to each other in a sealed state by use of the treatment system 310 having such a function with reference to FIGS. 22A to 22C.

The display section 110 of the energy source 14 is operated to perform various settings.

A pair of intestinal canals $I_{C1}$ and $I_{C2}$ opposed to each other in an axial direction are held by the holding faces 384 and 388 of the main body side holding section 342 and the holding faces 434 and 438 of the detachable side holding section 344 so as to hold the wall faces of the ends of both the intestinal canals $I_{C1}$ and $I_{C2}$ therebetween.

When the pedal 16a of the foot switch 16 is pressed in this state, the high-frequency energy is supplied to the living tissue $L_T$ between the first and second continuous electrodes 372 and 422. In consequence, the intestinal canals $I_{C1}$ and $I_{C2}$ are heated and denatured by the first and second continuous electrodes 372 and 422.

Subsequently, when the impedance Z of the living tissue $L_T$ between the first and second continuous electrodes 372 and 422 reaches the predetermined threshold value Z1, the output from the first high-frequency energy output circuit 104 is stopped.

When the impedance Z of the living tissue $L_T$ between the first and second continuous electrodes 372 and 422 reaches the predetermined threshold value Z1, the intestinal canals $I_{C1}$ and $I_{C2}$ are heated, denatured, and joined to each other by the first and second continuous electrodes 372 and 422. That is, the first and second continuous electrodes 372 and 422 annularly seal the ends of the intestinal canals $I_{C1}$ and $I_{C2}$ to each other.

Immediately after the stop, the second high-frequency energy output circuit 106 supplies the energy to the living tissue $L_T$ between the first and second discrete electrodes 374 and 424. In consequence, the intestinal canals $I_{C1}$ and $I_{C2}$ are heated and denatured by the first and second discrete electrodes 374 and 424.

Subsequently, after the elapse of the set time t1, the second high-frequency energy output circuit 106 is once stopped, and the cooling output circuit 108a supplies the refrigerant to the first and second conduits 346 and 348 only for the predetermined set time t2.

Immediately after the supply, the second high-frequency energy output circuit 106 outputs the energy, thereby measuring the impedance Z while cauterizing the tissue.

Subsequently, it is judged whether or not the impedance Z of the living tissue $L_T$ between the first and second discrete electrodes 374 and 424 has reached the predetermined threshold value Z2. When the impedance Z does not reach the threshold value Z2, the second high-frequency energy output circuit 106 again outputs the energy and stops the output, the refrigerant is supplied, and the supply is stopped to measure the impedance Z. On the other hand, when the impedance Z reaches the value Z2, the output from the second high-frequency energy output circuit 106 is stopped, the refrigerant is supplied, and the supply is stopped to sound the buzzer, thereby ending the treatment.

When the impedance Z of the living tissue $L_T$ between the first and second discrete electrodes 374 and 424 reaches the predetermined threshold value Z2, the intestinal canals $I_{C1}$ and $I_{C2}$ are heated, denatured, and joined to each other by the first and second discrete electrodes 374 and 424. That is, the first and second discrete electrodes 374 and 424 discretely join the living tissues outside the annularly sealed portions of the ends of the intestinal canals $I_{C1}$ and $I_{C2}$ so that the living tissues come in close contact with each other. The intestinal canals $I_{C1}$ and $I_{C2}$ are continuously and discretely denatured, and joined (anastomosed) to each other.

Moreover, while the intestinal canals $I_{C1}$ and $I_{C2}$ are grasped between the main body side holding section 342 and the detachable side holding section 344, the cutter driving knob 334 shown in FIG. 19 is operated, and the cutter 364 is moved forwards from the state shown in FIG. 20B along the cutter guide groove 362. When the cutter 364 moves forwards, the inside of the portion denatured and joined by the first and second continuous electrodes 372 and 422 is cut into a circular shape by the blade at the distal end of the cutter 364. Therefore, as shown in FIG. 22C, a portion between substantially circular sealed portions of the wall faces of the intestinal canals $I_{C1}$ and $I_{C2}$ is cut so as to acquire the circular communication state between the intestinal canals $I_{C1}$ and $I_{C2}$.

The cutter driving knob 334 is operated in this state to move the cutter 364 backwards. Afterward, the holding section opening/closing knob 332 of the handle 322 is operated to open the main body side holding section 342 and the detachable side holding section 344. As shown in, for example, FIG. 22C, a portion outside the portion continuously joined by the first and second continuous electrodes 372 and 422 is discretely denatured. As described above, the output supplied from the second high-frequency energy output circuit 106 to the first and second discrete electrodes 374 and 424 is set to a high output, and hence the discretely denatured and joined portion is securely joined and accordingly, has a peeling resistance.

Therefore, the portion of the living tissue denatured by the first and second discrete electrodes 374 and 424 exerts such a force as to more securely bring the living tissues into close contact with each other. A force is exerted in such a direction as to release the joined intestinal canals $I_{C1}$ and $I_{C2}$ sometimes, but the portions of the living tissue denatured by the first and second discrete electrodes 374 and 424 exert such a force as to bring the living tissues into close contact with each other. This generates a mutual network between the living tissues of the intestinal canals $I_{C1}$ and $I_{C2}$ which are not denatured, and a tissue regenerative force of the living tissues is exerted to regenerate the living tissues of the intestinal canals $I_{C1}$ and $I_{C2}$ earlier.

As described above, according to this embodiment, an effect is obtained as follows. The description of the effect described in the first embodiment is omitted.

The continuous electrodes 372 and 422 and the discrete electrodes 374 and 424 are arranged in the main body side holding section 342 and the detachable side holding section 344, and the output amounts, output timings and the like of the energy input into the continuous electrodes 372 and 422 and the energy input into the discrete electrodes 374 and 424 are separately set. Moreover, the output amounts, the output timings and the like are appropriately set in accordance with the treatment target, whereby the treatment which is optimum for the treatment target can be set and performed.

In particular, when the living tissues are discretely treated by the discrete electrodes 374 and 424 so as to bring the tissues into close contact with each other, a process of cooling the living tissue is performed, whereby the living tissue which is not the treatment target can be prevented from being influenced by the energy supplied from the discrete electrodes 374 and 424.

Moreover, this embodiment has been described by use of the bipolar type surgical treatment instrument 312, but a monopolar type high-frequency treatment is preferably performed as described in the first embodiment with reference to FIG. 3E.

Some embodiments including a plurality of modifications have specifically been described with reference to the drawings, but this invention is not limited to the above embodiments, and includes all implementations performed without departing from the scope of the invention.

According to these embodiments, there can be provided a treatment system which can optimally apply energy to electrodes to efficiently treat a living tissue, a treatment instrument, and a method for treating a living tissue by use of energy.

What is claimed is:

1. A treatment system configured to exert energy on at least two living tissues to treat the living tissues, comprising:
  first and second holding members configured to hold the living tissues, each including a holding face opposed to each other, and also including a distal end and a proximal end, the two ends defining a longitudinal direction;
  a cutter guide groove formed in at least one of the first and second holding members and configured to guide a cutter from the proximal end to the distal end;
  a seal member disposed on the holding face of the first holding member, surrounding the cutter guide groove, and configured to seal the living tissues and form a sealed region in the living tissues when the energy is exerted on the sealed region through the seal member;
  maintaining members disposed on the holding face of the first holding member between an outer edge of the holding face of the first holding member and the seal member and configured to exert energy on an outer periphery of the sealed region; and
  a control section configured to offset energy output timings of the seal member and the maintaining members,
  wherein:
  each of the maintaining members has conductive properties and is formed into a circular shape and
  the maintaining members are aligned in parallel with the longitudinal direction, electrically insulated from each other, physically isolated from each other, and configured to discretely join the living tissues together her by the energy exerted through the maintaining members and maintain a contact state between the living tissues.

2. The treatment system according to claim 1, wherein each of the seal member and the maintaining members includes at least one of a high-frequency electrode and a heater.

3. The treatment system according to claim 1, further comprising at least one barrier portion disposed on at least one of the outer edge of the holding face of the first holding member and an outer edge of the holding face of the second face of the second holding member, wherein the barrier portion is positioned to be as high as or higher than the seal member and the maintaining members.

4. The treatment system according to claim 1, wherein the holding members include channels that are provided in the vicinity of the seal member and the maintaining members, and through which a fluid generated from the living tissue held by the holding members is passed.

5. The treatment system according to claim 1, further comprising a cooling member configured to be provided in the vicinity of the maintaining members to cool the maintaining members and/or the vicinity of the maintaining members,
wherein the control section is configured to independently control the energy output timings of the seal member, the maintaining members and the cooling member.

* * * * *